United States Patent
Nagase et al.

(10) Patent No.: US 10,858,646 B2
(45) Date of Patent: Dec. 8, 2020

(54) METHOD AND KIT FOR CONCENTRATING TARGET DOUBLE-STRANDED NUCLEIC ACID MOLECULES USING A PYRROLE-IMIDAZOLE-CONTAINING POLYAMIDE

(71) Applicant: TOPPAN PRINTING CO., LTD., Taito-ku (JP)

(72) Inventors: Hiroki Nagase, Taito-ku (JP); Kei Tsukamoto, Taito-ku (JP); Shiro Kitano, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 0 days.

(21) Appl. No.: 15/948,124

(22) Filed: Apr. 9, 2018

(65) Prior Publication Data

US 2018/0230452 A1 Aug. 16, 2018

Related U.S. Application Data

(63) Continuation of application No. PCT/JP2016/004530, filed on Oct. 7, 2016.

(30) Foreign Application Priority Data

Oct. 8, 2015 (JP) .................................. 2015-200599

(51) Int. Cl.
| | |
|---|---|
| C12N 15/10 | (2006.01) |
| C08G 69/10 | (2006.01) |
| C08G 73/06 | (2006.01) |
| G01N 1/40 | (2006.01) |
| C12N 15/09 | (2006.01) |
| C07H 1/06 | (2006.01) |
| C07H 21/00 | (2006.01) |

(52) U.S. Cl.
CPC ........... *C12N 15/1006* (2013.01); *C07H 1/06* (2013.01); *C07H 21/00* (2013.01); *C08G 69/10* (2013.01); *C08G 73/0611* (2013.01); *C08G 73/0616* (2013.01); *C12N 15/09* (2013.01); *G01N 1/405* (2013.01)

(58) Field of Classification Search
CPC ............ C12N 15/1006; C08G 73/0611; C08G 69/10; C08G 73/0616; G01N 1/405
USPC ........................................................ 536/114
See application file for complete search history.

(56) References Cited

U.S. PATENT DOCUMENTS

| | | | |
|---|---|---|---|
| 7,067,622 B2 | 6/2006 | Sugiyama et al. | |
| 7,718,369 B2 | 5/2010 | Tomlins et al. | |
| 8,541,169 B2 | 9/2013 | Srivastava et al. | |
| 2004/0185453 A1* | 9/2004 | Myerson | C07H 21/04 435/6.12 |
| 2009/0208937 A1 | 8/2009 | Chinnaiyan et al. | |

FOREIGN PATENT DOCUMENTS

| | | |
|---|---|---|
| JP | 3231045 B | 11/2001 |
| JP | 4012145 B | 11/2007 |
| JP | 2009-507492 A | 2/2009 |
| JP | 2010-505446 A | 2/2010 |
| JP | 2010-532663 A | 10/2010 |
| JP | 2011-518552 A | 6/2011 |
| WO | WO 97/30975 | 8/1997 |
| WO | WO 2012/111687 | 8/2012 |

OTHER PUBLICATIONS

Serie et al. Pyrrole—Imidazole Polyamide Targeting Transforming Growth Factor β1 Ameliorates Encapsulating Peritoneal Sclerosis. Peritoneal Dialysis International, vol. 32, pp. 462-472, 2012. (Year: 2012).*
Taylor et al. Sequence-Specific DNA Alkylation Targeting for Kras Codon 13 Mutation by Pyrrole—Imidazole Polyamide seco-CBI Conjugates. Chem. Eur. J. 2014, 20, 1310-1317. DOI: 10.1002/chem.201303295 (Year: 2014).*
Nagase et al. Abstract 2602: KRAS G12D and G12V specific alkylating agent (KR12) inhibits growth of colon cancer with those KRAS mutations in vitro as well as in vivo. Apr. 5-9, 2014; San Diego, CA. Philadelphia (PA): AACR; Cancer Res 2014;74(19 Suppl): Abstract nr 2602. (Year: 2014).*
International Search Report dated Jan. 10, 2017, in PCT/JP2016/004530, filed Oct. 7, 2016.
Arcamone et al., "Structure and Synthesis of Distamycin A", Nature, vol. 203, 1964, pp. 1064-1065.
Nelsen et al., "Sequence-Selective Recognition of DNA by Strand Displacement with a Thymine-Substituted Polyamide", Science, vol. 254, 1991, pp. 1497-1500.
Cho et al., "Cyclic polyamides for recognition in the minor groove of DNA", Proc. Natl. Acad. Sci. USA 92 (1995), 10389-10392.
Kawashima et al., "Design, Synthesis and Evaluation of Polyamide-nucleoside Hybrids and Oligonucleotides Conjugated Hybrid as a Novel Gene Expression Control Compound", Yakugaku Zasshi 130 (3) 355-375 (2010), pp. 355-375 (with English abstract).

* cited by examiner

*Primary Examiner* — Yih-Horng Shiao
(74) *Attorney, Agent, or Firm* — Oblon, McClelland, Maier & Neustadt, L.L.P.

(57) ABSTRACT

A method of separating a target double-stranded nucleic acid molecule from a sample including the target double-stranded nucleic acid molecule and a non-target double-stranded nucleic acid molecule, including (1) mixing the sample, a pyrrole-imidazole-containing polyamide (first PI polyamide) modified with a first linker molecule and capable of specifically binding to a sequence of the target double-stranded nucleic acid molecule, and a carrier a modified with a first ligand capable of specifically binding and/or adsorbing to the first linker molecule such that a mixed solution is produced, (2) forming a complex A by binding the carrier a to the first PI polyamide with which the target double-stranded nucleic acid molecule is bound in the mixed solution, and (3) separating the complex A from the mixed solution.

20 Claims, 20 Drawing Sheets

FIG.4

[FIRST INVENTION]

```
┌─────────────────────────────────────────────────────────────────┐  ⌐S402
│   STEP OF MIXING "SAMPLE", "FIRST PI POLYAMIDE" AND "CARRIER a" │
└─────────────────────────────────────────────────────────────────┘
```
```
┌─────────────────────────────────────────────────────────────────┐  ⌐S404
│                    STEP OF FORMING COMPLEX A                    │
│   ( "TARGET DOUBLE-STRANDED DNA + FIRST PI POLYAMIDE + CARRIER A" )│
└─────────────────────────────────────────────────────────────────┘
```
```
┌─────────────────────────────────────────────────────────────────┐  ⌐S406
│              SEPARATION AND RECOVERY OF COMPLEX A               │
└─────────────────────────────────────────────────────────────────┘
```

"SAMPLE" USED HEREIN MEANS A MIXED SOLUTION OF TARGET DOUBLE-
STRANDED DNA AND NON-TARGET DOUBLE-STRANDED DNA.

"SAMPLE" USED HEREIN MEANS A MIXED SOLUTION OF TARGET DOUBLE-STRANDED DNA AND NON-TARGET DOUBLE-STRANDED DNA.

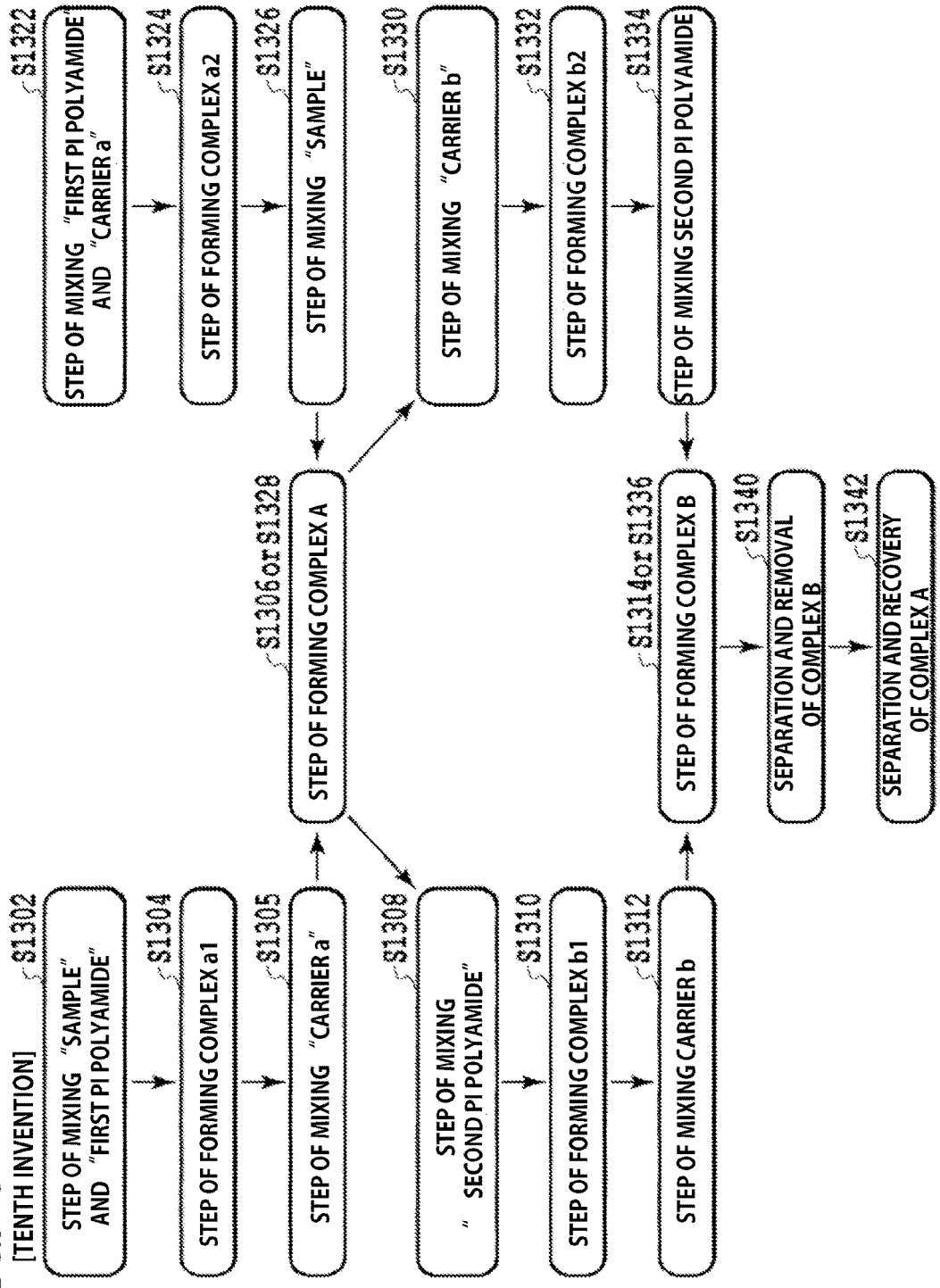

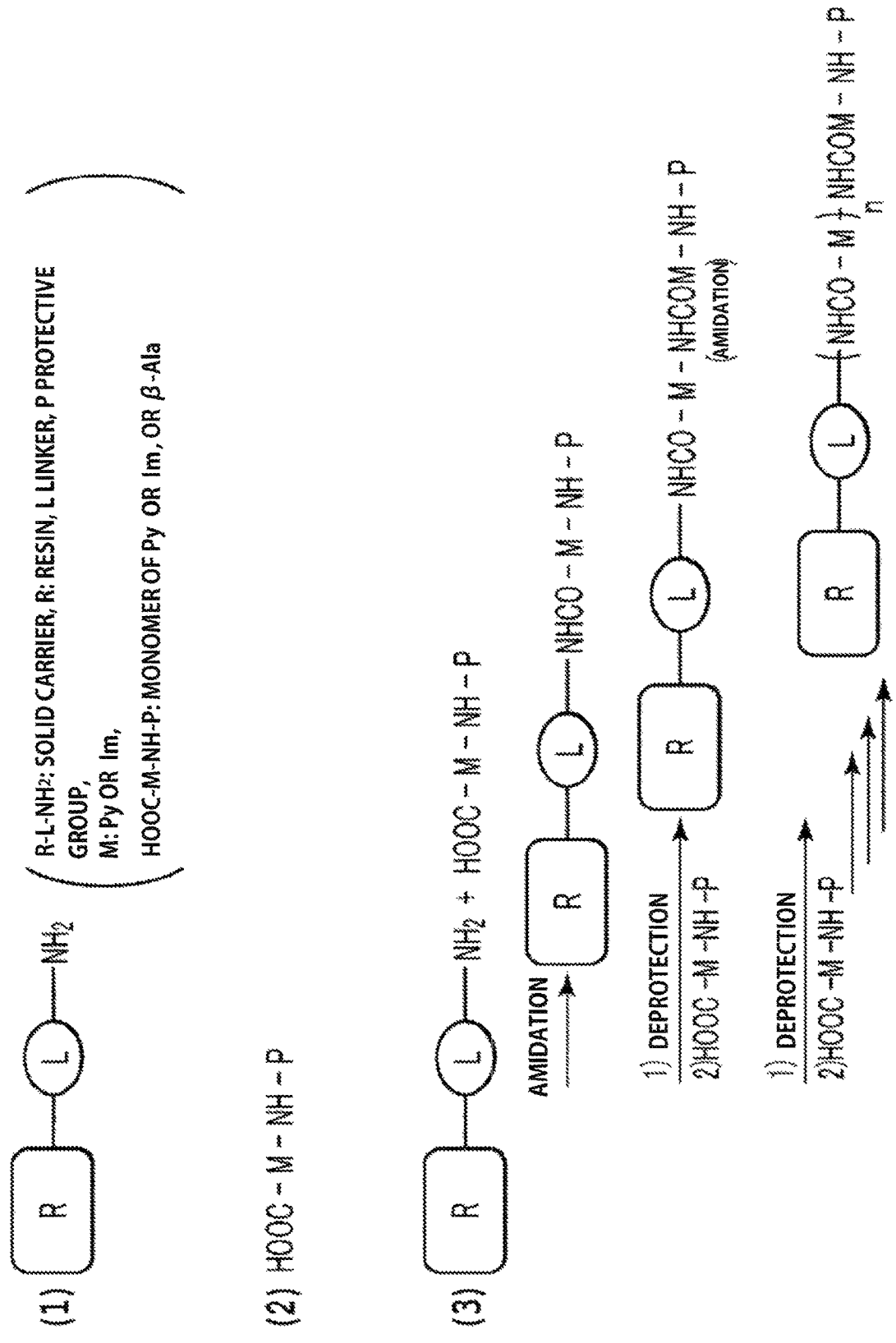

METHOD AND KIT FOR CONCENTRATING TARGET DOUBLE-STRANDED NUCLEIC ACID MOLECULES USING A PYRROLE-IMIDAZOLE-CONTAINING POLYAMIDE

CROSS-REFERENCE TO RELATED APPLICATIONS

The present application is a continuation of International Application No. PCT/JP2016/004530, filed Oct. 7, 2016, which is based upon and claims the benefits of priority to Japanese Application No. 2015-200599, filed Oct. 8, 2015. The entire contents of these applications are incorporated herein by reference.

BACKGROUND OF THE INVENTION

Field of the Invention

The present invention relates to a method and kit for concentrating double-stranded nucleic acid molecules of a target gene by discriminating a one or more-base difference in sequence of the target gene using a pyrrole-imidazole-containing polyamide.

Discussion of the Background

The recent remarkable development of molecular biology and the study results accumulated up to now not only contribute to the elucidation of life phenomena, but also greatly contribute to medical care. Especially, genetic medical treatments using molecular biological techniques have been remarkably developed and now rapidly applied to clinical fields. Moreover, it has been clarified that diversity at the level of a genetic nucleic acid sequence takes part in a variety of diseases, so that diagnosis at the level of the genetic nucleic acid sequence has become necessary and essential against such diseases. Here, the diversity at the level of the genetic nucleic acid sequence means a genetic mutation such as deletion, addition or substitution in the genetic nucleic acid sequence.

It has been made clear nowadays that a great number of functional deficiencies of enzymes, known from old times as congenital metabolic abnormalities, are based on genetic diseases. As a method of detecting these diseases, there is known one wherein the genetic base sequence of a healthy subject who is free of congenital abnormality and the genetic base sequence of a patient undergoing metabolic abnormality are compared with each other with respect to the genes of a protein or enzyme taking part in a specific type of metabolism thereby detecting a base sequence mutation in the genes of the patient. This has become a very effective technique for genetic diagnosis of a disease based on these genes.

With the diagnosis based on the genes of a disease, e.g., a cancer, which would be caused by an acquired genetic abnormality, it is very difficult to collect cancer cells alone from a cancer piece because normal cells and cancer cells invariably coexist. Accordingly, normal cells are always unavoidably incorporated into a sample, with the attendant problem that the correctness of the detection of a genetic mutation decreases. Therefore, it is needed to selectively detect mutated genes alone from cancer cells.

If it is intended to merely increase the amount of genes, target genes can be simply amplified according to a gene amplification method such as a PCR (polymerase chain reaction) method or the like. On the other hand, where the difference between cancer cells and normal cells, or between a healthy subject and a specific genetic patient ascribed to the genetic mutation is discriminated, it is required not only to merely increase the amount of genes, but also to increase a ratio of mutated genes contained in a sample.

More particularly, where an absolute amount of causal mutated genes of a disease in a sample is extremely small, it would be almost impossible to confirm the mutated genes in this state. Hence, it has been demanded to develop a method of concentrating arbitrarily selective target genes. Preferably, it is desirable that the target genes concentrated by these methods be able to be introduced into existing gene diagnosis systems.

In recent years, a PCR clamp method is known as a general concentration method, in which normal genes and mutated genes are discriminated and a small amount of mutated genes are preferentially amplified by application of the PCR technology. For instance, there is known a method (PTL 2) wherein the wild-type nucleic acid sequence of target genes is clamped with an artificial nucleic acid, such as a locked nucleic acid (LNA)-containing oligonucleotide, a crosslinked nucleic acid (BNA)-containing oligonucleotide, or a peptide nucleic acid (PNA)-containing oligonucleotide, to increase the ratio of mutated genes capable of taking part in PCR in a sample thereby enabling more amplification of the mutated genes. Although the PCR clamp method is a technique which has been widely used in view of its high freedom in design of an artificial nucleic acid sequence and a high sequence specificity, there are inserted bases that differ from a DNA template sequence due to the fidelity (fiderity) upon the PCR amplification with a Taq polymerase. It has been reported that the insertion of the different bases into the DNA template sequence ascribed to the non-fidelity of the Taq polymerase involves a problem that leads to a cause of false-positive results in diagnosis or detection. This PCR clamp method requires a high-accuracy temperature control apparatus and the strict control of a reaction system, which are essential for the PCR technology.

It is known (NPL 1) that aside from those artificial nucleic acids, low molecular weight compounds, such as substances having antitumor activity and including distamycin, netropsin, daunorubicin, duocarmycin and the like, have specific discriminability against double-stranded structures or specific genes.

This low molecular weight compound is called a minor groove binder because it is able to specifically discriminate and bind the minor group (minor groove: Minor Groove) of a DNA double-stranded structure. On the other hand, the above-described artificial nucleic acids are able to specifically discriminate and bind a major groove (major groove: Major Groove) and are thus called major groove binder.

Besides, there has been reported a method of concentrating a target gene nucleic acid by recovering mutated genes on a carrier through a sequence-specific oligonucleotide and a linker molecule, or a method of concentrating a target genetic nucleic acid by removing normal genes by the same procedure. However, there has never been a report on the case where a one-base difference in a target gene is well discriminated using these methods.

The minor groove binder such as a low molecular weight compound including distamycin or the like as mentioned above has some limitations on the type of discriminable base sequence or gene, with no freedom on a target. Under these circumstances, pyrrole-imidazole-containing polyamides have been developed and received attention in recent years. The pyrrole-imidazole-containing polyamide having such a structure exemplified in FIG. 1 are known as ones which have a high degree of freedom in molecular design enabling the specific binding to a base sequence of a specified target gene (PTLs 1 to 4).

However, although these pyrrole-imidazole-containing polyamides have been now reported in a great number of application examples for use as a drug, there are a really small number of application examples in diagnosis relying on the PCR technology such as of the afore-discussed artificial nucleic acids and the like, or other nucleic acid preparation process (such as of the concentration of target nucleic acid).

PTL 1: JP 2010-505446 A
PTL 2: JP 2011-518552 A
PTL 3: JP 2009-507492 A
PTL 4: JP 2010-532663 A
PTL 5: JP 3231045 B
PTL 6 JP 4012145 B
PTL 7: WO 2012/111687
NPL 1: F ARCAMONE et al, Nature 203: 1064-1065, 1964
NPL 2: Nelsen, P. E. et al, Science Vol. 254, pp. 1497-1500
NPL 3: Cho J et al, PNAS 92: 10389-10392, 1995
NPL 4: YAKUGAKU ZASSHI 130 (3) 355-375 (2010), written by Etsuko Kawashima and Kazuhiro Kamaike

SUMMARY OF THE INVENTION

According to an aspect of the present invention, a method of separating a target double-stranded nucleic acid molecule from a sample including the target double-stranded nucleic acid molecule and a non-target double-stranded nucleic acid molecule includes (1) mixing the sample, a pyrrole-imidazole-containing polyamide (first PI polyamide) modified with a first linker molecule and capable of specifically binding to a sequence of the target double-stranded nucleic acid molecule, and a carrier a modified with a first ligand capable of specifically binding and/or adsorbing to the first linker molecule such that a mixed solution is produced, (2) forming a complex A by binding the carrier a to the first PI polyamide with which the target double-stranded nucleic acid molecule is bound in the mixed solution, and (3) separating the complex A from the mixed solution.

According to another aspect of the present invention, a method of removing a non-target double-stranded nucleic acid molecule from a sample including a target double-stranded nucleic acid molecule and the non-target double-stranded nucleic acid molecule, includes (1) mixing the sample, a pyrrole-imidazole-containing polyamide (second PI polyamide) modified with a second linker molecule and capable of specifically binding to a sequence of the non-target double-stranded nucleic acid molecule, and a carrier b modified with a second ligand molecule capable of specifically binding and/or adsorbing to the second linker molecule such that a mixed solution is produced, (2) forming a complex B by binding the carrier b to the second PI polyamide with which the non-target double-stranded nucleic acid molecule is bound in the mixed solution, and (3) removing the complex B from the mixed solution.

According to another aspect of the present invention, a method of separating a target double-stranded nucleic acid molecule from a sample including the target double-stranded nucleic acid molecule and a non-target double-stranded nucleic acid molecule, includes (1) mixing the sample, a pyrrole-imidazole-containing polyamide (first PI polyamide) modified with a first linker molecule and capable of specifically binding to a sequence of the target double-stranded nucleic acid molecule, a carrier a modified with a first ligand molecule capable of specifically binding and/or adsorbing to the first linker molecule, a pyrrole-imidazole-containing polyamide (second PI polyamide) modified with a second linker molecule and capable of specifically binding to a sequence of the non-target double-stranded nucleic acid molecule, and a carrier b modified with a second ligand molecule capable of specifically binding and/or adsorbing to the second linker molecule, (2) forming a complex A by binding the carrier a to the first PI polyamide with which the target double-stranded nucleic acid molecule is bound in the mixed solution 1 and a complex B by binding the carrier b to the second PI polyamide with which the non-target double-stranded nucleic acid molecule is bound in the mixed solution 1, (3) removing the complex B from the mixed solution 1, and (4) separating the complex A from the mixed solution 1.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4 is a flow chart of a first embodiment of the invention in the present specification.

FIG. 13 is a flow chart of a tenth embodiment of the invention in the present specification.

FIG. 15 is a scheme (No. 1) of a synthetic method of a PI polyamide modified with a linker molecule.

DESCRIPTION OF THE EMBODIMENTS

Figure 1:
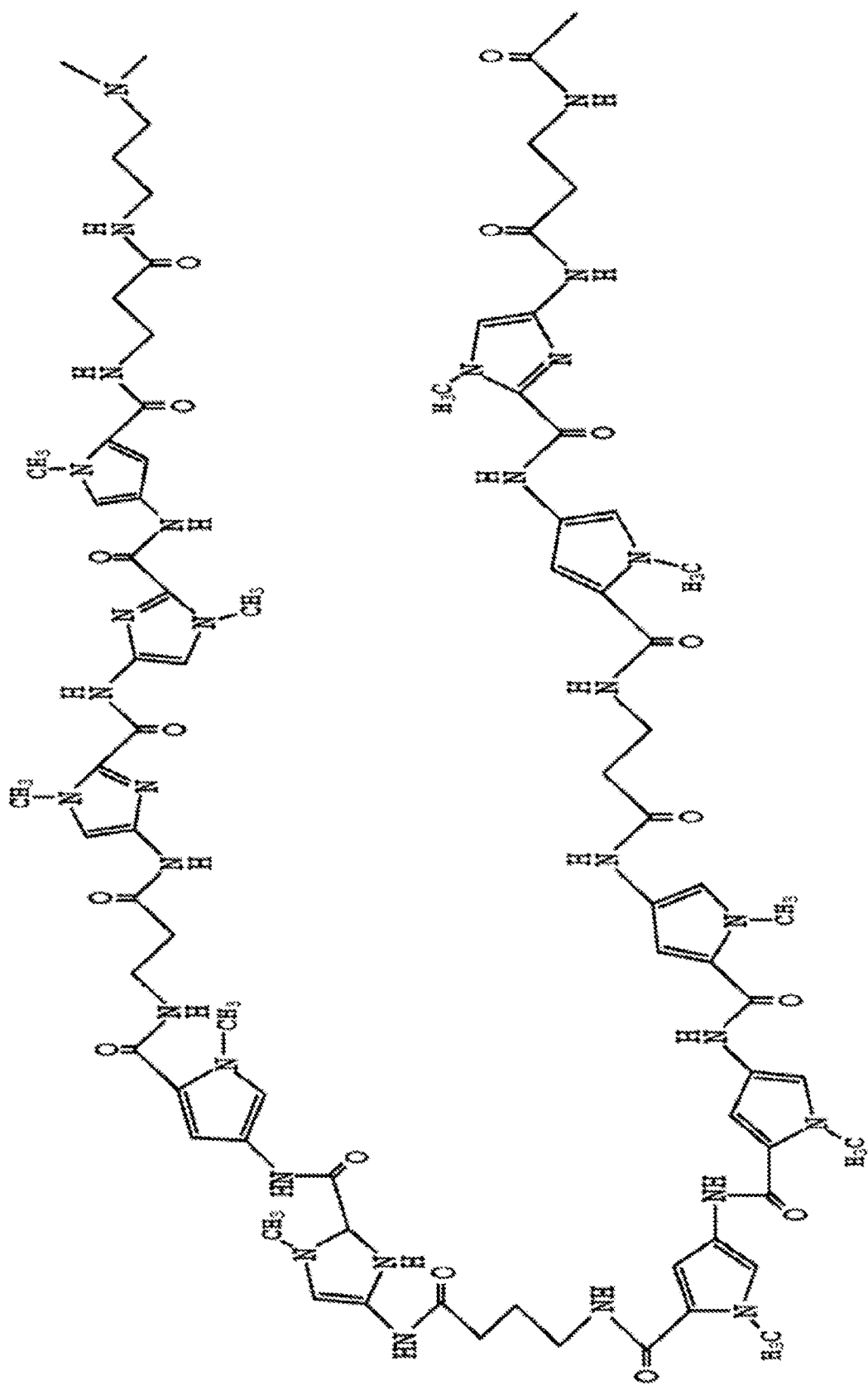
FIG. 1 is a view showing an example of a hitherto employed pyrrole-imidazole-containing polyamide.

The embodiments will now be described with reference to the accompanying drawings, wherein like reference numerals designate corresponding or identical elements throughout the various drawings.

1. Definitions

The term "concentration" used herein means to enhance concentration by removing non-target double-stranded nucleic acid molecules and selectively recovering target double-stranded nucleic acid molecules from a mixed solution of the target double-stranded nucleic acid molecules and the non-target double-stranded nucleic acid molecules.

The term "(specific gene) family" is one that includes both specific gene superfamily and subfamily.

2. Summary of Inventive Aspects

The technology of discriminating base sequences of nucleic acids has been expected not only with respect to such a genetic diagnosis system as set out before, but also with respect to applications in the field of drug discovery. Especially, molecularly targeted drugs, to which attention has been recently drawn in the field of cancer therapy, cover a wide variety of target molecules. In fact, the development of molecularly targeted drugs targeting proteins, antibodies or nucleic acids has been in progress, and techniques of discriminating target molecules have been stepped into the stage of clinical tests. In the clinical tests, there has been demanded a technique of discriminating a small amount of nucleic molecules having a mutation in one or more base sequences existing in a sample. In this sense, the concentration method according to an embodiment of the present invention is one suited for concentrating such target double-stranded nucleic acid molecules.

On the other hand, the afore-stated PCR clamp method using artificial nucleic acids is a concentration method wherein a trace of mutated genes is amplified, but is known to have such problems as stated in the prior art technique although having been expected and developed to serve for applications to drugs targeting nucleic acid molecules or genes having specific base sequences.

The method for concentrating target double-stranded nucleic acid molecules according to an embodiment of the invention is broadly classified into two methods (first aspect and second aspect).

Figure 2A:
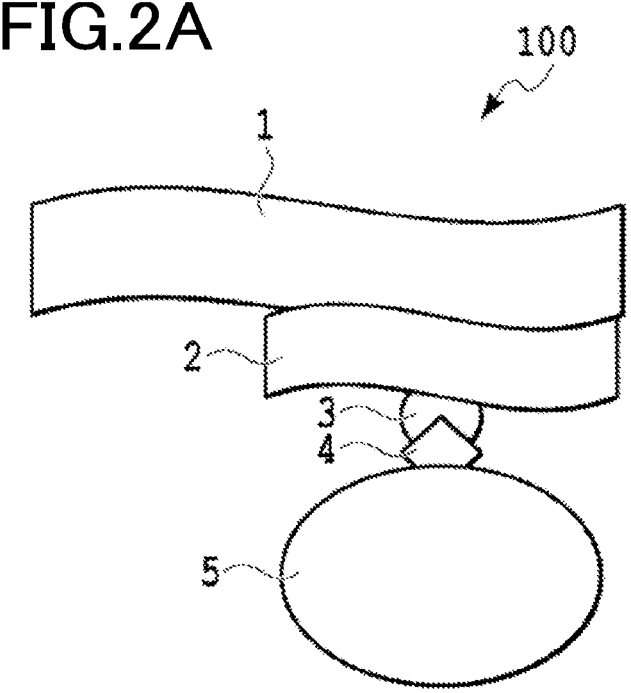
FIG. 2A is a schematic view showing a complex of standard double-stranded DNA, a first PI polyamide, and a carrier a formed in an embodiment of the present invention.
Figure 3A:
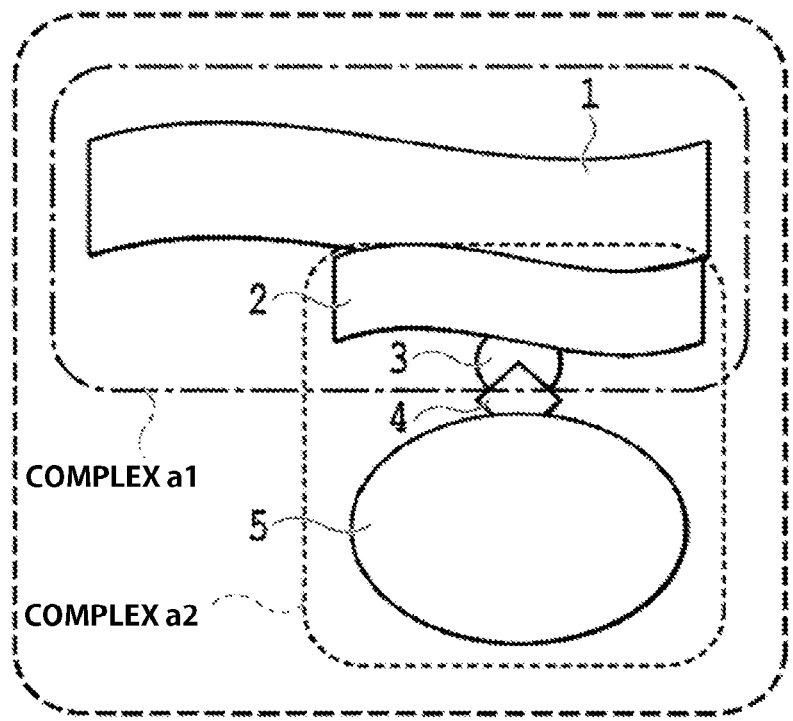
FIG. 3A is a schematic view showing a complex A formed in an embodiment of the invention.

The first one (first aspect) is directed to a method for directly concentrating target double-stranded nucleic molecules in a sample wherein the concentration is carried out in such a way that a complex A (100) shown in FIGS. 2A and 3A is formed and this complex A (100) is separated and recovered. Illustration is now made with reference to FIGS. 2A and 3A.

FIG. 2A is a schematic view of a complex A (100) formed for recovery and concentration of target double-stranded nucleic acid molecules. As shown in FIG. 2A, the complex A (100) includes, as constituent elements, a target double-stranded nucleic acid molecule (1), a first PI polyamide (2) discriminating the target double-stranded nucleic acid molecule (1), a first linker molecule (3), a first ligand molecule (4) capable of specifically binding to the first linker molecule (3), and a carrier a (5).

Figure 2B:
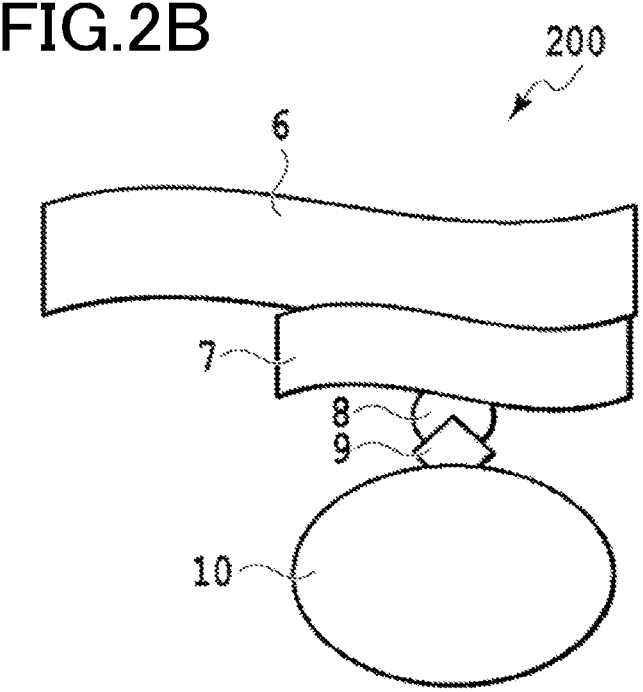
FIG. 2B is a schematic view showing a complex of non-standard double-stranded DNA, a second PI polyamide, and a carrier b formed in an embodiment of the invention.
Figure 3B:
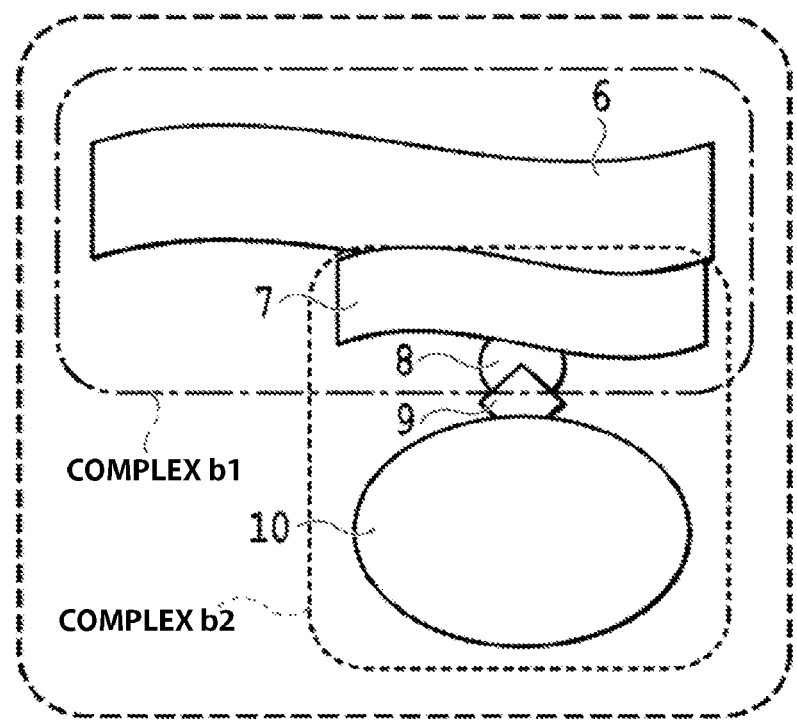
FIG. 3B is a schematic view showing a complex B formed in an embodiment of the invention.

Another method (second aspect) is directed to a method having a procedure of removing a non-target double-stranded nucleic acid molecule in a sample according to a plurality of steps wherein a complex B shown in FIGS. 2B and 3B is formed and this complex B (200) is removed from the sample, followed by concentration by separating and recovering the resulting target double-stranded nucleic acid molecule (1).

Here, FIG. 2B is a schematic view of the complex B (200) containing a non-target double-stranded nucleic acid molecule (6). As shown in FIG. 2B, the complex B (200) includes, as essential elements, a non-target double-stranded nucleic acid molecule (6), a second PI polyamide (7) discriminating the non-target double-stranded nucleic acid molecule (6), a second linker molecule (8), a second ligand molecule (9) capable of specifically binding to the second linker molecule (8), and a carrier b (10).

The first aspect of the invention is a concentration method making use of the pyrrole-imidazole-containing polyamide (2) that has such a sequence and structure capable of binding to a specific base sequence of a double-stranded nucleic acid molecule (1) of a target gene, but incapable of binding to a sequence having a one-base mutation. When using the first PI polyamide (2) modified with the first linker molecule (3) and the carrier a (5) modified with the first ligand molecule (4) capable of specifically binding to the first linker molecule (4), the target double-stranded nucleic acid molecule (1) and the non-target double-stranded nucleic acid molecule (6) can be separated from each other, thereby enabling the concentration of the target double-stranded nucleic acid molecule (1). Moreover, a binding subject may be selected from either the target double-stranded nucleic acid molecule (1) or the non-target double-stranded nucleic acid molecule (6) through the molecular design of the PI polyamide.

The method for recovering and concentrating the target double-stranded nucleic acid molecule (1) according to the first aspect includes the following three methods (first to third embodiments of invention). This will now be described with reference to FIG. 3A.

A first method is directed to one (first embodiment of invention) wherein all three of a sample containing a target double-stranded nucleic acid molecule (1), a first PI polyamide (2) modified with a first linker molecule (3), and a carrier a (5) modified with a first ligand molecule (4) are mixed to form a complex A (100), followed by concentration thereof.

A second method is one (second embodiment of invention) wherein a sample containing a target double-stranded nucleic acid molecule (1) and a first PI polyamide (2) modified with a first linker molecule (3) are mixed together to form a complex a1, followed by further mixing with a carrier 1 (5) modified with a first ligand molecule (4) to form a complex A (100) and concentrating it (second embodiment of invention).

A third method is one (third embodiment of invention) is one wherein a first PI polyamide (2) modified with a first linker molecule (3) and a carrier a (5) modified with a first ligand molecule (4) are mixed together to form a complex a (2), followed by further mixing with a target double-stranded nucleic acid molecule (1) to form a complex A (100) and concentrating it (third embodiment of invention).

It will be noted that in FIG. 3A, the "complex A (100)" is shown as including the "complex a1" and the "complex a2". Here, the complex wherein the target double-stranded nucleic acid molecule (1) and the first PI polyamide (2) modified with the first linker molecule (3) are bound together is defined as "complex a1". The complex wherein the first PI polyamide (2) and the carrier a (5) modified with the first ligand molecule (4) capable of specifically binding to the first linker molecule (3) is defined as "complex a2". The complex wherein the complex a1 and the complex a2 are bound through the interaction of the first linker molecule (3) with the first ligand molecule (4) capable of specifically binding to the first liker molecule is defined as "complex A".

As shown in FIGS. 2A and 3A, the first PI polyamide (2) is modified with the first linker molecule (3) (e.g. biotin), and the carrier a (5) is modified with the first ligand (4) molecule (e.g., streptavidin) capable of specifically binding to the first linker molecule (3). The first polyamide (2) is able to specifically bind to the target double-stranded nucleic acid molecule (1).

The thus formed complex A (100) is separated, recovered and concentrated, and is subjected to analyses. Although depending on the type of material for the carrier a (5) used, the method of separating and recovering the formed complex A (100) is such that the complex A (100) can be pulled by a magnet to collect the complex A (100) in the case that the carrier a (5) is made of a magnetic body. Where the carrier 1 (5) is in the form of particles or a gel, the separation and recovery can be performed by pipetting or decantation after centrifugal separation. The more specific conditions of the mixing method, the formation methods of the complexes and the separation methods are described hereinafter in the present specification.

The method (second aspect) of concentrating the target double-stranded nucleic acid molecules (1) through the steps of recovering and removing the non-target double-stranded nucleic acid molecule (6) can be carried out according to the following three methods (fourth to tenth embodiments of invention). This is illustrated with reference to FIG. 3B.

A first method is one wherein a sample containing non-target double-stranded nucleic acid molecules (6), a second PI polyamide (7) modified with a second linker molecule (8), and a carrier b (10) modified with a second ligand molecule (9) are mixed to form a complex B (200), and the complex B (200) is removed, followed by concentrating the separated and recovered target double-stranded nucleic acid molecules (fourth embodiment of invention).

A second method is one wherein a sample containing non-target double-stranded nucleic acid molecules (6), a second PI polyamide (7) modified with a second linker molecule (8) are mixed to form a complex b1, which is further mixed with a carrier b (10) modified with a second ligand molecule (9) to form a complex B (200), followed by removing the complex B (200) and concentrating the separated and recovered target double-stranded nucleic acid molecules (1) (fifth embodiment of invention).

A third method is one wherein a second PI polyamide (7) modified with a second linker molecule (8) and a carrier b (10) modified with a second ligand molecule (9) are mixed to form a complex b2, which is further mixed with non-target double-stranded nucleic acid molecules (6) to form a complex B (200), followed by removing the complex B (200) and concentrating the separated and recovered target double-stranded nucleic acid molecules (1) (sixth embodiment of invention).

It will be noted that the complex of FIG. 3B is indicated as "complex B (200)" including "complex b1" and "complex b2". Here, a complex wherein the non-target double-stranded nucleic acid molecule (6) and the second PI polyamide (7) modified with the second linker molecule (8) are bound together is defined as "complex b1". A complex wherein the second PI polyamide (7) and the carrier b (10) modified with the ligand molecule capable of specifically binding to the second linker molecule (8) are bound is defined as "complex b2". A complex wherein the complex b1 and the complex b2 are bound through the interaction between the second linker molecule (8) and the ligand molecule (9) capable of specifically binding to the second linker molecule is defined as "complex B".

As shown in FIGS. 2B and 3B, the second PI polyamide (7) is modified with linker molecule (8) (e.g., biotin), and the carrier b (10) is modified with the second ligand molecule (9) (e.g., streptavidin) capable of specifically binding to the second linker molecule (8). The second PI polyamide (8) is able to specifically bind to the non-target double-stranded nucleic acid molecule (9).

The thus formed complex B (200) is separated and removed, followed by recovering the target double-stranded nucleic acid molecules (1) and subjecting to analyses. Although depending on the type of material for the carrier b (10) used, the method of separating and removing the formed complex B may be one wherein the complex B is pulled by use of a magnet and thus the complex B (200) can be removed in the case that the carrier b (10) is made of a magnetic body. Where the carrier b (10) is in the form of particles or a gel, the complex B can be removed by pipetting or decantation after centrifugal separation. More specific conditions of the mixing methods, the formation methods of the respective complexes and the separation methods are described hereinafter in the present specification.

In some embodiments, the method of recovering and concentrating the target double-stranded nucleic acid molecules (1) can be performed by mixing, from the start, both a first PI polyamide (2) modified with a second linker molecule (3) and a second PI polyamide (7) modified with a second linker molecule (8) with a sample containing target double-stranded nucleic acid molecules (1) and non-target double-stranded nucleic acid molecules (6), further mixing with a carrier a (5) modified with a second ligand molecule (4) to form a complex A (100), and concentrating the target double-stranded nucleic acid molecules (1) by separation and recovery of the complex A (100) (seventh embodiment of invention).

In another embodiment, target double-stranded nucleic acid molecules can be concentrated by mixing, from the start, both a first PI polyamide (2) modified with a first linker molecule (3) and a second PI polyamide (7) modified with a second molecule (8) with a sample containing target double-stranded nucleic acid molecules (1) and non-target double-stranded nucleic acid molecules (6) and further mixing with a carrier b (10) modified with a second ligand molecule (9) to form a complex B (200), followed by the removing step of the complex B (200) to form a complex A (100) (eighth embodiment of invention).

In a further embodiment, target double-stranded nucleic acid molecules (1) can be concentrated by mixing, from the start, both a first PI polyamide (2) modified with a first linker molecule (3) and a second PI polyamide (7) modified with a second molecule (8), a carrier a (5) modified with a second linker molecule (8), and a carrier b (10) modified with a first ligand molecule (4) with a sample containing the target double-stranded nucleic acid molecules (1) and non-target double-stranded nucleic acid molecules (6) to form a complex A and a complex B (200), followed by removing the complex B (200) and subsequently separating and recovering the complex A (100) (ninth embodiment of invention).

In a still further embodiment, target double-stranded nucleic acid molecules (1) can be concentrated by a procedure including, as a first step, either mixing a first PI polyamide (2) with an a sample containing target double-stranded nucleic acid molecules (1) and non-target double-stranded nucleic acid molecules (2) to from a complex a1, further mixing with a carrier a (5) modified with a first ligand (4) to form a complex A (100), or mixing a first PI polyamide (2) with a carrier a (5) modified with a first ligand molecule (4) to form a complex a2 and further mixing with a sample containing target double-stranded nucleic acid molecules (1) and non-target double-stranded nucleic acid molecules (6) to form a complex A (100), as second step, either further mixing with a second PI polyamide (7) modified with a second linker molecule (8) to form a complex b1 and then mixing with a carrier b (10) modified with a second ligand molecule (9) to form a complex B (200), or mixing with a carrier b (10) modified with a second ligand molecule (9) to form a complex b2 and subsequently mixing with a second PI polyamide (7) modified with a second linker molecule (8) to form a complex B (200), and as a third step, separating and recovering the complex A (100) after through a step of removing the complex B thereby concentrating the target double-stranded nucleic acid molecules (1) (tenth embodiment of invention).

The first, third and ninth embodiments of invention described above enable the concentration of the target double-stranded nucleic acid molecules according to less steps in a simple manner. Moreover, the eighth to tenth embodiments of invention enable an improved concentration efficiency of target double-stranded nucleic acid molecules by forming the complex B after simultaneous or previous removal from the sample.

Furthermore, a proper combination of such three methods of recovering and concentrating the target double-stranded nucleic acid molecules as set out above and the method of concentrating the target double-stranded nucleic acid molecules (1) through the recovery and removal of the non-target double-stranded nucleic acid molecules (1) enables further concentration of the target double-stranded nucleic acid molecules (1).

The above-stated ten embodiments of invention related to the present application are further described below. In the following description, such a case is presented, where a first or second linker molecule (3, 8) is made of biotin, a first or second ligand (4, 9) is made of streptavidin, and a carrier a (5) and a carrier b (10) are each made of a magnetic body.

In this regard, however, in the ninth and tenth embodiments of invention, the types of materials for the linker molecule and ligand molecule are so selected that target double-stranded nucleic acid molecule and the non-target double-stranded nucleic acid molecules can independently bind to the carrier a and the carrier b, respectively. Moreover, as to the carrier a and the carrier b, their types of materials should be so selected as to permit the complex A and the complex B to be independently separated or recovered.

The first embodiment of invention is directed to a method for concentrating target double-stranded nucleic acid molecules from a sample containing the target double-stranded nucleic acid molecules and non-target nucleic acid molecules while separating from the non-target nucleic acid molecules (FIG. 4), the method for the concentration under separation of the target nucleic acid from the non-target double-stranded nucleic acid molecules, characterized by comprising:

(step 1) the step of mixing the sample, a pyrrole-imidazole-containing polyamide (first PI polyamide) modified with a first linker molecule and capable of specifically binding to a specific sequence of the target double-stranded nucleic acid molecule and a carrier a modified with a first ligand capable of specifically adsorbing and/or binding to the first linker molecule to provide a mixed solution (S402 in FIG. 4);

(step 2) the step of forming a complex A wherein the carrier a is bound to the first PI polyamide of a complex a1 formed by binding between the target double-stranded nucleic acid molecule and the first PI polyamide in the mixed solution (S404 in FIG. 4); and (step 3): the step of separating and recovering the complex A from the mixed solution (S406 in FIG. 4).

Next, the respective steps of the first embodiment of invention are illustrated.

(Step 1)

The step 1 of mixing the sample with the first PI polyamide and the carrier a should be carried out in a reaction container that is not able to adsorb the target double-stranded nucleic acid molecules and the like thereon. This is because if a nucleic acid and the like are adsorbed on inside of the reaction container, some difficulty is involved in recovering the target double-stranded nucleic acid molecules.

The mixing temperature in the step 1 can be set at 25° C. to 100° C. The temperature can be preferably at 25° C. to 80° C., more preferably at 25° C. to 50° C. and much more preferably at 25° C. to 40° C.

The amount ratio (number of molecules) of the first PI polyamide to the total double-stranded nucleic acid molecules in the sample mixed in the step 1 is at $1:10^2$ to $1:10^8$, preferably at $1:10^4$ to $1:10^8$, more preferably at $1:10^6$ to $1:10^8$, and much more preferably at $1:10^7$ to $1:10^8$.

The amount of the carrier mixed in the step 1 is preferably one sufficient to adequately recover the first PI polyamide formed in the mixed solution. For example, the amount ratio (number of molecules) of the ligand molecules on the carrier relative to the first PI polyamide is at 1:1 to 1:10, preferably 1:1 to 1:8, more preferably at 1:1 to 1:5 and much more preferably at 1:1 to 1:3.

In one embodiment of the present invention, it may be particularly preferred that the mixed solution in the step 1 is not contained with a pH buffer agent, a surfactant, a monovalent and/or divalent salt and the like described hereinbelow. In another embodiment of the invention, such a pH buffer agent, a surfactant, a monovalent and/or divalent salt and the like described hereinbelow may be contained arbitrarily and selectively.

The amount of a surfactant which can be contained in the mixed solution in the step 1 can be at not larger than 0.05 v/v % of the total mixed solution, preferably at 0.03 v/v %, more preferably at 0.01 v/v %. It will be noted that v/v is volume ratio and v/v % means volume/volume percent.

The amount of a pH buffer agent which can be contained in the mixed solution in the step 1 can be set at 100 mM, preferably at 50 mM, more preferably at 20 mM and much more preferably at 10 mM.

The salt that can be contained in the mixed solution in the step 1 can be set at not larger than 1.0 M, preferably not larger than 0.5 M and more preferably at not larger than 0.2 M.

(Step 2)

The time required for the formation of the complex A in the step 2 is within 24 hours, preferably from 1 hour to 12 hours, more preferably from 1 hour to 6 hours and much more preferably from 1 to 3 hours.

The temperature required for the formation of the complex A in the step 2 can be at 25° C. to 100° C., preferably at 25° C. to 80° C., more preferably at 25° C. to 50° C. and much more preferably at 25° C. to 40° C.

(Step 3)

In the step 3, the carrier 1 is made of a magnetic body, so that the complex A is pulled towards the wall surface of a reaction container by means of a magnet and the resulting supernatant liquid can be removed from the reaction container by decantation or pipetting.

The complex A recovered in the step 3 may be suspended in a buffer solution or the like so as to subject it to subsequent analyses. The analysis method of the target double-stranded nucleic acid molecules in the complex A is described hereinafter in the present specification.

Figure 5:
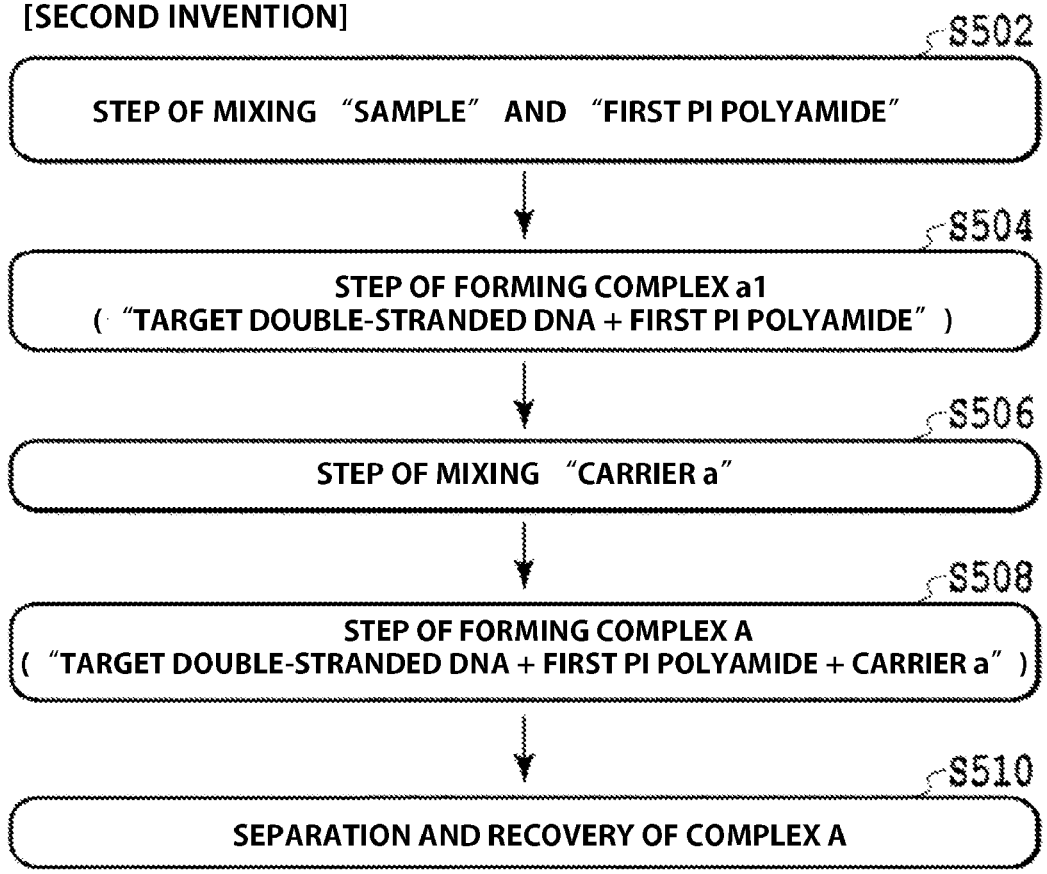
FIG. 5 is a flow chart of a second embodiment of the invention in the present specification.

The second embodiment of invention is directed to a method (FIG. 5) for concentrating target double-stranded nucleic acid molecules from a sample containing the target double-stranded nucleic acid molecules and non-target double-stranded nucleic acid molecules while separating from the non-target double-stranded nucleic acid molecules, the method for concentrating the target nucleic acid under separation from the non-target double-stranded nucleic molecules, characterized by comprising:

(step 1) the step of mixing the sample with a pyrrole-imidazole-containing polyamide (first PI polyamide) modified with a first linker molecule and capable of specifically binding to a specific sequence of the target double-stranded nucleic molecule to provide a mixed solution 1 (S502 in FIG. 5);

(step 2) the step of forming a complex a1 in the mixed solution 1 wherein the target double-stranded nucleic molecule and the first PI polyamide are bound together (S504 in FIG. 5);

step (3) the step of mixing, with the mixed solution, a carrier a modified with a first ligand molecule capable of specifically binding and/or adsorbing to the first linker molecule to provide a mixed solution 2 (S506 in FIG. 5);

(Step 4) the step of forming a complex A in the mixed solution wherein the first PI polyamide of the complex a1 and the carrier a are bound together (S508 in FIG. 5); and (step 5) the step of recovering the complex A by separation from the mixed solution 2 (S510 in FIG. 5).

Next, the respective steps of the second embodiment of invention are described.

(Step 1)

The step 1 of mixing the sample 1 with the first PI polyamide should be carried out in a reaction container that is not able to adsorb the target double-stranded nucleic acid molecules and the like thereon. This is because if a nucleic acid and the like are adsorbed on inside of the reaction container, some difficulty is involved in recovering the target double-stranded nucleic acid molecules.

The mixing temperature in the step 1 can be set at 25° C. to 100° C., preferably at 25° C. to 80° C., more preferably at 25° C. to 50° C. and much more preferably at 25° C. to 40° C.

The amount ratio (number of molecules) of the first PI polyamide to the total double-stranded nucleic acid molecules in the sample mixed in the step 1 is at $1:10^2$ to $1:10^8$, preferably at $1:10^4$ to $1:10^8$, more preferably at $1:10^6$ to $1:10^8$, and much more preferably at $1:10^7$ to $1:10^8$.

In one embodiment of this invention, it may be particularly preferred that the mixed solution in the step 1 is not contained with a pH buffer agent, a surfactant, a monovalent and/or divalent salt and the like as described hereinbelow. In another embodiment of the invention, such a pH buffer agent, a surfactant, a monovalent and/or divalent salt and the like as described hereinbelow may be contained arbitrarily and selectively.

The amount of the surfactant which can be contained in the mixed solution in the step 1 can be at not larger than 0.05 v/v % of the total mixed solution, preferably at 0.03 v/v %, more preferably at 0.01 v/v %.

The amount of the pH buffer agent which can be contained in the mixed solution in the step 1 can be set at not larger than 100 mM, preferably at 50 mM, more preferably at 20 mM and much more preferably at 10 mM.

The salt that can be contained in the mixed solution in the step 1 can be set at not larger than 1.0 M, preferably not larger than 0.5 M and more preferably at not larger than 0.2 M.

(Step 2)

The time required for the formation of the complex a1 in the step 2 is within 60 minutes, preferably within 40 minutes, more preferably within 30 minutes and much more preferably within 10 minutes.

The temperature required for the formation of the complex a1 in the step 2 can be set at 25° C. to 100° C., preferably at 25° C. to 80° C., more preferably at 25° C. to 50° C. and much more preferably at 25° C. to 40° C.

(Step 3)

In the step 3, the amount of the carrier mixed in the step 3 is preferably one that is sufficient to satisfactorily recover the complex a1 formed in the mixed solution. For example, the amount ratio between the target double-stranded nucleic acid molecules and the ligand molecules on the carrier can be at 1:1 or over.

The temperature for mixing the carrier a in the step 3 can be set at 25° C. to 100° C., preferably at 25° C. to 80° C., more preferably at 25° C. to 50° C. and much more preferably at 25° C. to 40° C.

(Step 4)

The step 4 of the second embodiment of invention can be applied with such conditions as of the method of the step 2 of the first embodiment of invention.

(Step 5)

The step 5 of the second embodiment of invention can be applied with such conditions as of the method of the step 3 of the first embodiment of invention.

The complex A recovered in the step 5 may be suspended in a buffer solution or the like so as to subject it to subsequent analyses. The analysis method of the target double-stranded nucleic acid molecules in the complex A is described hereinafter in the specification.

Figure 6:
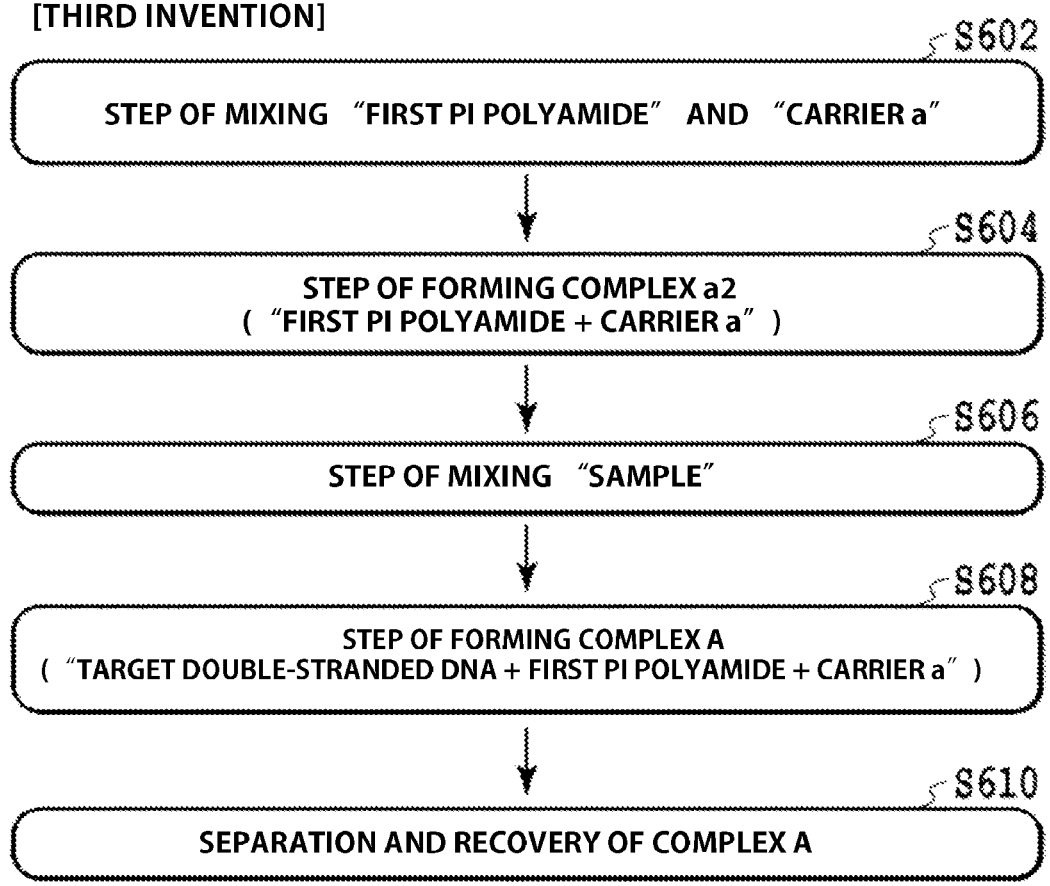
FIG. 6 is a flow chart of a third embodiment of the invention in the present specification.

The third embodiment of invention is directed to a method (FIG. 6) for concentrating target double-stranded nucleic acid molecules from a sample containing the target double-stranded nucleic acid molecules and non-target double-stranded nucleic acid molecules while separating from the non-target double-stranded nucleic acid molecules and to the method for concentrating the target nucleic acid while separating from the non-target double-stranded nucleic molecules, characterized by comprising:

(step 1) the step of mixing a pyrrole-imidazole-containing polyamide (first PI polyamide) modified with a first linker molecule and capable of specifically binding to a specific sequence of the target double-stranded nucleic molecule, a carrier a modified with a first ligand molecule capable of specifically binding and/or adsorbing to the first linker molecule, and a solution or a solvent to provide a mixed solution 1 (S602 in FIG. 6);

(step 2) the step of forming a complex a2 in the mixed solution 1 wherein the first PI polyamide and the carrier a are bound together (S604 in FIG. 6);

(step 3) the step of mixing the sample with the mixed solution 1 to provide a mixed solution 2 (S606 in FIG. 6);

(Step 4) the step of forming a complex A in the mixed solution 2 wherein the first PI polyamide of the complex a2 and the target double-stranded nucleic acid molecule are bound together (S608 in FIG. 6); and (step 5) the step of recovering the complex A by separation from the mixed solution 2 (S610 in FIG. 6).

Next, the respective steps of the third embodiment of invention will be described.

(Step 1)

The third embodiment of invention should be carried out in a reaction container that is not able to adsorb the target double-stranded nucleic acid molecules and the like thereon. This is because if a nucleic acid and the like are adsorbed on inside of the reaction container, some difficulty is involved in recovering the target double-stranded nucleic acid molecules.

The amount of the carrier mixed in the step 1 is preferably one sufficient to satisfactorily recover the first PI polyamide formed in the mixed solution. For example, the amount ratio between the target double-stranded nucleic acid molecules and the ligand molecules on the carrier can be set at 1:1 or over.

The mixing temperature in the step 1 can be set at 25° C. to 100° C., preferably at 25° C. to 80° C., more preferably at 25° C. to 50° C. and much more preferably at 25° C. to 40° C.

In one embodiment of this invention, it may be particularly preferred that the mixed solution in the step 1 is not contained with a pH buffer agent, a surfactant, a monovalent and/or divalent salt and the like described hereinbelow. In another embodiment of the invention, such a pH buffer agent, a surfactant, a monovalent and/or divalent salt and the like as described hereinbelow may be contained arbitrarily and selectively.

The amount of the surfactant which can be contained in the mixed solution in the step 1 can be at not larger than 0.05 v/v % of the total mixed solution, preferably at 0.03 v/v %, more preferably at 0.01 v/v %.

The amount of the pH buffer agent which can be contained in the mixed solution in the step 1 can be set at not larger than 100 mM, preferably at 50 mM, more preferably at 20 mM and much more preferably at 10 mM.

The salt that can be contained in the mixed solution in the step 1 can be set at not larger than 1.0 M, preferably not larger than 0.5 M and more preferably at not larger than 0.2 M.

(Step 2)

The time required for the formation of the complex a2 in the step 1 is within 24 hours, preferably from 1 to 12 hours, more preferably from 1 hour to 6 hours, and much more preferably from 1 hour to 3 hours.

The temperature required for the formation of the complex a2 in the step 2 can be set at 25° C. to 100° C., preferably at 25° C. to 80° C., more preferably at 25° C. to 50° C. and much more preferably at 25° C. to 40° C.

The amount ratio (number of molecules) of the first PI polyamide to the total double-stranded nucleic molecules in the sample mixed in the step 3 can be at $1:10^2$ to $1:10^8$, preferably at $1:10^4$ to $1:10^8$, more preferably at $1:10^6$ to $1:10^8$ and much more preferably at $1:10^7$ to $1:10^8$.

(Step 4)

The formation of the complex A in the step 4 can be within 60 minutes, preferably within 40 minutes, more preferably within 30 minutes and much more preferably within 10 minutes.

The temperature required for the formation of the complex A in the step 4 can be at 25° C. to 100° C., preferably at 25° C. to 80° C., more preferably at 25° C. to 50° C. and much more preferably at 25° C. to 40° C.

(Step 5)

In the step 5 of the third embodiment of invention, such conditions as of the method of the third step of the first embodiment of invention can be applied.

The complex recovered in the step 5 may be suspended in a buffer solution so as to subject it to subsequent analyses. The analysis method of the target double-stranded nucleic acid molecules in the complex A is described hereinafter in the present specification.

Figure 7:
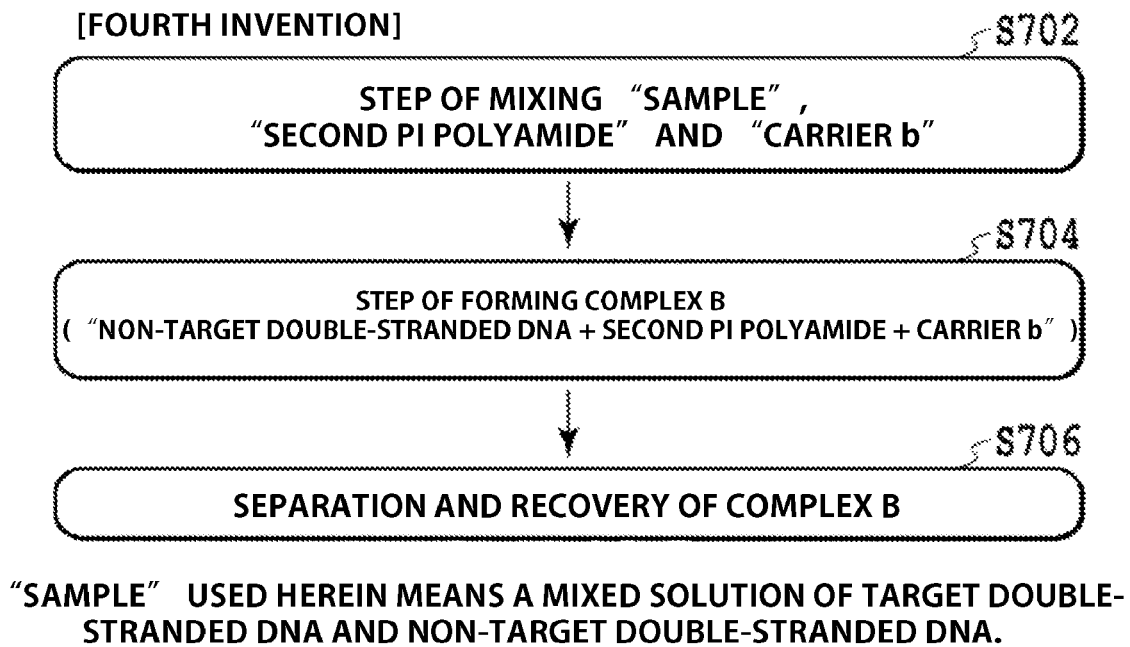
FIG. 7 is a flow chart of a fourth embodiment of the invention in the present specification.

The fourth embodiment of invention is directed to a method (FIG. 7) for removing non-target double-stranded nucleic acid molecules by separation from a sample containing target double-stranded nucleic acid molecules and the non-target double-stranded nucleic acid molecules and to the method for removing the non-target nucleic acid by separation, characterized by comprising:

(step 1) the step of mixing the sample, a pyrrole-imidazole-containing polyamide (second PI polyamide) modified with a second linker molecule and capable of specifically binding to a specific sequence of the non-target double-stranded nucleic acid molecule and a carrier b modified with a second ligand molecule capable of specifically binding and/or adsorbing to the second linker molecule to provide a mixed solution (S702 in FIG. 7);

(step 2) the step of forming a complex B by further binding the carrier b to the second PI polyamide of the complex b1 in the mixed solution wherein the non-target double-stranded nucleic acid molecule and the second PI polyamide are bound together (S704 in FIG. 7); and (step 3) the step of removing the complex B by separation from the mixed solution (S706 in FIG. 7).

Next, the respective steps of the fourth embodiment of invention will be described.

(Step 1)

The step 1 of the fourth embodiment of invention can be applied with the same conditions as of the procedure of the step 1 of the first embodiment of invention described before, except that the second PI polyamide is used in place of the first PI polyamide.

(Step 2)

The step 2 of the fourth embodiment of invention can be applied with the same conditions as of the procedure of the step 1 of the first embodiment of invention described before, except that the second PI polyamide is used in place of the first PI polyamide.

(Step 3)

In the step 3 of the fourth embodiment of invention, the carrier is made of a magnetic body, so that the complex B is pulled towards the wall surface of the reaction container by a magnet and can be removed by recovering a supernatant liquid from the reaction by decantation or pipetting.

The supernatant liquid containing the complex A recovered in the step 3 can be subjected to subsequent analyses as it is. In the same manner as in the first embodiment of invention, the complex A in the supernatant liquid may be further concentrated.

The analysis method of the target double-stranded nucleic acid molecules in the thus recovered complex A is described hereinafter in the present specification.

Figure 8:
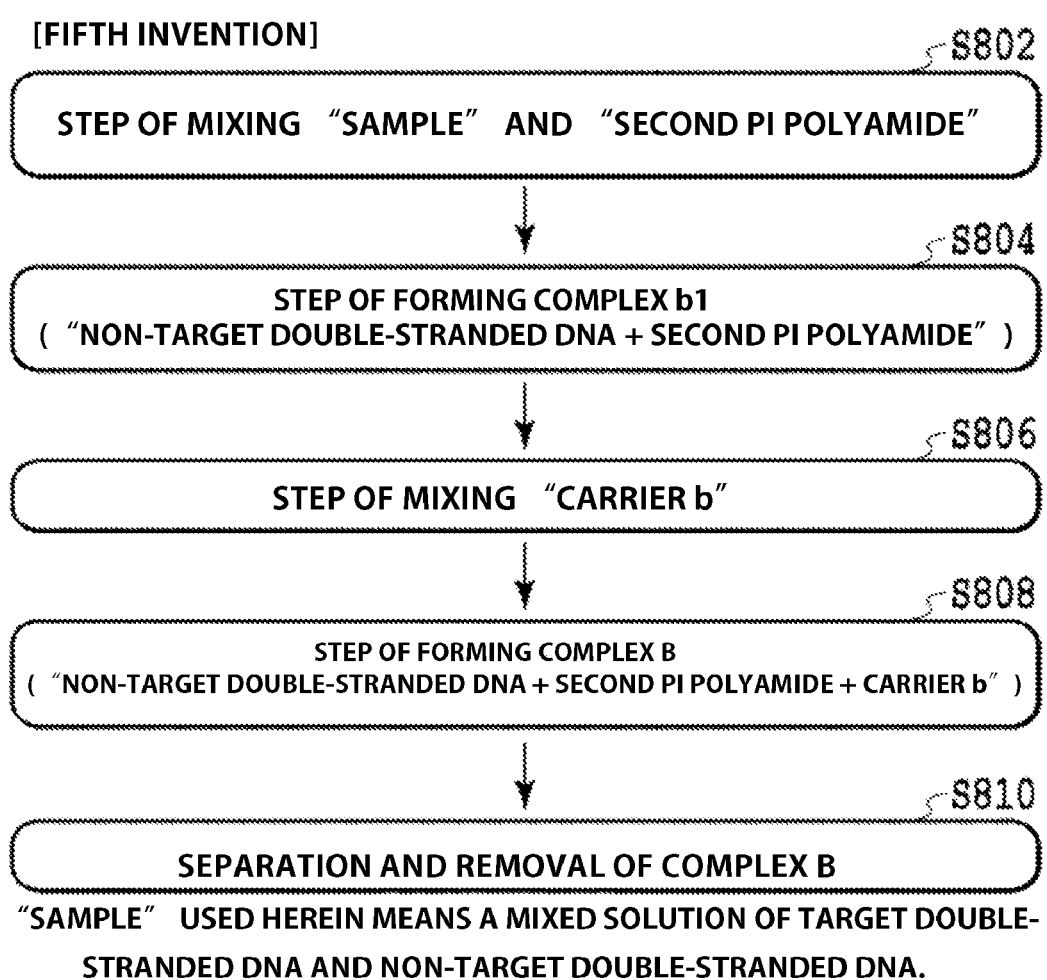
FIG. 8 is a flow chart of a fifth embodiment of the invention in the present specification.

The fifth embodiment of invention is directed to a method for removing non-target double-stranded nucleic acid molecules by separation from a sample containing target double-stranded nucleic acid molecules and the non-target double-stranded nucleic acid molecules (FIG. 8) and to the method for removing a non-target nucleic acid by separation, characterized by comprising:

(step 1) the step of mixing the sample, a pyrrole-imidazole-containing polyamide (second PI polyamide) modified with a second linker molecule and capable of specifically binding to a specific sequence of the non-target double-stranded nucleic acid molecules to provide a mixed solution 1 (S802 in FIG. 8);

(step 2) the step of forming the complex b1 in the mixed solution 1 wherein the non-target double-stranded nucleic acid molecule and the second Pi polyamide are bound together (S804 in FIG. 8);

(step 3) the step of mixing a carrier b modified with a second ligand molecule capable specifically binding and/or adsorbing to the second linker molecule with the mixed solution 1 to provide a mixed solution 2 (S806 in FIG. 8);

(step 4) the step of forming a complex B in the mixed solution 2 wherein the second PI polyamide of the complex b1 and the carrier b are bound together (S808 in FIG. 8); and (step 5) the step of removing the complex B by separation from the mixed solution 2 (S810 in FIG. 8).

Next, the respective steps of the fifth invention will be described.

(Step 1)

The step 1 of the fifth embodiment of invention can be applied with the same conditions as of the procedure of the step 1 of the second embodiment of invention, except that the second PI polyamide is used in place of the first PI polyamide.

(Step 2)

The step 2 of the fifth embodiment of invention can be applied with the same conditions as of the procedure of the step 2 of the second embodiment of invention, except that the second PI polyamide is used in place of the first PI polyamide.

(Step 3)

The step 3 of the fifth embodiment of invention can be applied with the same conditions as of the procedure of the step 3 of the second embodiment of invention, except that the second PI polyamide is used in place of the first PI polyamide and the carrier b is used instead of the carrier a.

(Step 4)

The step 4 of the fifth embodiment of invention can be applied with the same conditions as of the procedure of the step 4 of the second embodiment of invention, except that the second PI polyamide is used in place of the first PI polyamide and the carrier b is used instead of the carrier a.

(Step 5)

The step 5 of the fifth embodiment of invention can be applied with the same conditions as of the step 5 of the fourth embodiment of invention.

The analysis method of the target double-stranded nucleic acid molecules in the recovered complex A is described hereinafter in this specification.

Figure 9:
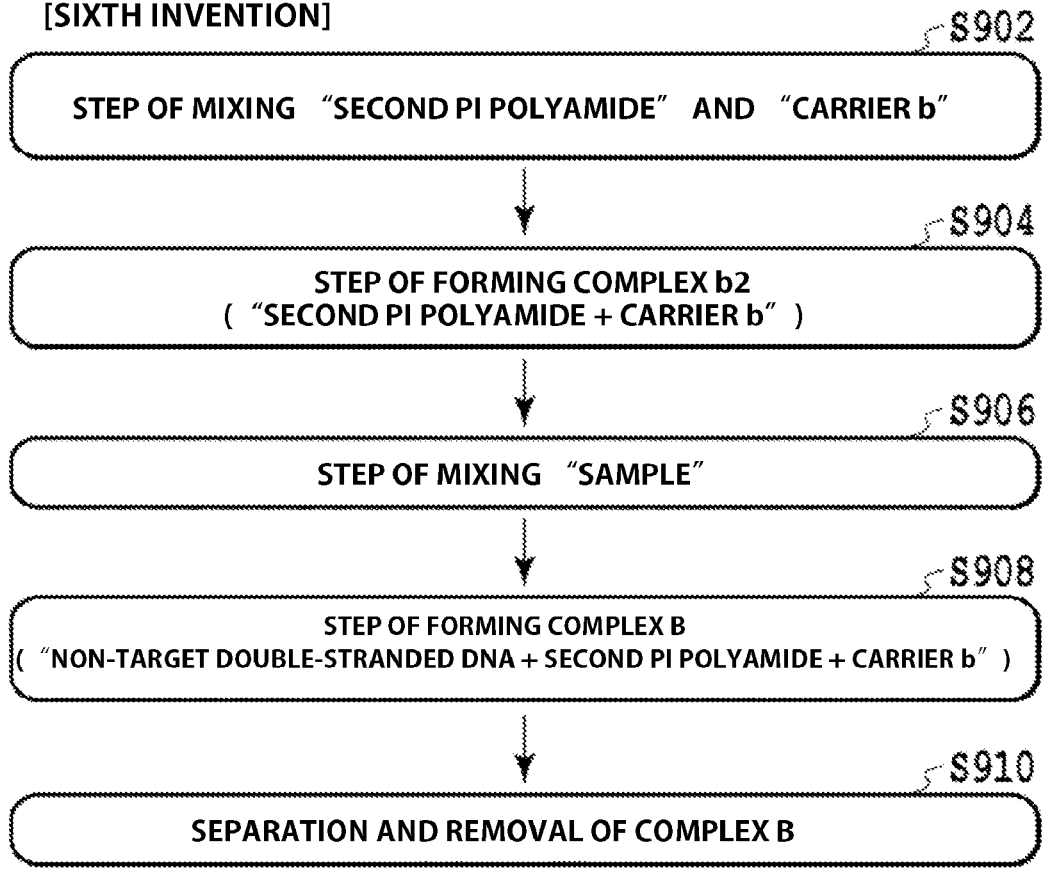
FIG. 9 is a flow chart of a sixth embodiment of the invention in the present specification.

The sixth embodiment of invention is directed to a method for removing non-target double-stranded nucleic acid molecules by separation from a sample containing target double-stranded nucleic acid molecules and the non-target double-stranded nucleic acid molecules (FIG. 9) and to the method for removing the non-target double-stranded nucleic acid by separation, characterized by comprising:

(step 1) the step of mixing a pyrrole-imidazole-containing polyamide (second PI polyamide) modified with a second linker molecule and capable of specifically binding to a specific sequence of the non-target double-stranded nucleic acid molecule and a carrier b modified with a second ligand molecule capable of specifically binding and/or adsorbing to the second linker molecule to provide a mixed solution 1 (S902 in FIG. 9);

(step 2) the step of forming a complex b2 by binding between the second PI polyamide and the carrier b in the mixed solution 1 (S904 in FIG. 9);

(step 3) the step of mixing the sample with the mixed solution 1 to provide a mixed solution 2 (S906 in FIG. 9);

(step 4) the step of forming a complex B by binding between the complex b2 and the non-target double-stranded nucleic acid molecule in the mixed solution (S908 in FIG. 9); and (step 5) the step of removing the complex B by separation from the mixed solution 2 (S910 in FIG. 9).

Next, the respective steps of the sixth embodiment of invention will be described.

The sixth embodiment of invention is directed to a method for removing non-target double-stranded nucleic acid molecules by separation form a sample containing target double-stranded nucleic acid molecules and the non-target double-stranded nucleic acid molecules, with the following steps.

(Step 1)

The step 1 of the sixth embodiment of invention can be applied with such conditions as of the procedure of the step 1 of the third embodiment of invention described hereinbefore, except that a second PI polyamide is used in place of the first PI polyamide and a carrier b is used in place of the carrier a.

The step 2 of the sixth embodiment of invention can be applied with such conditions as of the procedure of the step 2 of the third embodiment of invention described hereinbefore, except that the second PI polyamide is used in place of the first PI polyamide and the carrier b is used in place of the carrier a.

The step 3 of the sixth embodiment of invention can be applied with such conditions as of the procedure of the step 3 of the third embodiment of invention described hereinbefore, except that the second PI polyamide is used in place of the first PI polyamide and the carrier b is used in place of the carrier a.

(Step 4)

The step 4 of the sixth embodiment of invention can be applied with such conditions as of the procedure of the step 4 of the third embodiment of invention described hereinbefore, except that the second PI polyamide is used in place of the first PI polyamide and the carrier b is used in place of the carrier a.

(Step 5)

The step 5 of the sixth embodiment of invention can be applied with such conditions as of the procedure of the step 5 of the third embodiment of invention described hereinbefore, except that the second PI polyamide is used in place of the first PI polyamide and the carrier b is used in place of the carrier a.

The analysis method for the target double-stranded nucleic acid molecules of the recovered complex A is described hereinafter in the present specification.

Figure 10:
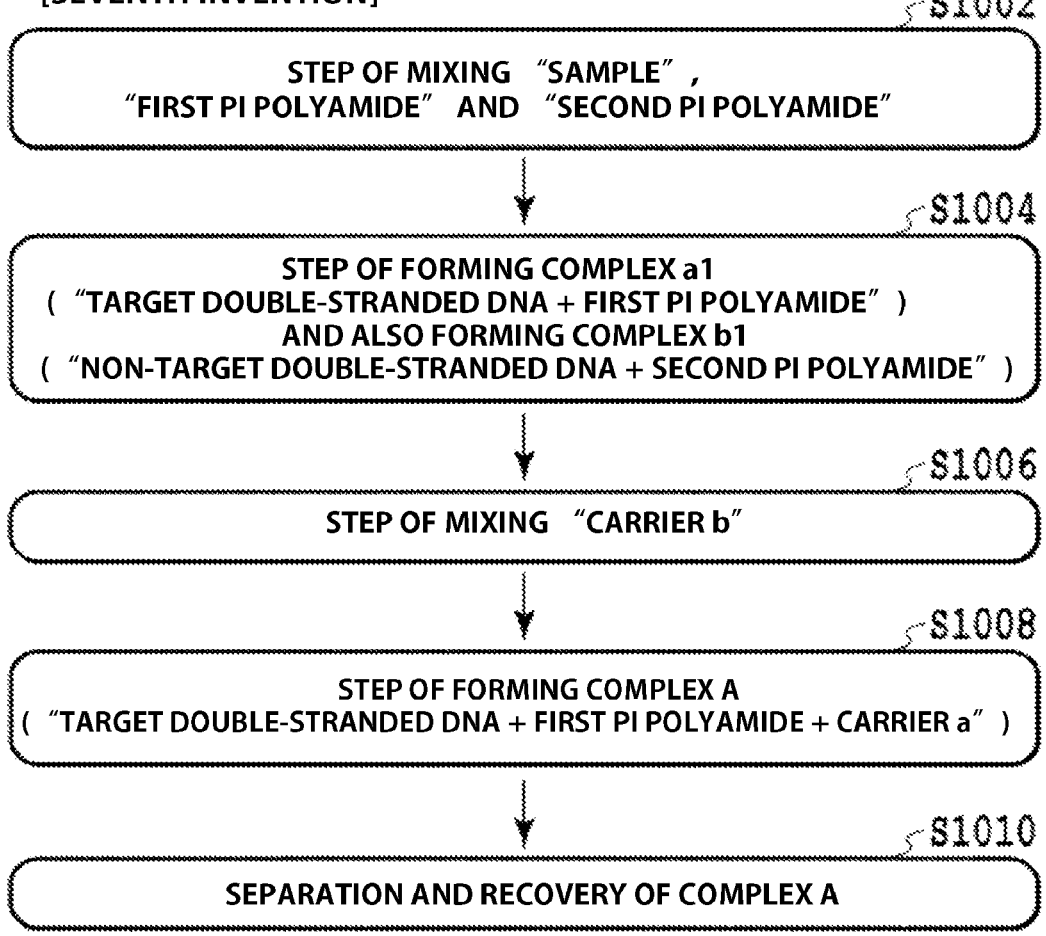
FIG. 10 is a flow chart of a seventh embodiment of the invention in the present specification.

The seventh embodiment of invention is directed to a method for concentrating target double-stranded nucleic acid molecules from a sample containing the target double-stranded nucleic acid molecules and non-target double-stranded nucleic acid molecules while separating from the non-target double-stranded nucleic acid molecules (FIG. 10) and to the method for concentrating the target nucleic acid under separation from the non-target double-stranded nucleic acid molecules, characterized by comprising the steps of:

(step 1) mixing the sample, a pyrrole-imidazole-containing polyamide (first PI polyamide) modified with a first linker molecule and capable of specifically binding to a specific sequence of the target double-stranded nucleic acid molecule, and a pyrrole-imidazole-containing polyamide (second PI polyamide) modified with a second linker molecule and capable of specifically binding to a specific sequence of the non-target double-stranded nucleic acid molecule to provide a mixed solution 1 (S1002 in FIG. 10);

(step 2) forming a complex a1 wherein the target double-stranded nucleic acid molecule and the first PI polyamide are bound together in the mixed solution and also a complex b1 wherein the non-target double-stranded nucleic acid molecule and the second PI polyamide are bound together in the mixed solution (S1004 in FIG. 10);

(step 3) mixing, with the mixed solution, a carrier a modified with a first ligand molecule capable specifically binding and/or adsorbing the first linker molecule to provide a mixed solution 2 (S1006 in FIG. 10);

(step 4) forming a complex A in the mixed solution 2 wherein the first PI polyamide of the complex a1 and the carrier a are bound together (S1008 in FIG. 10); and (step 5) recovering the complex A by separation from the mixed solution 2 (S1010 in FIG. 10).

Next, the respective steps of the seventh embodiment of invention will be described.

(Step 1)

The step 1 of the seventh embodiment of invention can be applied with the same conditions as of the step 1 of the first embodiment of invention, except that both the first PI polyamide and the second PI polyamide are mixed together.

The amount ratio (the number of molecules) of the first PI polyamide to the total double-stranded nucleic acid molecules in the sample mixed in the step 1 can be at $1:10^2$ to $1:10^8$, preferably at $1:10^4$ to $1:10^8$, more preferably at $1:10^6$ to $1:10^8$, and much more preferably at $1:10^7$ to $1:10^8$.

The amount ratio (the number of molecules) of the second PI polyamide to the total double-stranded nucleic acid molecules in the sample mixed in the step 1 can be at $1:10^2$ to $1:10^8$, preferably at $1:10^4$ to $1:10^8$, more preferably at $1:10^6$ to $1:10^8$, and much more preferably at $1:10^7$ to $1:10^8$.

(Step 2)

The step 2 of the seventh embodiment of invention can be applied with the same conditions as of the step 2 of the second embodiment of invention.

(Step 3)

The step 3 of the seventh embodiment of invention can be applied with the same conditions as of the step 3 of the second embodiment of invention.

(Step 4)

The step 4 of the seventh embodiment of invention can be applied with the same conditions as of the step 4 of the second embodiment of invention.

(Step 5)

The step 5 of the seventh embodiment of invention can be applied with the same conditions as of the step 5 of the second embodiment of invention.

Figure 11:
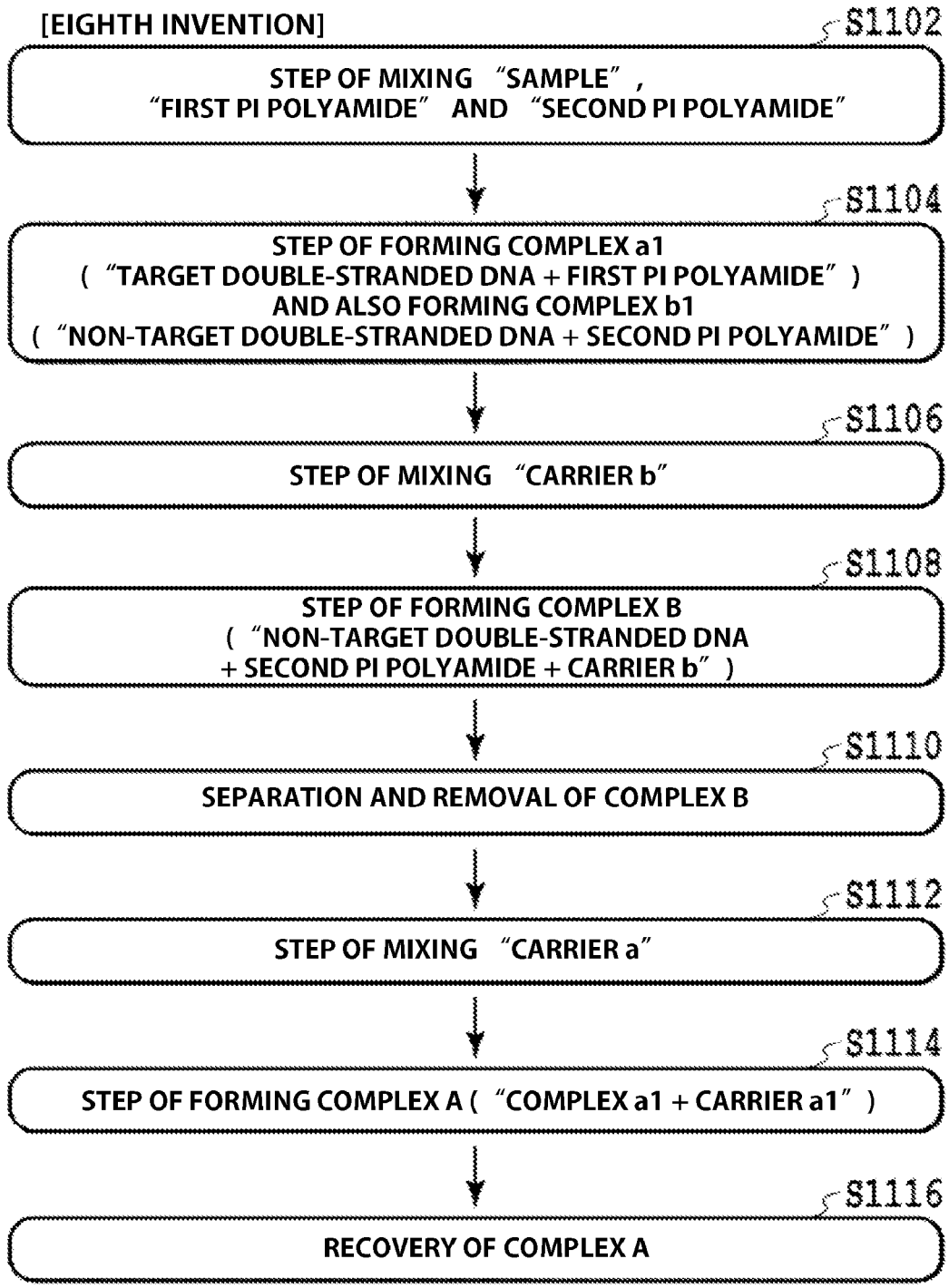
FIG. 11 is a flow chart of an eighth embodiment of the invention in the present specification.

The eighth embodiment of invention is directed to a method for separating non-target double-stranded nucleic acid molecules from a sample containing target double-stranded nucleic acid molecules and the non-target double-stranded nucleic acid molecules (FIG. 11) and to the method for separating and concentrating the non-target double-stranded nucleic acid molecules, characterized by comprising the steps of:

(step 1) mixing the sample, a pyrrole-imidazole-containing polyamide (first PI polyamide) modified with a first linker molecule and capable of specifically binding to a specific sequence of the target double-stranded nucleic acid molecule, and a pyrrole-imidazole-containing polyamide (second PI polyamide) modified with a second linker molecule and capable of specifically binding to a specific sequence of the non-target double-stranded nucleic acid molecule to provide a mixed solution 1 (S1102 in FIG. 11);

(step 2) forming a complex a1 wherein the target double-stranded nucleic acid molecule and the first PI polyamide are bound together in the mixed solution 1 and also forming a complex b1 wherein the non-target double-stranded nucleic acid molecule and the second PI polyamide are bound together in the mixed solution 1 (S1104 in FIG. 11);

(step 3) mixing, with the mixed solution 1, a carrier b modified with a second ligand molecule capable of specifically binding and/or adsorbing to the second linker molecule to provide a mixed solution 2 (S1106 in FIG. 11);

(step 4) forming a complex B in the mixed solution 2 wherein the second PI polyamide of the complex b1 and the carrier b are bound together (S1108 in FIG. 11);

(step 5) removing the complex B by separation from the mixed solution 2 (S1110 in FIG. 11);

(step 6) mixing, with the mixed solution 2 from which the complex B has been separated, a carrier a modified with a first ligand molecule capable of specifically binding and/or adsorbing to the first linker molecule (S1112 in FIG. 11);

(Step 7) forming a complex A wherein the complex a1 and the carrier a are bound together (S1114 in FIG. 11); and (step 8) recovering the complex A by separation from the mixed solution 3 (S1116 in FIG. 11).

Next, the respective steps of the eighth embodiment of invention will be described.

(Step 1)

The step 1 of the eighth embodiment of invention can be applied with the same conditions as of the step 1 of the fifth embodiment of invention, except that the first PI polyamide and the second PI polyamide are both mixed.

The amount ratio (the number of molecules) of the first polyamide to the total double-stranded nucleic acid molecules in the sample mixed in the step 1 can be at $1:10^2$ to $1:10^8$, preferably at $1:10^4$ to $1:10^8$, more preferably at $1:10^6$ to $1:10^8$, and much more preferably at $1:10^7$ to $1:10^8$.

The amount ratio (the number of molecules) of the second polyamide to the total double-stranded nucleic acid molecules in the sample mixed in the step 1 can be at $1:10^2$ to 1:10⁸, preferably at 1:10⁴ to 1:10⁸, more preferably at 1:10⁶ to 1:10⁸, and much more preferably at 1:10⁷ to 1:10⁸.

(Step 2)

The step 2 of the eighth embodiment of invention can be applied with the same conditions as of the step 2 of the fifth embodiment of invention.

(Step 3)

The step 3 of the eighth embodiment of invention can be applied with the same conditions as of the step 3 of the fifth embodiment of invention.

(Step 4)

The step 4 of the eighth embodiment of invention can be applied with the same conditions as of the step 4 of the fifth embodiment of invention.

(Step 5)

The step 5 of the eighth embodiment of invention can be applied with the same conditions as of the step 5 of the fifth embodiment of invention.

(Step 6)

The step 6 of the eighth embodiment of invention can be applied with the same conditions as of the step 3 of the second embodiment of invention.

(Step 7)

The step 7 of the eighth embodiment of invention can be applied with the same conditions as of the step 4 of the second embodiment of invention.

(Step 8)

The step 8 of the eighth embodiment of invention can be applied with the same conditions as of the step 5 of the second embodiment of invention.

Figure 12:
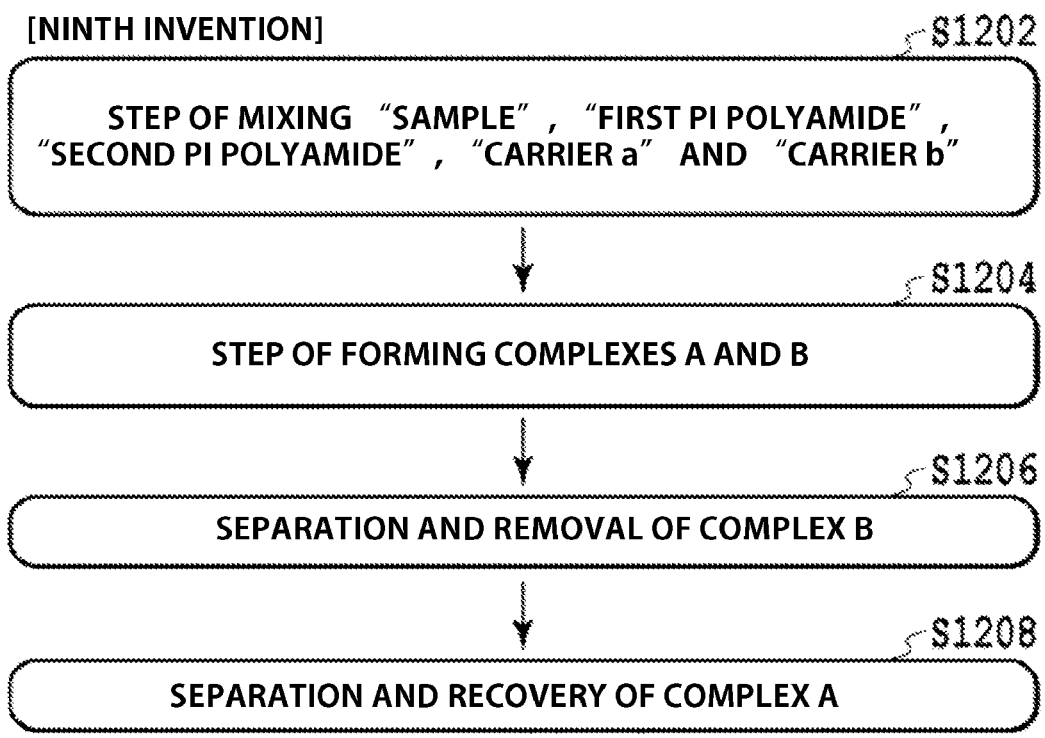
FIG. 12 is a flow chart of a ninth embodiment of the invention in the present specification.

The ninth embodiment of invention is directed to a method for concentrating a target nucleic acid while separating the target double-stranded nucleic acid molecules from a sample containing the target double-stranded nucleic acid molecules and non-target double-stranded molecules (FIG. 12) and to the method for concentrating the target nucleic acid under separation from the non-target double-stranded nucleic acid molecules, characterized by comprising the steps of:

(step 1) mixing the sample, a pyrrole-imidazole-containing polyamide modified with a first linker molecule and capable of specifically binding to a specific sequence of the target double-stranded nucleic acid molecule (first PI polyamide), a carrier a modified with a first ligand molecule capable of specifically binding and/or adsorbing to the first linker molecule.

a pyrrole-imidazole-containing polyamide modified with a second linker molecule and capable of specifically binding to a specific sequence of the non-target double-stranded nucleic acid molecule (second PI polyamide), and a carrier b modified with a second ligand molecule capable of specifically binding/or adsorbing to the second linker molecule thereby providing a mixed solution 1 (S1202 in FIG. 12);

(step 2) forming a complex A by binding the first PI polyamide of a complex a1, in which the target double-stranded nucleic acid molecule and the first PI polyamide are bound together in the mixed solution, further with the carrier a, and further forming a complex B by binding the second PI polyamide of a complex b1, in which the non-target double-stranded nucleic acid molecules and the second PI polyamide are bound together in the mixed solution, further with the carrier b (S1204 in FIG. 12;

(step 3) removing the complex B by separation from the mixed solution 1 (S1206 in FIG. 12); and (step 4) removing the complex A by separation from the mixed solution 1 (S1208 in FIG. 12).

Next, the respective steps of the ninth embodiment of invention are described.

(Step 1)

The step 1 of mixing the sample, the first PI polyamide, the second PI polyamide, the carrier a, and the carrier b needs to be carried out in a reaction container incapable of adsorbing the target double-stranded nucleic acid molecules and the like. This is because if a nucleic acid and the like are adsorbed to the container, difficulty is involved in recovering the target double stranded nucleic acid molecules.

The mixing temperature in the step 1 can be set at 25° C. to 100° C., preferably at 25° C. to 80° C., more preferably at 25° C. to 50° C. and much more preferably at 25° C. to 40° C.

The respective amount ratios (the numbers of molecules) of the first PI polyamide and the second PI polyamide to the total target double-stranded nucleic acid molecules and the total non-target double-stranded nucleic acid molecules are at 1:10² to 1:10⁸, preferably at 1:10⁴ to 1:10⁸, more preferably at 1:10⁶ to 1:10⁸ and much more preferably at 1:10⁷ to 1:10⁸.

The amount of the carriers a and b mixed in the step 1 should be, respectively, set at a level sufficient to satisfactorily recover the first PT polyamide and the second PI polyamide formed in the mixed solution. For example, the respective amount ratios (the number of molecules) of the ligand molecules on the carriers a and b to the first PI polyamide and the second PI polyamide are set at 1:1 to 1:10, more preferably 1:1 to 1:8, more preferably at 1:1 to 1:5 and much more preferably 1:1 to 1:3.

The carrier a and the carrier b used in the step 1 should be made of materials of the types that enable the complex A and the complex B subsequently formed together in the mixed solution to be separately isolated from each other.

In one embodiment of the present invention, it may be particularly preferred that the mixed solution in the step 1 is not contained with a pH buffer agent, a surfactant, a monovalent and/or divalent salt and the like as described hereinbelow. In another embodiment of the invention, such a pH buffer agent, a surfactant, a monovalent and/or divalent salt and the like as described hereinbelow may be contained arbitrarily and selectively.

The amount of the surfactant which can be contained in the mixed solution in the step 1 can be set at not larger than 0.05 v/v % of the total mixed solution, preferably at 0.03 v/v %, more preferably at 0.01 v/v %.

The amount of the pH buffer agent which can be contained in the mixed solution in the step 1 can be set at 100 mM, preferably at 50 mM, more preferably at 20 mM and much more preferably at 10 mM.

The salt that can be contained in the mixed solution in the step 1 can be set at not larger than 1.0 M, preferably not larger than 0.5 M and more preferably at not larger than 0.2 M.

(Step 2)

The times required for the formation of the complexes A and B in the step 2 can be, respectively, set within 24 hours, preferably from 1 hour to 12 hours, more preferably from 1 hour to 6 hours and much more preferably from 1 to 3 hours.

The temperatures required for the formation of the complexes A and B in the step 2 can be, respectively, set at 25° C. to 100° C., preferably at 25° C. to 80° C., more preferably at 25° C. to 50° C. and much more preferably at 25° C. to 40° C.

(Step 3)

The step 3 of the tenth embodiment of invention can be applied with the same conditions as of the step 3 of the second embodiment of invention. In this connection, however, if a material other than a magnetic body is used as a material for the carrier b, the complex B should be separated and removed according to a method suited for the characteristic properties of the carrier material.

(Step 4)

The step 4 of the tenth embodiment of invention can be applied with the same conditions as of the step 4 of the second embodiment of invention. In this connection, however, if a material other than a magnetic body is used as a material for the carrier b, the complex B should be separated and recovered according to a method suited for the characteristic properties of the carrier material.

The tenth embodiment of invention is directed to a method for concentrating a target nucleic acid from a sample containing target double-stranded nucleic acid molecules and non-target double-stranded nucleic acid molecules while separating from the target double-stranded nucleic acid molecules (FIG. 13) and to the method for concentrating the target nucleic acid under separation from the non-target double-stranded nucleic acid molecules, characterized by comprising the steps of:

(step 1) mixing the sample and a pyrrole-imidazole-containing polyamide (first PI polyamide) modified with a first linker molecule and capable of specifically binding to a specific sequence of the target double-stranded nucleic acid molecule to provide a mixed solution 1 (S1302 in FIG. 13), (step 2) forming a complex a1 in the mixed solution 1 wherein the target double-stranded nucleic acid molecules and the first PI polyamide are bound together (S1304 in FIG. 13), (step 3) mixing, with the mixed solution 1, a carrier a which is modified with a first ligand molecule and capable of binding and/or adsorbing to the first linker molecule to provide a mixed solution 2 (S1306 in FIG. 13), and (step 4) forming a complex A in the mixed solution 2 wherein the first PI polyamide of the complex a1 and the carrier a are bound together, or (step 1') mixing the sample, a pyrrole-imidazole-containing polyamide (first PI polyamide) modified with a first linker molecule and capable of specifically binding to a specific sequence of the target double-stranded nucleic acid molecule, a carrier modified with a first ligand molecule capable of specifically binding and/or adsorbing to the first linker molecule, and a solution or a solvent to provide a mixed solution 1' (S1322 in FIG. 13);

(step 2') forming a complex a2 in the mixed solution 1' wherein the first PI polyamide and the carrier a are bound together (S1324 in FIG. 13), (step 3') mixing the sample with the mixed solution 1' to provide a mixed solution 2' (S1326 in FIG. 13), and (step 4') forming a complex A in the mixed solution 2' wherein the first PI polyamide of the complex a2 and the target double-stranded nucleic acid molecule are bound together (S1328 in FIG. 13); and (step 5) mixing, with the mixed solution 2, a pyrrole-imidazole-containing polyamide (second PI polyamide) modified with a second linker molecule and capable of specifically binding to a specific sequence of the non-target double-stranded nucleic acid molecule after the (step 4) or the mixed solution 2' after the (step 4') to provide a mixed solution 3 (S1308 in FIG. 13), (step 6) forming a complex b1 in the mixed solution 3 wherein the non-target double-stranded nucleic acid molecule and the second PI polyamide are bound together (S1310 in FIG. 13), (step 7) mixing a carrier b modified with a second ligand molecule capable of specifically binding and/or adsorbing to the second linker molecule with the mixed solution 3 to provide a mixed solution 4 (S1312 in FIG. 13), (step 8) forming a complex B in the mixed solution 4 wherein the second PI polyamide of the complex b1 and the carrier b are bound together (S1314 in FIG. 13), (step 9) removing the complex B by separation from the mixed solution 4 (S1340 in FIG. 13); or (step 5') mixing, with the mixed solution 2 after the (step 4) or the mixed solution 2' after the (step 4'), a pyrrole-imidazole-containing polyamide (second PI polyamide) modified with a second linker molecule and capable of specifically binding to a specific sequence of the non-target double-stranded nucleic acid molecule, and a carrier b modified with a second ligand molecule capable of specifically binding and/or adsorbing to the second linker molecule to provide a mixed solution 3' (S1330 in FIG. 13), (step 6') forming a complex b2 in the mixed solution 3 wherein the non-target double-stranded nucleic acid molecules and the carrier b2 are bound together (S1332 in FIG. 13), (step 7') mixing the sample with the mixed solution 3' to provide a mixed solution 4' (S1334 in FIG. 13), (step 8') forming a complex B bound with the non-target double-stranded nucleic acid molecule in the mixed solution 4' (S1336 in FIG. 13), (step 9') removing the complex B by separation from the mixed solution 4' (S1340 in FIG. 13); and (step 10) recovering the complex A by separation from the mixed solution 4 after the (step 9) or the mixed solution 4' after the (step 9') (S1342 in FIG. 13).

Next, the respective steps of the tenth embodiment of invention will be described.

(Step 1)

The step 1 of the tenth embodiment of invention can be applied with the same conditions as of the step 1 of the second embodiment of invention.

(Step 2)

The step 2 of the tenth embodiment of invention can be applied with the same conditions as of the step 2 of the second embodiment of invention.

(Step 3)

The step 3 of the tenth embodiment of invention can be applied with the same conditions as of the step 3 of the second embodiment of invention.

(Step 4)

The step 4 of the tenth embodiment of invention can be applied with the same conditions as of the step 4 of the second embodiment of invention.

(Step 1')

The step 1' of the tenth embodiment of invention can be applied with the same conditions as of the step 1 of the third embodiment of invention.

(Step 2')

The step 2' of the tenth embodiment of invention can be applied with the same conditions as of the step 2 of the third embodiment of invention.

(Step 3')

The step 3' of the tenth embodiment of invention can be applied with the same conditions as of the step 3 of the third embodiment of invention.

(Step 4')

The step 4' of the tenth embodiment of invention can be applied with the same conditions as of the step 4 of the third embodiment of invention.

(Step 5)

The step 5 of the tenth embodiment of invention can be applied with the same conditions as of the step 1 of the fifth embodiment of invention.

(Step 6)

The step 6 of the tenth embodiment of invention can be applied with the same conditions as of the step 2 of the fifth embodiment of invention.

(Step 7)

The step 7 of the tenth embodiment of invention can be applied with the same conditions as of the step 3 of the fifth embodiment of invention.

(Step 8)

The step 8 of the tenth embodiment of invention can be applied with the same conditions as of the step 4 of the fifth embodiment of invention.

(Step 9)

The step 9 of the tenth embodiment of invention can be applied with the same conditions as of the step 3 of the ninth embodiment of invention.

(Step 5')

The step 5' of the tenth embodiment of invention can be applied with the same conditions as of the step 1 of the sixth embodiment of invention.

(Step 6')

The step 6' of the tenth embodiment of invention can be applied with the same conditions as of the step 2 of the sixth embodiment of invention.

(Step 7')

The step 7' of the tenth embodiment of invention can be applied with the same conditions as of the step 3 of the sixth embodiment of invention.

(Step 8')

The step 8' of the tenth embodiment of invention can be applied with the same conditions as of the step 4 of the sixth embodiment of invention.

(Step 9')

The step 9' of the tenth embodiment of invention can be applied with the same conditions as of the step 3 of the ninth embodiment of invention.

(Step 10)

The step 10 of the tenth embodiment of invention can be applied with the same conditions as of the step 4 of the ninth embodiment of invention.

3. As to a Method of Improving a Yield of Target Double-Stranded Nucleic Acid Molecules For the purpose of increasing discriminability and a concentration effect, the methods of the first to eight embodiments of invention may be used in combination. In one embodiment of the present invention, when one or more of the first to third embodiments of invention are applied to the same sample plural times although not limited thereto, the concentration of target double-stranded nucleic acid molecules at a higher recovery rate can be achieved.

In another embodiment of the invention, when using the step of removing non-target double-stranded nucleic acid molecules from a sample by use of a second PI polyamide in at least one of the fourth to sixth embodiments of invention and then the step of capturing target double-stranded nucleic acid molecules from the sample by use of a first PI polyamide in at least one of the first to third embodiments of invention, the concentration of the target double-stranded nucleic acid molecules at a higher recovery rate can be achieved.

Especially, if the amount ratio between target double-stranded nucleic acid molecules and non-target double-stranded nucleic acid molecules in a sample is such that the non-target double-stranded nucleic acid molecules are pronouncedly present, the fourth embodiment of invention and/or the fifth embodiment of invention is repeated plural times thereby adequately removing the non-target double-stranded nucleic acid molecules from the sample, followed by recovering the target double-stranded nucleic acid molecules according to the first to third embodiments of invention. In this way, there can be achieved the concentration of the target double-stranded nucleic acid molecules at a higher recovery rate.

When the seventh embodiment of invention and/or the eighth embodiment of invention wherein the first PI polyamide and the second PI polyamide are both used simultaneously is repeated plural times, the concentration effect can be more improved.

4. As to the General Procedures of the Methods of the First to Tenth Embodiments of Invention The recovery and concentration methods making use of PI polyamides related to embodiments of the present invention differ from those of ordinary employed major group binders, for which there is no need of strict temperature control and a control device for denaturation and hybridization steps. Accordingly, all the steps set out before can be performed under room temperature. In this regard, however, a temperature control may be feasible, if necessary, for the purpose of achieving the discriminability and concentration effect.

In all steps set out hereinbefore, after the formation of the complex A or the complex B, the method of separating the complex A or B from a liquid component and recovering the complex A or removing the complex B can be carried out according to ordinary solid-liquid separation operations.

In the first to eighth embodiments of invention set out hereinbefore, the removal method making use of the shape of a carrier (particles fixed on a substrate surface or on the inner wall surface of a container or the like) can be adopted.

In the step 3 of the first embodiment of invention, where a carrier is, for example, in the form of particles, the separation of the complex A can be carried out according to a method wherein the complex A is settled down by centrifugal separation and the resulting supernatant is removed by decantation or pipetting.

Where the carrier is fixed on a substrate surface or an inner wall surface of a container or the like, a sample containing target double-stranded nucleic acid molecules and non-target double-stranded nucleic acid molecules and a PI polyamide are added to the container so that the target double-stranded nucleic acid molecules binding with a first PI polyamide can be contacted with the carrier, followed by removing the resulting supernatant by decantation or pipetting.

For instance, in the step 3 of the fourth embodiment of invention, where the carrier is in the form of particles, the separation of the complex B can be carried out according to a method wherein the complex B is settled down by centrifugal separation and recovered by removing the resulting supernatant by decantation or pipetting.

Where the carrier is fixedly attached to a substrate surface or the inner wall surface of a container or the like, a sample containing target double-stranded nucleic acid molecules and non-target double-stranded nucleic acid molecules and a PI polyamide are added to the container so that the non-target double-stranded nucleic acid molecules binding with a second PI polyamide can be contacted with the carrier, followed by recovering a supernatant containing the complex A by decantation or pipetting.

When a solution containing a carrier is passed through a porous membrane or filter paper sufficient to disable the passage of the carrier, the separation between the carrier and the resulting liquid component is enabled. Where the carrier is in the form of a membrane such as a silica membrane or the like, the passage of a sample containing target double-stranded nucleic acid molecules and non-target double-stranded nucleic acid molecules through the silica membrane enables the separation between the carrier and the liquid component by contact of the mixture with the silica membrane. When the mixture is passed through the silica membrane, the removal and separation of the silica membrane and the liquid component may be performed by centrifugal separation treatment or by application of vacuum or pressure.

A carrier may be mixed with a sample containing target double-stranded nucleic acid molecules and non-target double-stranded nucleic acid molecules simultaneously with the mixing of the sample with a PI polyamide. Alternatively, the mixture of a sample containing target double-stranded nucleic acid molecules and non-target double-stranded nucleic acid molecules and a PI polyamide may be incubated over a given time to permit adequate binding with the PI polyamide in the sample, followed by contacting a carrier with the resulting mixture. Still alternatively, while bringing a mixture of a sample containing target double-stranded nucleic acid molecules and non-target double-stranded nucleic acid molecules and a PI polyamide into contact with a carrier, incubation may be performed over a given time, after which the resulting complex A is recovered, or the resulting complex B is separated and removed to separate the complex A or the complex B from a liquid component.

In all the cases of the steps of binding the PI polyamide and the double-stranded nucleic acid molecules in the above steps, the temperature conditions during the incubation should preferably appropriately controlled while taking the structure of the PI polyamide, the sequence characteristics and the type of sample, and the length of the double-stranded nucleic acid molecule. The temperature can be set at 25° C. to 100° C., preferably at 25° C. to 80° C., more preferably at 25° C. to 50° C. and much more preferably at 25° C. to 40° C.

In all the cases of the above steps, it is preferred that the amount of the carrier used and the time from the contact of the carrier with the mixture of a sample containing target double-stranded nucleic acid molecules and non-target double-stranded nucleic acid molecules and a PI polyamide till the separation of the carrier are so adjusted that substantially all the amount of the nucleic acid molecules (i.e. the target double-stranded nucleic acid molecules in the case of the first PI polyamide, or the non-target double-stranded nucleic acid molecules in the case of the second PI polyamide) to be bound with the PI polyamide in the sample of the target double-stranded nucleic acid molecules and non-target double-stranded nucleic acid molecules is allowed to be adsorbed on the carrier. Accordingly, with the case of the method of concentrating target double-stranded nucleic acid molecules by use of the first PI polyamide (e.g., the first to third embodiments of invention), the target double-stranded nucleic acid molecules are pronouncedly smaller than the non-target double-stranded nucleic acid molecules, so that if it is assumed that the content of the target double-stranded nucleic acid molecules is not larger than 10%, incubation over a relatively long time (e.g., about 60 minutes) should preferably be made. In contrast, with the case using the second PI polyamide, it is preferred that the incubation should be made within a relatively short time (e.g., about 10 minutes). More preferably, when the incubation is continued for 30 minutes or over, the non-target double-stranded nucleic acid molecules are bound with the second PI polyamide, thereby enabling the non-target double-stranded nucleic acid molecules to be separated and removed from the sample.

In all the cases of the above steps, the amount of a PI polyamide is preferably appropriately adjusted while taking into account the structure of the PI polyamide, sequence characteristics, the type of sample, the length of double-stranded nucleic acid molecules and the like. In all the cases of the foregoing steps, the amount is preferably not less than an equivalent to the total double-stranded nucleic acid molecules. More preferably, the amount is $10^2$ to $10^8$ times the amount of the total double-stranded nucleic acid molecules. The amount ratio (the number of molecules) of the PI polyamide to the total double-stranded nucleic acid molecules in a sample to be mixed is at $10^2$ to $10^8$ times, preferably $10^4$ to $10^8$ times, more preferably $10^6$ to $10^8$ times and much more preferably $10^7$ to $10^8$ times.

5. As to the Materials Used in the Methods According to Embodiments of the Present Invention (1) Sample The PI polyamide related to an embodiment of the invention is made up of molecules allowing double-strand-specific binding, so that target and non-target nucleic acid molecules should preferably be double-stranded nucleic acid molecules. More preferably, the target and non-target nucleic acid molecules should be double-stranded DNA, respectively.

The nucleic acid molecules recovered by the concentration method of target double-stranded nucleic acid molecules according to an embodiment of the present invention may be double-stranded DNA irrespective of its base sequence length and may be either a linear nucleic acid or a cyclic nucleic acid such as a plasmid. Alternatively, an epigenetically modified nucleic acid may be used. Moreover, the nucleic acid molecules recovered in the inventive concentration method of target double-stranded nucleic acid molecules may be a circulatory free DNA (ccf DNA) derived from cells flowing in blood, mitochondria-derived DNA, a nucleic acid derived from an incorporated microorganism, or an artificial or synthetic nucleic acid. Examples of the artificial or synthetic nucleic acid include a cosmid, a vector, cDNA and fragments thereof.

The sample used for the concentration method of target double-stranded nucleic acid molecules according to an embodiment of the present invention may be one that contains target nucleic acid molecules of such nucleic acid molecules as stated above. For example, mention may be made of a sample that contains nucleic acid molecules obtained, for example, from a solid biopsy through an extraction or purification step, or a liquid biopsy containing nucleic acid molecules, such as blood serum, blood plasma, urine, ascites fluid, pleural effusion, peripheral blood, lymph fluid or the like. In conventional methods, it is necessary to use a sample that contains highly pure nucleic acids purified from such a liquid biopsy as mentioned above according to commercially available nucleic acid reagents or kits, or according to other known methods. However, with the concentration method of target double-stranded nucleic acid molecules according to an embodiment of the present invention, the target double-stranded nucleic acid molecules can be recovered directly from a liquid biopsy, such as blood serum, blood plasma or urine without resorting to the nucleic acid purifying step in a manner as stated above.

The concentration method of target double-stranded nucleic acid molecules according to an embodiment of the invention is one wherein target double-stranded nucleic acid molecules can be efficiently concentrated if there are one or more base differences in the base sequence between the target double-stranded nucleic acid molecules and non-target double-stranded nucleic acid molecules. For example, the target double-stranded nucleic acid molecules are the human genome wherein a base sequence difference between target double-stranded nucleic acid molecules and non-target double-stranded nucleic acid molecules may be either a one-base difference due to a point mutation, or one or more base differences due to a deficit.

The concentration method of target double-stranded nucleic acid molecules according to an embodiment of the present invention is suited, for example, for concentrating target nucleic acid molecules contained in a sample in a small amount. The concentration method of target double-stranded nucleic acid molecules ensures a significant concentration effect even when the content of target nucleic acid molecules in a sample is 1.0, 0.1 or 0.001%. Moreover, the concentration method of target double-stranded nucleic acid molecules is relatively simple when compared with prior art methods with respect to the operations of the respective steps and does not need any strict temperature control or any temperature control device, thus enabling development to automation. Moreover, the concentration method of target double-stranded nucleic acid molecules is suited for a variety of analysis methods because the target double-stranded nucleic acid molecules in a sample is so concentrated that the high sensitivity analysis of the target nucleic acid is possible even when using a relatively low, analytical sensitivity method. In other words, the concentration method of target double-stranded nucleic acid molecules is one that can be developed in the field of clinical studies and diagnosis by combination of various analysis methods.

Although the target double-stranded nucleic acid molecules obtained by the concentration method of target double-stranded nucleic acid molecules according to an embodiment of the invention may be provided for any one of nucleic acid analyses, it is preferred that they are provided, especially, for analyses of gene polymorphism and genetic mutation (e.g., genetic test). It is more preferred to be provided for SNP (Single Nucleotide Polymorphism) and monogenetic mutation. Especially, where it is intended to recover and concentrate nucleic acid molecules containing a small amount of mutated genes in a cancer cell-derived, circulatory DNA, the nucleic acid molecules containing the recovered mutated genes are served for nucleic acid analyses for many purposes of prognostic diagnosis of carcinoma, follow-up monitoring of a person affected with carcinoma, or observation of an effect of an anticancer treatment on against malignancy.

(2) Pyrrole-imidazole-containing polyamide (PI polyamide)

The pyrrole-imidazole-containing polyamide means small molecules constituted of pyrrole (Py) amino acid (preferably N-methylpyrrole amino acid) which is able to specifically bind, by affinity of not larger than nanomols, to an arbitrary, predetermined base sequence in a human genome and imidazole (Im) amino acid (preferably N-methylimidazole amino acid); or beta-alanine (β-Ala). The aromatic amino acid used herein means an aromatic compound having an amino substituent group and a carboxyl substituent group on the aromatic ring.

In the present specification, the pyrrole amino acid units and the imidazole amino acid units in the pyrrole-imidazole-containing polyamide may be merely called pyrrole (Py) and imidazole (Im), respectively.

One example of the pyrrole-imidazole-containing polyamide modified with a linker molecule used in the method according to an embodiment of the present invention has a hair pin-shaped structure represented by the following formula 1

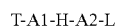 (Formula 1)

wherein T is a terminal region, A1 and A2 are, respectively, a hybridizing region, H is a connected region, and L a linker molecule.

Figure 17:
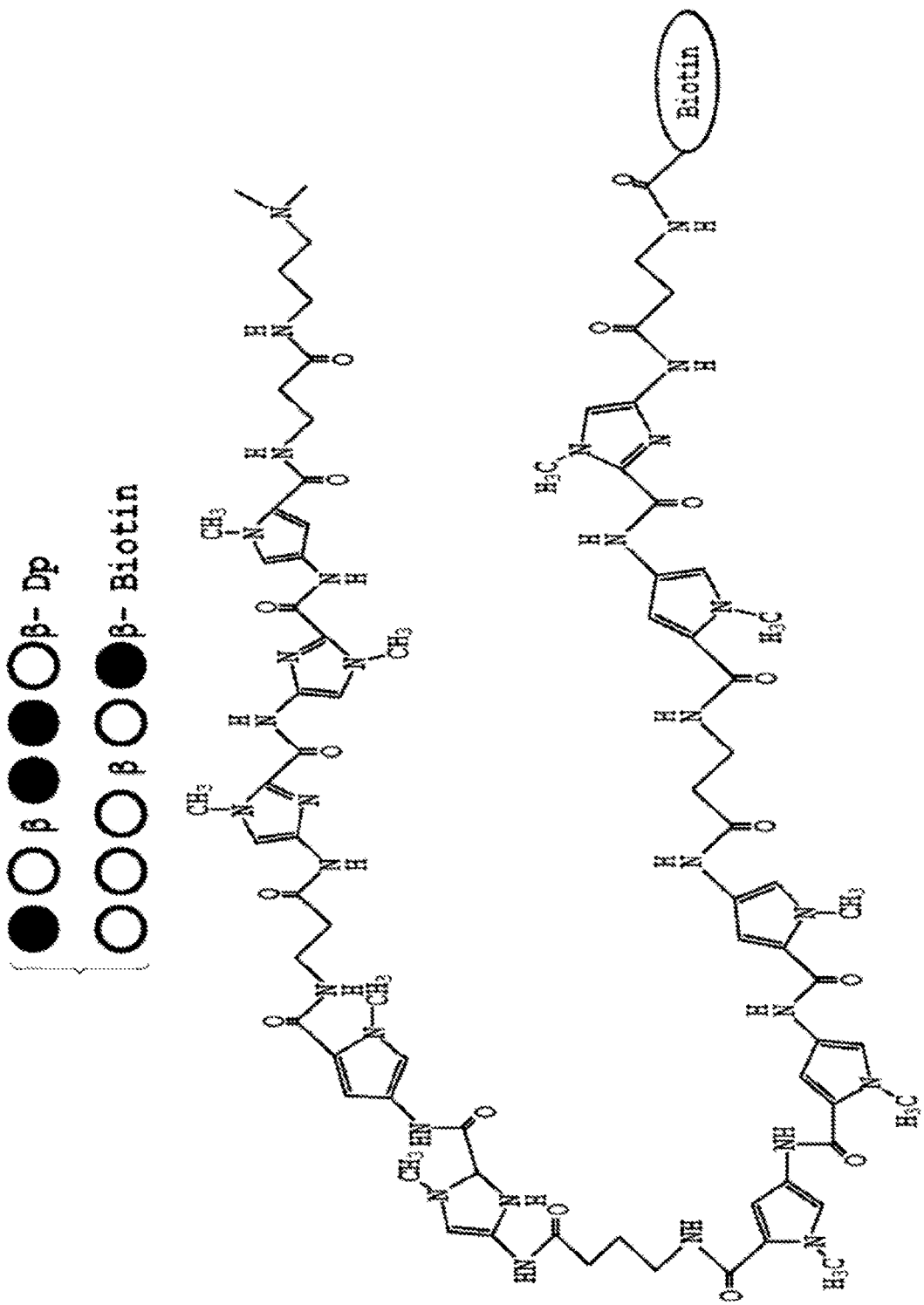
FIG. 17 is a schematic view showing a sequence of a pyrrole-imidazole-containing polyamide bound with a target double-stranded nucleic acid molecule and its structural formula according to an embodiment of the invention.
Figure 18:
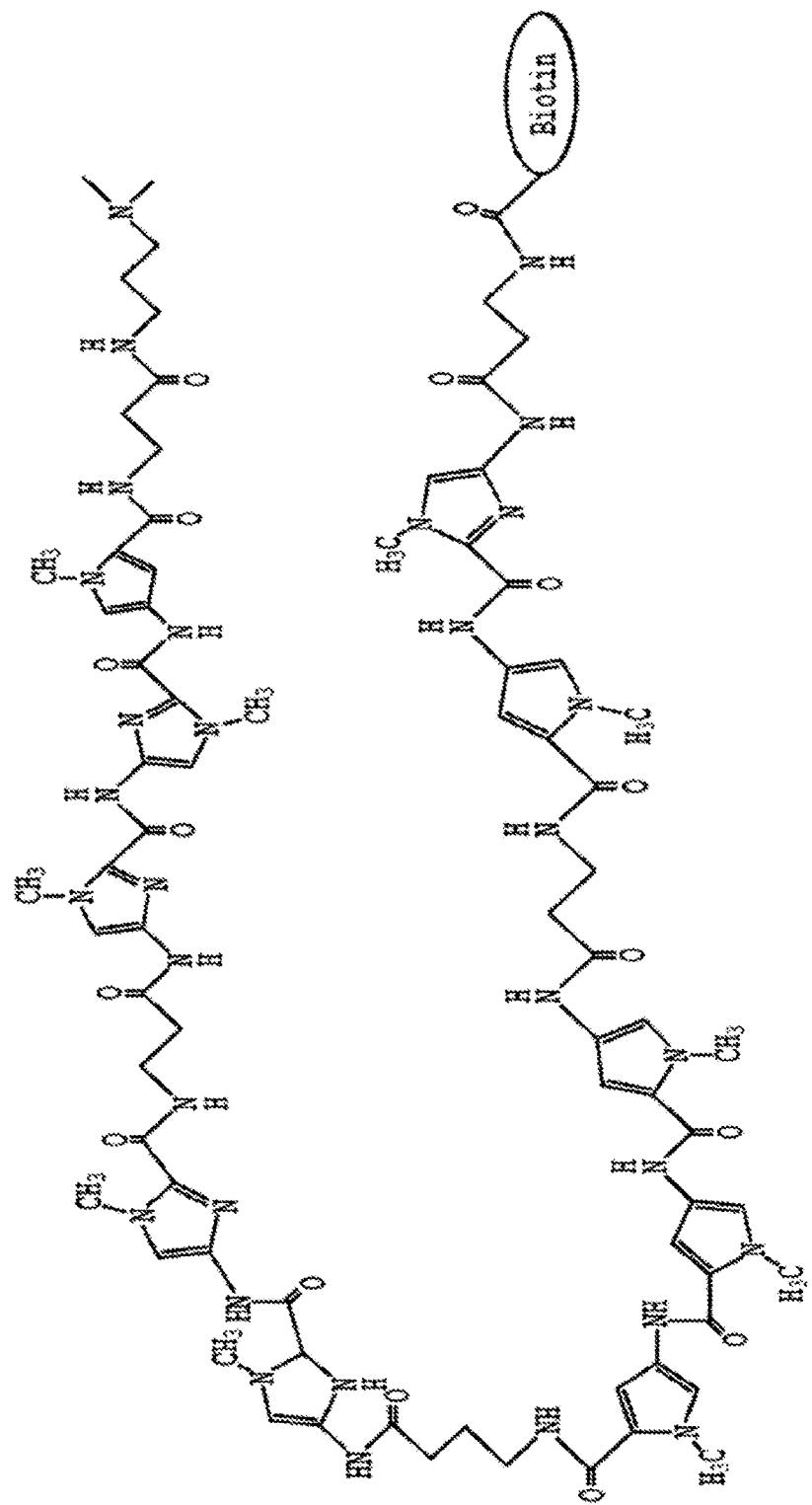
FIG. 18 is a schematic view showing a sequence of a pyrrole-imidazole-containing polyamide bound with a non-target double-stranded nucleic acid molecule and its structural formula according to one embodiment of the invention.
Figure 19:
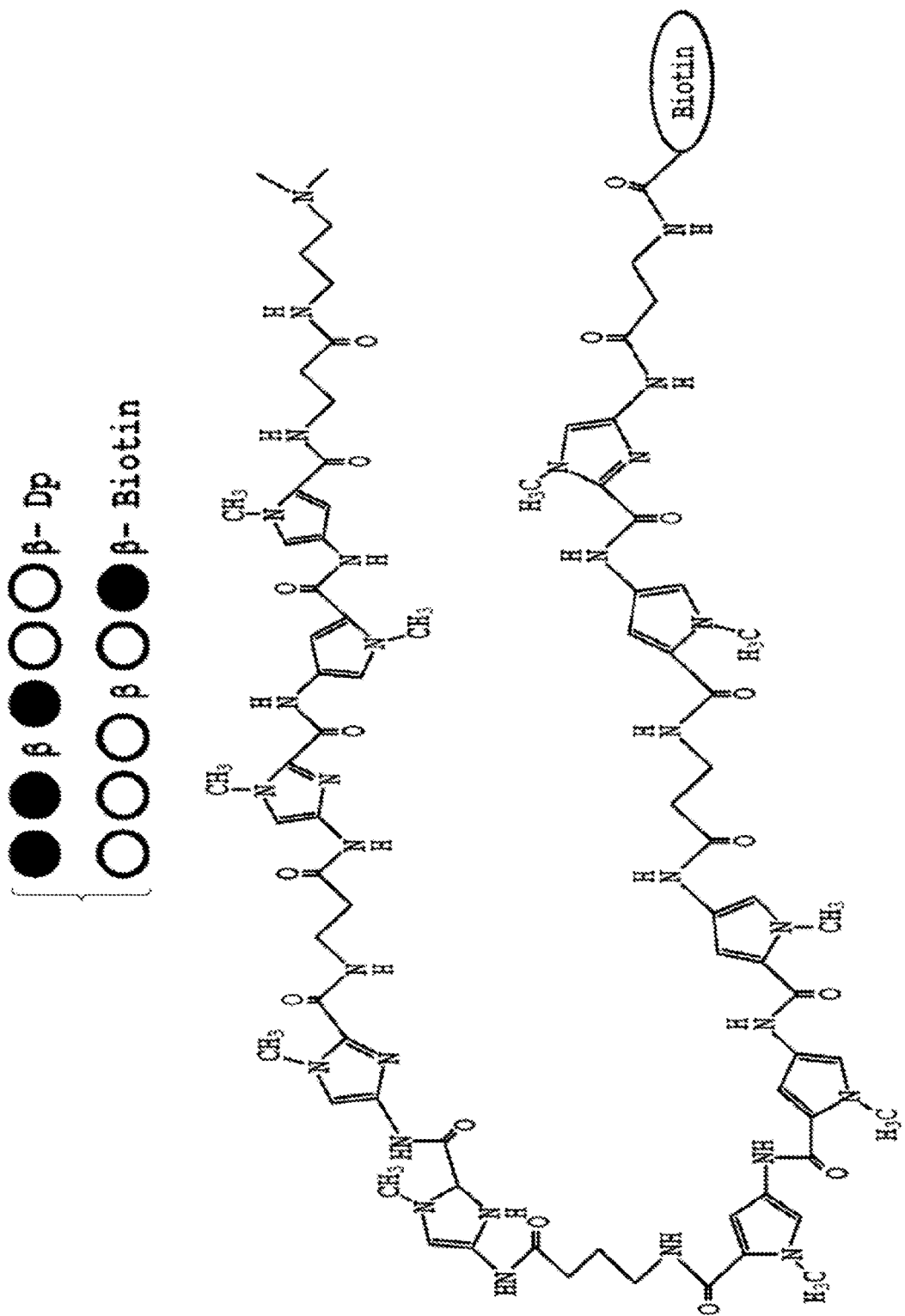
FIG. 19 is a schematic view showing a sequence of a pyrrole-imidazole-containing polyamide bound with a target double-stranded nucleic acid molecule and its structural formula according to an embodiment of the invention.

As the connected region (11) at the respective one terminals of the two hybridizing regions (12, 13), γ-aminobutanoic acid (gamma turn) can be introduced, for example. Examples of the structures having the connected region (11) connecting the two hybridizing regions therewith are shown in FIGS. 17 to 19. When a substance having a rotatable single unit is introduced into the connection site, the two hybridizing regions form a pair therebetween by chemical interaction, resulting in the formation of a hair pin-shaped structure.

When the pyrrole-imidazole-containing polyamide modified with the linker molecule is formed to have the hair pin-shaped structure in this way, the Py, Im and β-Ala constituting the hybridizing regions (A1 and A2) form a pair between the hybridizing regions, thus enabling good discrimination of the sequence constituted of a base pair of double-stranded DNA (A-T and C-G) thereby binding to a minor groove having a specific sequence of the double-stranded DNA as stated hereinafter.

One example of the pyrrole-imidazole-containing polyamide modified with the linker molecule used in the method according to an embodiment of the invention related to the present application has such a cyclic structure represented by the following formula (2)

 (Formula 2)

wherein A1 and A2, respectively, represent a hybridizing region, H represents a connected region, and L represents a linker molecule. The reason why the linker molecule (L) is shown as a bond passing through the ring is such that the linker molecule (L) is able to bind to any arbitrary position of the ring.

The pyrrole-imidazole-containing polyamide modified with the linker molecule as used in the method according to an embodiment of the invention related to the present application is described in more detail with reference to FIG. 14A.

Figure 14A:
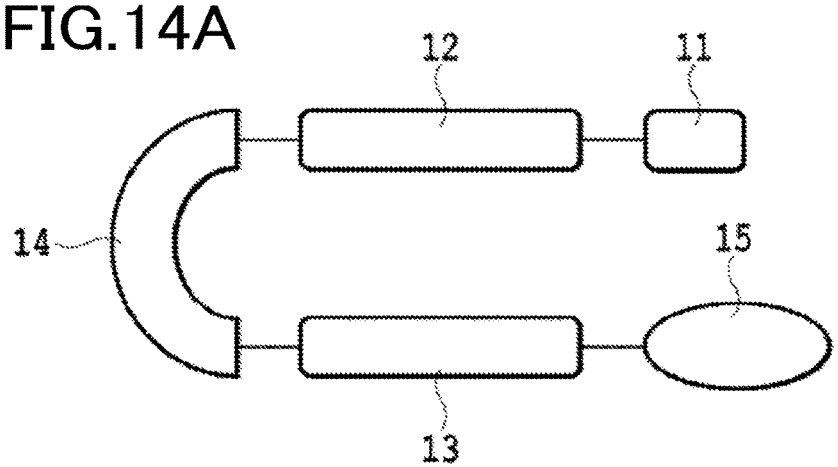
FIG. 14A is a schematic view showing a pyrrole-imidazole-containing polyamide of a hair-pin type related to an embodiment of the present invention.

As shown in FIG. 14A, the polyamide is made up of a terminal region (11) corresponding to T in the formula 1, two hybridizing regions (12, 13) corresponding to A1 and A2 in the formulas 1 and 2, a connected region (14) connecting the two hybridizing regions therewith and corresponding to T in the formulas 1 and 2, and a linker molecule (15) that is bound to a terminal opposite to the above terminal site and corresponding to L in the formulas 1 and 2 (FIG. 14A). The terminal region 11 is made, for example, of N,N-dimethylaminopropylamine.

The two hybridizing regions (12, 13) of the pyrrole-imidazole-containing polyamide are each constituted of a sequence arbitrarily selected from a plurality of imidazole (Im), pyrrole (Py) and β-alanine (β-Ala) moieties. The Im, Py and β-Ala moieties forming the hybridizing regions (12, 13) are intermolecularly connected through an amide bond.

These Im, Py and β-Ala forming these two hybridizing regions (12, 13) are able to recognize an A-T pair and a G-C pair of double-stranded DNA by the pair combination between the both regions. The Im/Py pair formed between the two hybridizing regions (12, 13) recognizes the G-C pair in the DNA double-strand, and Py/Py, Py/β-Ala, β-Ala/Py and β-Ala/β-Ala pairs recognize the A-T pair in the DNA double strand, respectively. Besides, a diversity of sequence rules is elucidated. For example, it has been reported that the β-Ala residue or the β-Ala/β-Ala pair in the pyrrole-imidazole-containing polyamide serves to mitigate the steric hindrance in the binding between the pyrrole-imidazole-containing polyamide and the base sequence of a target double-stranded nucleic acid molecule, and its introduction in every two residues or three residues in the pyrrole-imidazole-containing polyamide sequence can more enhance the affinity (NPL 3).

Figure 14B:
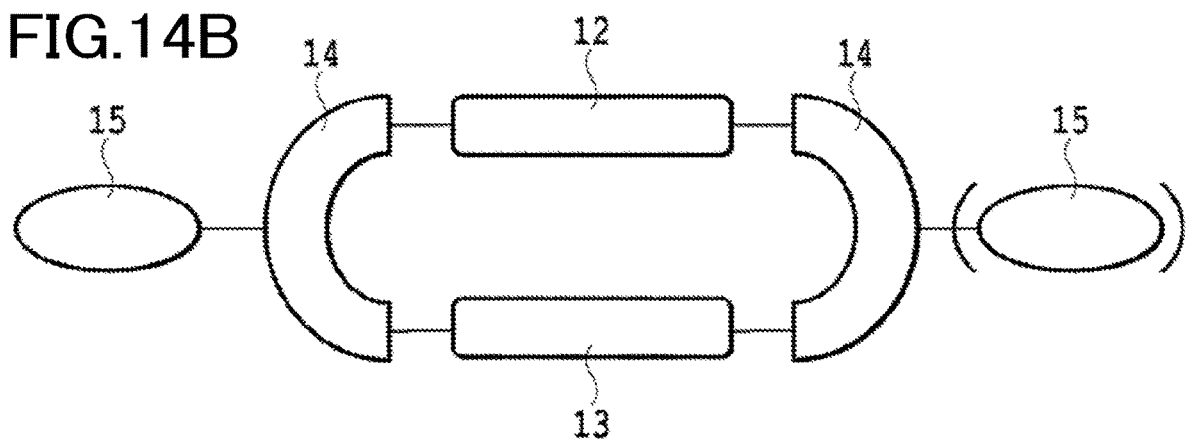
FIG. 14B is a schematic view showing a pyrrole-imidazole-containing polyamide having a cyclic structure which is related to an embodiment of present invention.

As shown in FIG. 14B, when the connected region (14) is introduced at opposite terminals of the two hybridizing regions (12, 13), a ring structure can be made. The two linker molecules (15) in FIG. 14B may be both provided, but either one may be provided. It has also been reported that when the connected region (14) formed by the gamma turn capable of forming the ring structure is made of γ-aminobutanoic acid, it has discriminability against an A-T or T-A pair.

Aside from the sequence rules of Py, Im and β-Ala for these hybridizing regions (12, 13), a number of sequence rules are present. Accordingly, it has been accepted that functional molecules having discriminability and binding power comparable to major group binders such as artificial nucleic acids and the like can be designed using sequence combinations. For example, hydroxypyrrole (Hp) may be used as a constituent element of the hybridizing regions (12, 13).

The first PI polyamide formed of the pyrrole-imidazole-containing polyamide has a sequence capable of binding to a target double-stranded nucleic molecule and the second PI polyamide has a sequence capable of binding to a non-target double-stranded nucleic acid molecule, preferably along with at least one function and feature indicated below.

(1) To be capable of binding to a base pair (T-A or A-T) within a target base sequence or in the vicinity thereof and contain at least one spacer molecule capable of forming a hair pin-shaped structure in the pyrrole-imidazole-containing polyamide.

(2) To be capable of binding to a base pair (T-A or A-T) within a target base sequence or in the vicinity thereof and form a ring structure as a result of containing two or more spacer molecules capable of forming a hair pin-shaped structure in the pyrrole-imidazole-containing polyamide.

(3) To contain at least one β-alanine residue in every 2 or 3 residues of constituent molecules (Py or Im) of the pyrrole-imidazole-containing polyamide within its sequence.

(4) To contain at least one linker molecule at the terminal of the sequence.

(5) To be a Py, Im and β-Ala-containing sequence having a length sufficient to adequately recognize the base sequences of a target double-stranded nucleic acid molecule and a non-target double-stranded nucleic acid molecule.

More preferably, the first PI polyamide has a sequence capable of binding to the target double-stranded nucleic acid molecule and the second PI polyamide has a sequence capable of binding to the non-target double-stranded nucleic acid molecule, and both have the function of either (1) or (2) and the functions of (3), (4) and (5).

Outline of a synthetic method of a PI polyamide modified with a protein

The PI polyamide used in embodiments of the present invention can be prepared according to a number of methods described in PTL 5 (JP 3231045 B specification), PTL 6 (JP 4012145 B specification), and NPLs 1 to 4 although not limited thereto.

Figure 16:
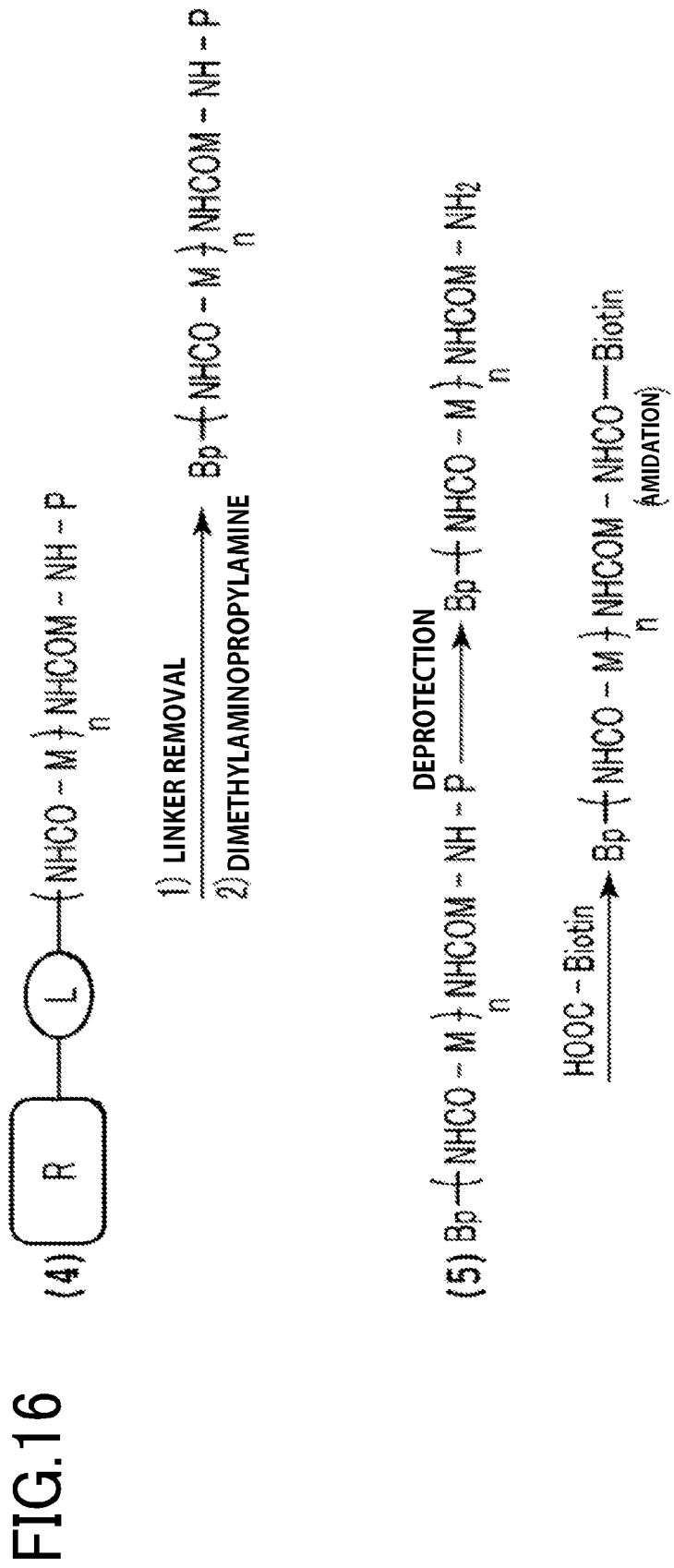
FIG. 16 is a scheme (No. 2) of a synthetic method wherein a protein is bound to the PI polyamide modified with a linker molecule.

An outline of a synthetic method of a PI polyamide usable in embodiments of the present invention is described by way of embodiment. The following example is a synthetic example of a PI polyamide-protein conjugate modified with a protein (e.g., biotin), which can be synthesized through the following five steps. The synthetic scheme is as shown in FIGS. 15 and 16.

(Step 1) This step is one wherein a solid carrier is provided. As shown in FIG. 15(1), the solid carrier has a linker (L) on a resin (R). The solid carrier may not have any linker in the case where an amino group is present directly on the resin (R). The solid carrier can be prepared by modifying the resin with a linker having an amino group. A generally known method may be adopted for the preparation. In one embodiment, a resin such as polystyrene may be used, for example, as the resin of the solid carrier (FIG. 15(1)). The linker may be those indicated in the above-indicated PTLs, for example.

(Step 2) Next, a monomer necessary for the preparation of an intended polyamide. The monomer includes a monomer having a pyrrole group which is modified with a carboxyl group and amino group (a pyrrole-derived monomer), a monomer having an imidazole group which is modified with a carboxyl group and an amino group (an imidazole-derived monomer), and β-alanine. More particularly, the pyrrole-derived monomer includes 4[(9-fluorenylmethoxycarbonyl)amino]-1-methyl-2-pyrrole carboxylic acid and the imidazole-derived monomer includes 4-[(9-fluorenylmethoxycarbonyl)amino]-1-methyl-2-imidazole carboxylic acid. In this step, it is preferred that the amino group is protected. The pyrrole-derived monomer and the imidazole-derived monomer can be obtained according to known methods, respectively. The protective group for the amino group of these monomers includes a tert-butoxycarbonyl group (Boc group), 9-fluorenylmethyloxycarbonyl group (Fmoc group), or the like. The introduction of the protective group may be performed by known methods.

(Step 3)

This step is one wherein the monomers provided in the step 2 are bound to the solid carrier provided in the step 1, respectively. Initially, a monomer whose amino group is protected is bound to the amino group of the solid carrier. Next, the amino group of the monomer is deprotected, to which another monomer is bound. The deprotection of the amino group and the binding of the monomer are repeated to obtain the solid carrier and an intended PI polymer having an amino protecting group (FIG. 15(3)). The deprotection of the amino group and the binding of the monomer (formation of an amide bond) can be performed by use of known methods.

(Step 4) The PI polyamide (R) and the linker obtained in the above step 3 are removed to obtain a PI polyamide having an amino protecting group. Dimethylaminopropylamine (Bp) is introduced at the terminal side of the carboxyl group of the resulting polyamide (FIG. 16(4)). The introduction of Bp into the carboxyl group (formation of an amide bond) can be performed by a known method.

(Step 5) The amino protecting group (P) of the PI polyamide bound with Bp is subjected to deprotection, followed by amide bonding of a protein (e.g., biotin) at the PI polyamide terminal to obtain an intended PI polyamide-protein conjugate (FIG. 16(5)). The deprotection of the amino group and the bonding of the protein (formation of an amide bond) are, respectively, performed by known methods.

Other embodiment of a synthetic method of a PI polyamide-protein conjugate is described below. In the above steps 1 and 2, the amino group of the solid carrier is replaced by a carboxyl group and the carboxyl group of a monomer is protected, after which the amino group of the monomer and the carboxyl group of the solid carrier are bound together. Next, the protected carboxyl group is deprotected, and the deprotection of the carboxyl group and the binding of an amino group of an appropriate type of monomer are repeated in the same manner as in the step 3 to obtain a solid carrier and a PI polyamide having a protecting group. Thereafter, a protein and Bp can be introduced in the same procedures as in the steps 4 and 5. Moreover, in a further embodiment, a protein or Bp may be initially provided, followed by successively binding monomers.

The PI polyamide related to embodiments of the invention is a molecule enabling double-stranded specific binding, for which it is preferred that target and non-target nucleic acid molecules are double-stranded nucleic acid molecules, respectively. More preferably, target and non-target nucleic acid molecules are, respectively, double-stranded DNA.

In all the cases of the forgoing steps, the amount of the PI polyamide should be preferably appropriately adjusted while taking into account the structure and sequence characteristics of the PI polyamide, the type of sample and the length of a double-stranded nucleic acid molecule. In all the cases of the steps, the amount is preferably at least not less than equivalent to the total double-stranded nucleic acid molecules, more preferably $10^2$ to $10^8$ times the amount of nucleic acid molecules.

(3) Carrier

The carrier used in embodiments of the present invention is not specifically limited so far as a double-stranded nucleic molecule is able to bind to the above linker molecule and the ligand molecule, and may be in all phase states such as of solid, liquid and gel. The material may be made of an inorganic material, an organic material or a combination thereof. The carrier has a ligand molecule capable of binding to the terminal linker molecule of the pyrrole-imidazole-containing polyamide by specific interaction.

Where the carrier used in embodiments of the invention is made of an inorganic material, the carrier may be one or more of those selected from the group consisting of a silicate-containing material, zeolite, aluminum oxide, titanium dioxide, zirconium dioxide, kaolin, magnetic particles and ceramics. The silicate containing material may be silica, magnetic silica, glass, or silicon dioxide.

Where the carrier used in embodiments of the invention is made of an organic material, the carrier may be an organic polymer constituted of at least one of those selected from the group consisting of Teflon (registered trade name), polyesters, polyether sulfones, polycarbonates, polyacrylate copolymers, polyurethanes, polybenzimidazoles, polyolefins, polyvinyl chloride, and polyvinylidene fluoride. Alternatively, there may be used organic polymers including positively or negatively charged nylons or polysaccharide structures made of at least one of those selected from the group consisting of cellulose, cellulose-mixed esters, cellulose nitrate and nitrocellulose.

The carrier used in embodiments of the present invention is made of an organic material and also of a biopolymer, it may be constituted of at least one of those selected from the group consisting of proteins, carbohydrates, lipids and nucleic acids.

The carrier is not specifically limited with respect to its shape and may be in the form of particles or a membrane or a substrate if it is solid, for example. The carrier may be fixedly attached to the inner wall surface of a container wherein a complex is formed. For instance, when non-target double-stranded nucleic molecules are removed as a complex B, a carrier b is fixed within a container so that the complex B is formed on the inner wall surface of the container. Thus, a supernatant containing target double-stranded nucleic acid molecules can be recovered from the container. Aside from the solid, a gel-shaped body may be used, for example.

The carrier (in the form of magnetic particles, beads or the like) used in the examples of the present invention wherein avidin is fixed can be prepared by a method wherein the carrier is modified with a variety of functional groups (amino group, carboxyl group, hydroxyl group, thiol group, aldehyde group and the like) and avidin is fixed by coupling through the functional group of the avidin molecule or through a ligand molecule although not limited thereto.

In one embodiment of the present invention, the magnetic particles (Magnosphere MS300/Streptavidin, manufactured by JSR Corporation) used in the examples of a fixation method of avidin on a carrier are such that a magnetic layer is coated onto latex particles, followed by forming a shell of a copolymer made mainly of a methacrylate monomer although not limited thereto. Alternatively, magnetic particles may be prepared by subjecting the carboxyl group on the surface to coupling with an amino group of the avidin molecule thereby modifying the surface with the avidin.

Another usable fixation method of avidin on a carrier is one described in PTL 7 (WO 2012/111687).

(4) Linker molecule and ligand molecule

The terms "linker molecule" and "ligand molecule" used herein mean molecules that are able to be mutually, specifically bound together, for example, like streptavidin and biotin. In the examples of the present invention, biotin is used as a linker for the pyrrole-imidazole-containing polyamide, and streptavidin is used as a ligand molecule capable of specifically binding to the linker molecule fixed to a carrier. Substances showing a similar binding behavior may also be used in embodiments of the present invention without limiting to streptavidin and biotin.

The carrier used in the recovery and concentration method of target double-stranded nucleic acid molecules using the PI polyamide related to embodiments of the invention should preferably have, on the surface thereof, a molecule which may be sometimes referred to as "ligand molecule" hereinafter) capable of specifically binding to the terminal linker molecule of the PI polyamide through covalent bond, ionic bond or van der Waals force. More preferably, it has a molecule that has a specific bonding force, comparable to the covalent bond, with the terminal linker molecule of the PI polyamide.

The interaction between the ligand molecules, which have a specific binding force as high as a covalent bond with the terminal linker molecule of the PI polyamide as mentioned above and which are adoptable as a binding interaction used in embodiments of the invention includes, for example, those of antibody/antigen (streptavidin-biotin binding), antibody/hapten, enzyme/substrate, enzyme/inhibitor, enzyme/cofactor, binding protein/substrate, carrier protein/substrate, lectin/carbohydrate, acceptor/hormone, acceptor/effector, complementary strand of nucleic acid, protein/nucleic acid, repressor/inducer, ligand/cell surface receptor, virus/ligand and the like. The covalent bond may be those bonds such as of ester, amide, thioester, sulfoneamide, sulfonate, phosphonate, phosphoramidate, phosphorothioate or phosphoric bond and the like.

(5) Other reagents (i) Buffer

The buffer usable in the recovery and concentration method of target double-stranded nucleic acid molecules using the PI polyamide related to embodiments of the present invention is one that contain at least one or more of water, a pH buffering agent, a surfactant, and a divalent and/or monovalent cation. If contained, the surfactants or salts may be used singly or in combination.

It will be noted that the buffer may further contain substances other than the pH buffering agent, the surfactant, the divalent cation-containing salt, or the monovalent cation-containing salt so far as they do not impede the effect of embodiments of the invention.

(ii) Surfactant

A surfactant may be added to the buffer according to an embodiment of the invention. Such a surfactant may be appropriately selected from those surfactants ordinarily employed in this technical field. Although the surfactant to be contained in the buffer may be ionic surfactants such as SDS (sodium dodecylsulfate) and the like, non-ionic surfactants are preferred and more preferred surfactants include Triton (registered trade name) X (polyoxyethylene (10) octylphenyl ether), Tween (registered trade name) 20 (polyoxyethylene (20) sorbitan monolaurate), Tween (registered trade name) 40 (polyoxyethylene (20) sorbitan monopalmitate), Tween (registered trade name) 60 (polyoxyethylene (20) sorbitan monostearate), Tween (registered trade name) 80 (polyoxyethylene (20) sorbitan monooleate), Nonidet (registered trade name) P-40 (polyoxyethylene (9) octylphenyl ether), Brij (registered trade name) 35 (polyoxyethylene (23) lauryl ether), Brij (registered trade name) 58 (polyoxyethylene (20) cetyl ether), digitonin, and saponin. Triton X, Tween 20 or Nonidet P-40 are much more preferred.

Where the buffer contains a surfactant, the concentration of the surfactant may be one sufficient to serve as a blocking agent that inhibits non-specific binding and adsorption in the binding between a target or non-target double-stranded nucleic acid molecule and the PI polyamide or in the binding between the PI polyamide and a carrier, and can be appropriately adjusted while considering the amount, structure and sequence characteristics of the PI polyamide used, and the type of sample. For instance, the surfactant in the buffer is at not larger than 0.05 v/v %, preferably 0 to 0.01 v/v % or below, more preferably 0 v/v %, based on the volume of the solution after preparation.

(iii) Cation

It is preferred that the buffer used in embodiments of the invention further comprises a cation. The cation may be either a monovalent cation or a divalent cation. As the cation, mention is made of a lithium ion, a sodium ion, a potassium ion, a rubidium cation, a cesium cation, an ammonium cation, a magnesium cation, a calcium cation, a strontium cation and the like. Of these, a lithium cation, a sodium cation, a magnesium cation or a calcium cation is preferred. The anions pairing with these cations preferably include a chloride ion, a bromide ion or an iodide ion, of which a chloride ion or bromide ion is more preferred and a chloride ion is much more preferred.

Where the buffer contains a cation, the concentration of the cation may be one sufficient to achieve the binding between a PI polyamide and a double-stranded nucleic acid molecule and the binding reaction between the PI polyamide and a carrier, and is appropriately determined while considering the type of cation used, the amount, structure and sequence characteristics of the PI polyamide and the type of sample. In the buffer used in embodiments of the present invention, the cation is preferably present at not larger than 1 mol/liter when taking it into consideration that concentrated target double-stranded nucleic acid molecules are subjected to ordinarily employed analyses such as PCR.

The buffer contains water and is prepared, if necessary, by dissolving at least one or more of a pH buffering agent, a surfactant, a divalent cation-containing salt and/or a monovalent cation-containing salt. The pH of the buffer is appropriately determined while considering the amount, structure and sequence characteristics of the PI polyamide used, the type of sample, and the analytical method to which recovered target double-stranded nucleic acid molecules are subjected. In the practice of embodiments of the invention, the pH of the buffer preferably ranges from 5.0 to 9.0, more preferably from 6.5 to 8.5 and much more preferably from 7.0 to 8.5. The buffer used may be appropriately selected from those buffers ordinarily used for analysis in this technical field. Specific examples of the buffer include a Tris (trishydroxymethylaminomethane)-HCl buffer, a phosphate buffer and the like. Water used as solvent for preparing the buffer is preferably deionized water or superpure water.

6. As to an Analytical Method

In the analyses of a nucleic acid including genetic analyses, it is general to analyze a nucleic acid that is an analysis object and also the information obtained as a result of the analysis. The nucleic acid analyses are mainly carried out by a method of directly reading a base sequence of a nucleic acid by a sequencer, a method using a polymerase reaction originating from a primer specifically hybridized with the region made of a specific base sequence, or a method making use of a probe specifically hybridized with the region made of a specific base sequence. The target double-stranded nucleic acid molecules obtained according to the concentration method of target double-stranded nucleic acid molecules related to an embodiment of the present invention usually contain a diversity of genetic nucleic acids or fragments thereof. The genes serving as an analysis object should preferably be analyzed according to a method using at least one of a primer and a probe. The methods using at least a primer include, for example a PCR (Polymerase Chain Reaction) method, a real time PCR method, a TaqMan (registered trade name)-PCR method, an LAMP (loop-mediated isothermal amplification) method, a SMAP (smart amplification process) process, a NASBA (nucleic acid sequence-based amplification) method, an RCA (rolling circle amplification) method and modified methods thereof. The methods using a probe include, for example, an Invader (registered trade name) method, a DNA microarray and the like. These methods may be used in appropriate combination thereof.

In the concentration method of target double-stranded nucleic acid molecule related to an embodiment of the present invention, there may be the case that only a small amount of target double-stranded nucleic acid molecules is obtained. The method of analyzing the target double-stranded nucleic acid molecules recovered by the concentration method of target double-stranded nucleic acid molecules related to an embodiment of the invention preferably includes analytical method making use of a nucleic acid amplifying reaction using a probe, or a method including a first stage wherein a nucleic acid is amplified such as by PCR and a second stage wherein the amplified product obtained in the first stage is subjected to nucleic acid analysis. The former method includes, for example, an allele-specific elongation method wherein the elongation reaction is carried out using a primer specific to a specific gene type, a TaqMan-PCR method and the like. The latter methods include, for example, an invader plus method, a PCR-RFLP (restriction fragment length polymorphism) method, a PCR-SSCP (single strand conformation polymorphism) method and the like. Of these, it is preferred to use a method wherein the target double-stranded nucleic acid molecules obtained by the concentration method of target double-stranded nucleic acid molecule related to an embodiment of the invention are amplified by PCR and directly read such as by a sequencer, or an invader plus method wherein amplification with PCR is performed, followed by subjecting to an invader method. This is because even if the target double-stranded nucleic acid molecules to be analyzed are very small in amount, high sensitivity and high accuracy nucleic acid analyses can be performed.

An example of a method of detecting and analyzing a specific gene (genetic analysis object) is shown. The nucleic acid analysis method of target double-stranded nucleic acid molecules recovered by the concentration method of target double-stranded nucleic acid molecules related to an embodiment of the invention is not limited thereto.

Initially, the solution (a solution containing the target nucleic acid molecules recovered by the first to third embodiments of invention when using the first PI polyamide, or a solution obtained after recovering by removal of the carrier in the fourth to sixth embodiments of invention) of the target double-stranded nucleic acid molecules recovered according to the concentration method of target double-stranded nucleic acid molecules related to an embodiment of the invention are mixed with an invader plus buffer that is an invader plus reaction solution, an oligomix for detecting an genetic analysis object and an enzyme mix, followed by denaturation treatment (under heating at 95° C. for 2 minutes) thereby melting the double helix of DNA into a single strand. It will be noted that the oligomix is made of a primer for PCR, a DNA probe, an invading oligo, and an FRET cassette.

Next, PCR is performed so that a nucleic acid at a site corresponding to a genetic analysis object is subjected to amplification reaction to deactivate the polymerase and stop the PCR.

Finally, the invader (registered trade name) method is carried out to decompose a DNA probe that has been specifically hybridized to a region having a nucleic acid sequence corresponding to the genetic analysis object. Next, 5'-oligonucleotide of the heated probe of DNA formed by the decomposition reaction is coupled with the FRET cassette having a fluorescent dye, and the FRET cassette is decomposed to permit the fluorescent to be released from the FRET cassette thereby emitting fluorescence. The measurement of the fluorescence enables the genetic analysis object to be indirectly detected and measured. In other words, the fluorescence signal intensity indicates a detection amount of the corresponding genetic analysis object.

The fluorescence signal intensity of the fluorescent dye dissociated by the invader method (registered trade name) is measured by a fluorescence measuring device. For example, if the fluorescence dye is FMA, the fluorescence signal intensity of FAM, which is observed at an excitation wavelength of 485 nm and an emission wavelength of 535 nm, is measured. The fluorescence measuring device is, for example, the fluorescence measuring device Light Cycler 480, manufactured by Roche Applied Science Inc.

7. As to Kit

<Kit for Concentrating Target Double-Stranded Nucleic Acid Molecules>

When the materials and reagents used in the concentration method of target double-stranded nucleic acid molecules related to an embodiment of the invention are kitted, the method can be simply performed.

The kit for the concentration method of target double-stranded nucleic acid molecules related to an embodiment of the invention is one that includes a first PI polyamide and/or a second PI polyamide modified with a linker molecule, and a carrier modified with a ligand molecule capable of specifically binding and/or adsorbing to the linker molecule, along with at least one or more of a pH buffering agent, a surfactant, a divalent cation-containing salt and/or a monovalent cation-containing salt. These materials and reagents mentioned above can be contained in the kit.

The hybridizing regions (FIGS. 14A and 14B) of the first PI polyamide and/or the second PI polyamide modified with a linker molecule, which can be included in the kit, can be arbitrarily, molecularly designed in conformity with a specific base sequence of a target gene intended to be detected by a genetic test.

The two hybridizing regions 12, 13 (FIG. 14A) of the pyrrole-imidazole-containing polyamide are respectively constituted of a sequence arbitrarily selected from a plurality of imidazole (Im), pyrrole (Py) and β-alanine (β-Ala). These Im, Py and β-Ala constituents of the hybridizing regions 12, 13 are intermolecularly connected via amide bond, respectively.

The molecular design of the discrimination sites should be made while considering the chemical properties of the following hybridizing regions. The Im, Py and β-Ala constituents of the two hybridizing regions 12, 13 are able to recognize an A-T pair and a G-C pair of double-stranded DNA by the pair combination between the both regions. The Im/Py pair formed between the two hybridizing regions 12, 13 recognizes the G-C pair of in DNA double strand, and Py/Py, Py/β-Ala, β-Ala/Py and β-Ala/β-Ala pairs recognize an A-T pair. Besides, a number of sequence rules have been made clear. For instance, the β-Ala residue or the β-Ala/β-Ala pair in the pyrrole-imidazole-containing polyamide sequence acts to mitigate the steric hindrance in the bond between the pyrrole-imidazole-containing polyamide and the recognized DNA double strand and can more enhance affinity when introduced in every two or three residues into the pyrrole-imidazole-containing polyamide.

Preferably, the hybridizing region of the first PI polyamide has a sequence capable of binding to a target double-stranded nucleic acid molecule and at least one or more of the following functions and features.

(1) To bind to a base pair (T-A or A-T) within a target base sequence or its vicinity and contain at least one spacer molecule capable of forming a hair pin-shaped structure in the pyrrole-imidazole-containing polyamide.

(2) To bind to a base pair (T-A or A-T) within a target base sequence or its vicinity and contain two or more spacer molecules capable of forming a hair-pin shaped structure in the pyrrole-imidazole-containing polyamide thereby enabling the formation of a cyclic structure.

To contain at least one β-alanine residue in every 2 or 3 residues within the sequence.

(4) To contain at least one linker molecule capable of specifically binding to a carrier at a sequence terminal.

(5) To be a sequence containing Py, Im and β-Ala each having a length sufficient to satisfactorily enable the recognition of the base sequence of a target double-stranded nucleic acid molecule and the base sequence of a non-target double-stranded nucleic acid molecule.

Preferably, the hybridizing regions of the second PI polyamide have a sequence capable of binding to a non-target double-stranded nucleic acid molecule and has at least one or more of the following functions and features.

(1) To bind to a base pair (T-A or A-T) within a non-target base sequence or its vicinity and contain at least one spacer molecule capable of forming a hair pin-shaped structure in the pyrrole-imidazole-containing polyamide.

(2) To bind to a base pair (T-A or A-T) within a non-target base sequence or its vicinity and contain two or more spacer molecules capable of forming a hair-pin shaped structure in the pyrrole-imidazole containing a polyamide thereby enabling the formation of a cyclic structure. As shown in FIG. 14B, a connected region may be introduced at the opposite terminals of the two hybridizing regions to provide a ring structure. The ring structure can be represented by a general formula. The two linker molecules in FIG. 14B may be both present, or either one present.

(3) To contain at least one β-alanine residue in every 2 or 3 residues within the sequence.

(4) To contain at least one linker molecule capable of specifically binding to a carrier at a sequence terminal.

(5) To be a sequence containing Py, Im and β-Ala each having a length sufficient to satisfactorily enable the recognition of the base sequence of a target double-stranded nucleic acid molecule and the base sequence of a non-target double-stranded nucleic acid molecule.

It is more preferred that the first PI polyamide has a sequence capable of binding to a target double-stranded nucleic acid molecule and the second PI polyamide has a sequence capable of binding to a non-target double-stranded nucleic acid molecule and that both have either of the functions (1) and (2) and the functions (3), (4) and (5).

The first PI polyamide and the second PI polyamide which can be included in the kit may be one which has the hair pin structure of the formula (1), or has the ring structure of the formula (2).

The ligand molecule which can be included in the kit and is capable of specifically binding to the linker molecule modifying a modified carrier is one that specifically binds to the linker molecule modified for the first PI polyamide and/or the second PI polyamide.

The surfactant that can be included in the kit is preferably contained at a concentration of not larger than 0.05 v/v % after preparation. The monovalent cation and/or divalent cation-containing salt is preferably contained at a concentration of not larger than 1 mol/liter after preparation.

One embodiment of the kit may be in such a form that a first PI polyamide and/or a second PI polyamide modified with a linker molecule, a carrier modified with a ligand molecule, and necessary reagents are charged into a test tube.

The test tube used in this embodiment is preferably one that is so processed as not to allow a nucleic acid to be adsorbed onto the inside of the test tube. In another embodiment, the inside of the test tube many be modified with ligand molecules. In a further embodiment, the test tube may be a blood collection tube. For example, when the blood of a patient is directly collected using a blood collection tube into which there have been charged the first PI polyamide and/or the second PI polyamide, a carrier modified with a ligand molecule and necessary reagents, the tube can be immediately brought to the concentration of the target double-stranded nucleic acid molecules and also to analytical operations.

7. As to Genes Serving as an Analysis Object

In the embodiments of present invention, although not limited thereto, targetable genes can be those genes serving as a target in the analysis of single nucleotide polymorphism (SNP) in the field of pharmacogenomics (PGx: pharmacogenomics).

It will be noted that the term "family" of gene used herein includes both a superfamily and a subfamily of a specific gene.

In practicing embodiments of the invention, another targetable gene includes RAS and its family, and mutants thereof. The superfamily of RAS includes RHO, RAB, ARF, RAN and subfamilies thereof. The subfamily of RAS includes, for example, K-RAS, N-RAS and H-RAS, the subfamily of RHO includes RHOA, RHOB, RAC1 and CDC42, and the subfamily of RAB includes RAB1, RAB2, RAB3, RAB4 and RAB27 although not limited thereto.

It is preferred to analyze the presence or absence of a mutation in exons 2, 3 and 4 of K-RAS. In the genetic exon 2 of K-RAS, it is preferred to analyze the presence or absence of a mutation of codons 12, 13. As to the exon 3 of the K-RAS gene, it is preferred to analyze the presence or absence of a mutation of codon 61. As to the exon 4 of the K-RAS gene, it is preferred to analyze the presence or absence of a mutation of codons 117 and 146.

It is preferred to analyze the presence or absence of a mutation in the exons 2 and 3 of N-RAS. In the exon 2 of N-RAS, it is preferred to analyze the presence or absence of a mutation of codons 12 and 13. Alternatively, it may be preferred to analyze a mutation of codon 61 in the exon 3 of N-RAS.

Another type of targetable gene in embodiments of the present invention includes cytochrome P450 gene (CYP) and its family, and mutants thereof although not limited thereto. The subfamily of CYP includes, for example, CYP2D6, CYP2C9, CYP2C19, CYP2C, CYP3A4 and CYP3A5 although not limited thereto.

In embodiments of the present invention, a further type of targetable gene includes glutathione-S-transferase (GSTT) and its family, and mutants thereof. The GDTT family includes, for example, GSTT1, GSTTM1 and GSTP1 although not limited thereto.

A still further type of targetable gene includes N-acetylated transferase gene (NAT) and its family, and mutants thereof. Examples of the NAT subfamily include NAT1 and NAT2 although not limited thereto.

Still another type of targetable gene includes thymidylic acid synthetic enzyme (TS) and its family, mutants thereof, and a 3' end untranslated region of TS and a 3' end untranslated region although not limited thereto.

Yet another type of targetable gene includes UDP glucronic acid transferase (UGT) and its family, and mutants thereof. The UGT subfamily includes, for example, UGT1A1 although not limited thereto.

Another type of targetable gene includes excision repair cross-complementing gene (ERCC) and its family, and mutants thereof. The subfamily of ERCC includes, for example, ERCC1 and ERCC2 although no limited thereto.

Another type of targetable gene includes a multidrug resistant gene (MDR) and its family, and mutants thereof although not limited thereto. The subfamily of MDR includes, for example, MDR1 and MDR2 although not limited thereto.

Another type of targetable gene includes a gene repair protein (XRCC) and its family, and mutants thereof. The subfamily of XRCC includes, for example, XRCC1 and XRCC5 although not limited thereto.

Another type of targetable gene includes a corticotropin-releasing hormone receptor protein gene (CRHR) and its family, and mutants thereof. The subfamily of MDR includes, for example, CRHR1 and CRHR2 although not limited thereto.

Another type of targetable gene includes a breast cancer suppressor gene (BRCA) and its family, and mutants thereof. The subfamily of BRCA includes, for example, BRCA1 and BRCA2 although not limited thereto.

Another type of targetable gene includes tumor suppressor gene (MSH) and its family, and mutants thereof although not limited thereto. The family of MSH includes, for example, RB, p53, APC, NF1, NF2, WT1, VHL, BRCA, CHEK2, MASPIN, P73, DPC4 (SMAD4), MSH1, MSH2, MSH6, MLH1, PMS2, DCC, PTEN, SDHD, P16, P57KIP2, PTC, TSC1, TSC2, EXT1 and EXT2 genes although not limited thereto.

Another type of targetable gene includes the genes, and their families, selected from the group consisting of gemcitabine metabolizing enzyme gene (CDA), dihydropyrimidine dehydrogenase gene (DPD), methylenetetrahydrofolate reductase gene (MTHFR), orotate phosphoribosyl trasnferase gene (OPRT), serotonin transporter gene (5-HTT), blood coagulation factor V gene (Factor V), vitamin K epoxide reductase complex 1 gene (VKORC1), APEX1, DCK, DPYD, TYMP, MLH1, UMPS, PCNA, POLA, RRM1, SLC29A1, TK1, UNG, ACTB, AKT1, ALK, APC, BRAF, CHD1, CTNNB1, EGFR, ERBB2, FBXW7, FGFR2, FOXL2, GNAQ, GNAS, KIT, MAP2K1, MET, NRAS, PDGFRA, PIK3CA, PTEN, SMAD4, SRC, STK11 and TP53, and mutants of the gene selected from these genes.

Besides, targetable genetic groups include genetic groups serving as an inspection object in the diagnosis prior to birth, genes known as genetic diseases, and genetic groups associated with diseases that are related with the variation and denaturation of proteins such as Alzheimer disease.

Another type of targetable gene includes an MLH1 gene and its family, and mutants thereof although not limited thereto. The analysis region of the MLH1 gene is preferably exon 1-exon 19.

Another type of targetable gene includes an MSH2 gene and its family, and mutants thereof although not limited thereto. The analysis region of the MSH2 gene is preferably exon 1-exon 16.

Another type of targetable gene includes an MSH6 gene and its family, and mutants thereof although not limited thereto. The analysis region of the MSH6 gene is preferably exon 1-exon 10.

Another type of targetable gene includes a PMS2 gene and its family, and mutants thereof although not limited thereto. The analysis region of the PMS2 gene is preferably exon 1-exon 15.

Another type of targetable gene includes an APC gene and its family, and mutants thereof although not limited thereto. The analysis region of the APC gene is preferably exon 1-exon 15.

Another type of targetable gene includes an MEN1 gene and its family, and mutants thereof although not limited thereto. The analysis region of the MEN1 gene is preferably exon 2-exon 10.

Another type of targetable gene includes an RET gene and its family, and mutants thereof although not limited thereto. The analysis region of the RET gene is preferably exon 10, exon 11, and exon 13-exon 15. It is more preferred to analyze the presence or absence of A883F in the exon 15 of the RET gene, or the presence or absence of the mutation of M918 or S992S.

Another type of targetable gene includes a TP53 gene and its family, and mutants thereof. The analysis region of the TP53 gene is preferably exon 1-exon 11 although not limited thereto.

Another type of targetable gene includes an EGFR gene and its family, and mutants thereof although not limited thereto. The analysis region of the EGFR gene is preferably exon 18-exon 21. It is more preferred to analyze the presence or absence of a mutation in S492R of the EGFR gene.

Another type of targetable gene includes a BRAF gene and its family, and mutants thereof although not limited thereto. The analysis region of the BRAF gene is preferably exon 15. It is more preferred to analyze the presence or absence of a mutation of V500E or K in the exon 15 of the BRAF gene.

Another type of targetable gene includes a c-kit gene and its family, and mutants thereof although not limited thereto. The analysis region of the c-kit gene is preferably exons 9, 11, 13 and 17.

Another type of targetable gene includes a PDGFRα gene and its family, and mutants thereof although not limited thereto. The analysis region of the PDGFRα gene preferably includes exons 12 and 18.

Another type of targetable gene includes a PDGFR gene and its family, and mutants thereof although not limited thereto. The analysis region of the PDGFR gene preferably includes exon 14.

Another type of targetable gene includes a TP53 gene and its family, and mutants thereof although not limited thereto. The analysis region of the TP53 gene preferably includes exons 5 to 8.

EXAMPLES

The present invention will be particularly described by way of examples, which should not be construed as limiting the invention thereto.

Example 1: Concentration of Target Double-Stranded Nucleic Acid Molecules Using a First PI Polyamide Using three samples including a sample A wherein target double-stranded nucleic acid molecules and non-target double-stranded nucleic acid molecules, which had a base sequence difference indicated in Table 1, were set at 5000 molecules:$5\times10^5$ molecules (i.e. the content of the target double-stranded nucleic acid molecules in the sample was 1%), a sample B set at 500 molecules:$5\times10^5$ molecules (i.e. the content of the target double-stranded nucleic acid molecules in the sample was 0.1%), and a sample C set at 50 moles: $5\times10^5$ molecules (i.e. the content of the target double-stranded nucleic acid molecules in the sample was 0.01%), an inventive first PI polyamide having a sequence capable of binding to the target double-stranded nucleic acid molecules shown in FIG. 17, and a carrier related to an embodiment of the invention and made of streptavidin labeled magnetic beads (Magnosphere™ MS300/Streptavidin, manufactured by JSR Life Sciences Inc.), the target double-stranded nucleic acid molecules were concentrated according to a method of the second embodiment of invention selected among the concentration methods of target double-stranded nucleic acid molecules according to embodiments of the present invention. Restriction enzyme-treated plasmid DNA was used as the double-stranded nucleic acid molecule.

It will be noted that the base sequence of sequence No. 1 of the base sequences indicated in Table 1 shows a base sequence (only a bind related portion) at the site of a sense side of the target double-stranded nucleic acid molecule, to which the first PI polyamide related to an embodiment of the invention is bound. The base sequence of sequence No. 2 of the base sequences indicated in Table 1 shows a base sequence (only a bind related portion) at the site of a sense side of the non-target double-stranded nucleic acid molecule, to which the second PI polyamide related to an embodiment of the invention is bound, (which applies hereinafter in the following description). Needless to say, whether either of the double-stranded nucleic acid molecules is aimed at as a target varies depending on the purpose. Although depending on an intended purpose, it may be possible to take the target double-stranded nucleic acid molecule of Table 1 as a non-target double-stranded nucleic acid molecule and the non-target double-stranded nucleic acid molecule of Table 1 as a target double-stranded nucleic acid molecule.

The base sequence at the antisense side of Table 1 is omitted, (which applies hereinafter).

It will be noted that the target double-stranded nucleic acid molecule in this example corresponds to a base sequence of K-RAS codon 12G12V mutation type and the non-target double-stranded nucleic acid molecule corresponds to a base sequence of K-RAS codon 12 wild type. Initially, a first PI polyamide equivalent to $1\times10^7$ molecules was added to the respective samples and well mixed, followed by incubation for 60 minutes. Thereafter, 100 μg of streptavidin labeled magnetic beads was added, followed by incubation for 60 minutes under mixing with a tube rotator. After the incubation, the streptavidin labeled magnetic beads and a liquid component were separated from each other by use of a magnetic stand.

TABLE 1

| | Base sequence | Sequence No. |
|---|---|---|
| Target double-stranded nucleic acid molecule (sense side) | 5'-GTTGGC-3' | 1 |
| Non-Target double-stranded nucleic acid molecule (sense side) | 5'-GGTGGC-3' | 2 |

Assuming that the target double-stranded nucleic acid molecules were bound to the thus separated streptavidin labeled magnetic beads, 20 μl of a TE buffer dispersion was added for use as an analysis sample. The analysis sample was subjected to measurement of a content of the target double-stranded nucleic acid molecules in the analysis sample by use of a commercially available reagent kit for droplet digital PCR (Prime PCR for ddPCR, manufactured by BIO-RAD, Inc.) and a droplet digital PCR system (QX 100™ droplet digital PCR, manufactured by BIO-RAD, Inc.), from which a concentration efficiency (fold) (content (%) of the target double-stranded nucleic acid molecules after concentration/content (%) of the target double-stranded nucleic acid molecules in the respective samples) was calculated.

TABLE 2

| Sample | Content (%) | Concentration efficiency (fold) |
|---|---|---|
| A | 100 | 100 |
| B | 100 | 1000 |
| C | 14.3 | 1430 |

The results of the measurement of Table 2 reveal that when using the concentration method of target double-stranded nucleic acid molecules according to an embodiment of in the present invention, the sample A (wherein the content of the target double-stranded nucleic acid molecules in the sample was 1%) was concentrated to 100%, meaning that 100-fold concentration was achieved when compared with prior to the concentration. Next, the sample B (wherein the content of the target double-stranded nucleic acid molecules in the sample was 0.1%) was concentrated to 100%, meaning that 1000-fold concentration was achieved when compared with prior to the concentration. Next, the sample C (wherein the content of the target double-stranded nucleic acid molecules in the sample was 0.01%) was concentrated to 14.3% and thus, the 1430-fold concentration was achieved when compared with prior to the concentration. From this, it has been made clear that the one-base difference is discriminated by the concentration method according to an embodiment of the invention using the inventive first PI polyamide, so that the target double-stranded nucleic acid molecules are recovered from the sample and the 1430-fold concentration in maximum can be achieved.

Example 2: Concentration of Target Double-Stranded Nucleic Acid Molecules by Use of a Second PI Polyamide Using a sample D indicated in Table 1 and containing target double-stranded nucleic acid molecule and non-target double-stranded nucleic acid molecule at 100 molecules:$10^4$ molecules (wherein the content of the target double-stranded nucleic acid molecules in the sample was 0.1%), an inventive second PI polyamide shown in FIG. 17, which had a sequence capable of binding to non-target double-stranded nucleic acid molecules and an inventive carrier made of streptavidin labeled magnetic beads (Magnosphere™ MS300/Streptavidin, manufactured by JSR Life Sciences, Inc.), the target double-stranded nucleic acid molecules were concentrated according to the steps 1 to 5 of the fifth embodiment of invention in the inventive concentration method of target double-stranded nucleic acid molecules. Restriction enzyme-treated plasmid DNA was used as the double-stranded nucleic acid molecule. First, the second PI polyamide equivalent to $1\times10^7$ molecules and 100 μg of the streptavidin labeled magnetic beads were added and incubated for 60 minutes while mixing with a tube rotator. Next, a magnetic stand was used to separate the streptavidin labeled magnetic beads and a liquid component from each other. Thereafter, the sample D was added to the streptavidin labeled magnetic beads bound with the second PI polyamide and incubated for 60 minutes while mixing with a tuber rotator. After the incubation, a magnetic stand was used to separate the streptavidin labeled magnetic particles and a liquid component from each other.

It was assumed that the target double-stranded nucleic acid molecules were left in the separated liquid component, which was thus provided as an analysis sample. The analysis sample was subjected to measurement of a content (%) of the target double-stranded nucleic acid molecules in the analysis sample of the target double-stranded nucleic acid molecules and the non-target double-stranded nucleic acid by use of a commercially available reagent kit for droplet digital PCR (Prime PCR for ddPCR, manufactured by BIO-RD Inc.) and a droplet digital PCR system (QX 100™ droplet digital PCR, manufactured by BIO-RAD Inc.), from which a concentration effect (fold) (content (%) of the target double-stranded nucleic acid molecules after concentration/content (%) of the target double-stranded nucleic acid molecules in the sample) was calculated.

TABLE 3

| Sample | Content (%) | Concentration efficiency (fold) |
|---|---|---|
| D | 15 | 15 |

The results of the measurement of Table 3 reveal that when using the concentration method of the target double-stranded nucleic acid molecules in embodiments of the present invention, the sample D (wherein the content of the target double-stranded nucleic acid molecules in the sample was 1%) was concentrated to 15.0% and thus, 15-fold concentration was achieved when compared with prior to the concentration. From this, it was demonstrated that according the concentration method of target double-stranded nucleic acid molecules using the second PI polyamide according to an embodiment of the present invention, 15-fold concentration could be realized by discriminating a one-base difference and removing the non-target double-stranded nucleic acid molecules from the sample.

Example 3: Concentration [1] of Target Double-Stranded Nucleic Acid Molecules Using a First PI Polyamide and a Second PI Polyamide Using a sample (sample E) wherein target double-stranded nucleic acid molecules and non-target double-stranded nucleic acid molecules having a base sequence difference indicated in Table 4 were set at 500 molecules: $5\times10^5$ molecules (wherein the content of the target double-stranded nucleic acid molecules in the sample was 0.1%), inventive first PI polyamide and second PI polyamide shown in FIGS. 17 and 18, respectively, and an inventive carrier made of streptavidin labeled magnetic beads (Magnosphere™ MS300/Streptavidin, manufactured by JSR Life Sciences, Inc.), the concentration of the target double-stranded nucleic acid molecules was carried out through a combination of the steps 1 to 3 of the fifth embodiment of invention and the steps 1 to 5 of the third embodiment of invention in the inventive concentration method of target double-stranded nucleic acid molecules. The double-stranded nucleic acid molecule used was a restriction enzyme-treated plasmid DNA. It will be noted that the target double-stranded nucleic acid molecule in this example corresponded to a base sequence of K-RAS codon 13G13D mutation type and the non-target double-stranded nucleic acid molecules corresponded to a base sequence of K-RAS codon 12 wild-type. First, the second P1 polyamide equivalent to $1\times10^7$ molecules shown in FIG. 17 was added to the sample E, followed by incubation for 30 minutes while mixing with a tube rotator. The procedure of the above steps corresponds to the fifth embodiment of invention in the inventive concentration method of target double-stranded nucleic acid molecules.

Then, 100 μg of the streptavidin labeled magnetic beads was added to the first PI polyamide equivalent to $1\times10^7$ molecules shown in FIG. 19, followed by incubation for 60 minutes while mixing with a tube rotator. After the incubation, a magnetic stand was used to separate the streptavidin labeled magnetic beads and a liquid component from each other. The thus separated first PI polyamide-bound streptavidin labeled magnetic beads were added, as a whole, to the mixture of a second PI polyamide and the sample E, and incubated for 60 minutes while mixing with a tube rotator. After the incubation, a magnetic stand was used to separate the streptavidin labeled magnetic beads and a liquid component from each other. The procedure of the above steps corresponds to the third embodiment of invention in the inventive concentration method of target double-stranded nucleic acid molecules.

TABLE 4

| | Base sequence | Sequence No. |
|---|---|---|
| Target double-stranded nucleic acid molecules (sense side) | 5'-GGTGAC-3' | 3 |
| Non-target double-stranded nucleic acid molecules (sense side) | 5'-GGTGGC-3' | 2 |

Assuming that the target double-stranded nucleic acid molecules were bound to the thus separated streptavidin labeled magnetic beads, 20 μl of a TE buffer dispersion was added thereto for use as an analysis sample. The analysis sample was subjected to measurement of a content (%) of the target double-stranded nucleic acid molecules in the analysis sample by use of a commercially available reagent kit for droplet digital PCR (Prime PCR for ddPCR, manufactured by BOP-RAD, Inc.) and a droplet digital PCR system (QX 100™ droplet digital PCR, manufactured by BIO-RAD Inc.), from which a concentration effect (fold) (i.e. a content (%) of the target double-stranded nucleic acid molecules after concentration/a content (%) of target double-stranded nucleic acid molecules in the sample) was calculated. For reference data, in the inventive concentration method of target double-stranded nucleic acid molecules but using a first PI polyamide alone shown in FIG. 19, the target double-stranded nucleic acid molecules were concentrated by a combination of the steps 1 to 3 of the fifth embodiment of invention and the steps 1 to 5 of the third embodiment of invention to measure the content (%) of the target double-stranded nucleic acid molecules to obtain the results of the measurement and a calculated concentration effect (fold) only for comparison.

TABLE 5

| Sample | Type of data | Content (%) | Concentration efficiency (fold) |
|---|---|---|---|
| E | Measured data | 50 | 500 |
|   | Reference data | 33.4 | 334 |

The measured data of the results of the measurement in Table 5 reveal that when using the concentration method of target double-stranded nucleic acid molecules using a combination of the first PI polyamide and the second PI polyamide according to embodiments of in the present invention, the sample E (wherein the content of the target double-stranded nucleic acid molecules in the sample was 0.1%) was concentrated to 50.0%, thereby achieving 500-fold concentration when compared with prior to the concentration. From this, it has been revealed that according to the concentration method of target double-stranded nucleic acid molecules, which makes use of the first PI polyamide and the second PI polyamide in combination and in which the steps 1 to 3 of the fifth embodiment of invention and the steps 1 to 5 of the third embodiment of invention are used in combination, the target double-stranded nucleic acid molecules can be captured and concentrated to 500 fold while discriminating the one-base difference and reducing miscapturing of the non-target double-stranded nucleic acid molecules from the sample.

The comparison between the reference data and the measured data of the results of the measurement in Table 5 demonstrates that when compared with the concentration method of target double-stranded nucleic acid molecules using only the inventive first PI polyamide, the use of the concentration method of the target double-stranded nucleic acid molecules wherein the first PI polyamide and the second PI polyamide are used in combination in the practice of embodiments of the invention and the steps 1 to 3 of the fifth embodiment of invention and the steps 1 to 5 of the third embodiment of invention are combined, leads to about 1.5-fold improvements in the content (%) of the target double-stranded nucleic acid molecules and the concentration effect.

Example 4: Concentration (2) of Target Double-Stranded Nucleic Acid Molecules Using a First PI Polyamide and a Second PI Polyamide in Combination Using a sample F containing target double-stranded nucleic acid molecules and non-target double-stranded nucleic acid molecules that differed from each other in base sequence shown in Table 4 and had an amount ratio of 100 molecules:$1 \times 10^4$ (wherein the content of the target double-stranded nucleic acid molecules in the sample was 1%), a sample G having an amount ratio of 10 molecules:$1 \times 10^4$ molecules (wherein the content of the target double-stranded nucleic acid molecules in the sample was 0.1%) and a sample H having an amount ratio of 5 molecules:$5 \times 10^4$ molecules (wherein the content of the target double-stranded nucleic acid molecules in the sample was 0.01%), inventive first P1 polyamide and second P1 polyamide shown in FIGS. 18 and 19, and an inventive carrier made of streptavidin labeled magnetic beads (Magnosphere™ MS300/Streptavidin, manufactured by JSR Life Sciences, Inc.), the concentration of the target double-stranded nucleic acid molecules was performed by the combination of the steps 1 to 5 of the fifth embodiment of invention and the steps 1 to 5 of the third embodiment of invention. The target double-stranded nucleic acid molecules used were those of restriction enzyme-treated plasmid DNA. Initially, the second PI polyamide equivalent to $11 \times 10^7$ molecules shown in FIG. 18 was added to the respective samples and incubated for 60 minutes while mixing with a tuber rotator. Thereafter, 100 μg of streptavidin labeled magnetic beads was added, followed by incubation for 60 minutes while mixing with a tuber rotator. After the incubation, a magnetic stand was used to separate the streptavidin labeled magnetic beads and a liquid component from each other. The liquid component was provided as a treated sample in a subsequent step. The above procedure corresponded to the steps 1 to 5 of the fifth embodiment of invention in the inventive concentration method of target double-stranded nucleic acid molecules.

Figure 20:
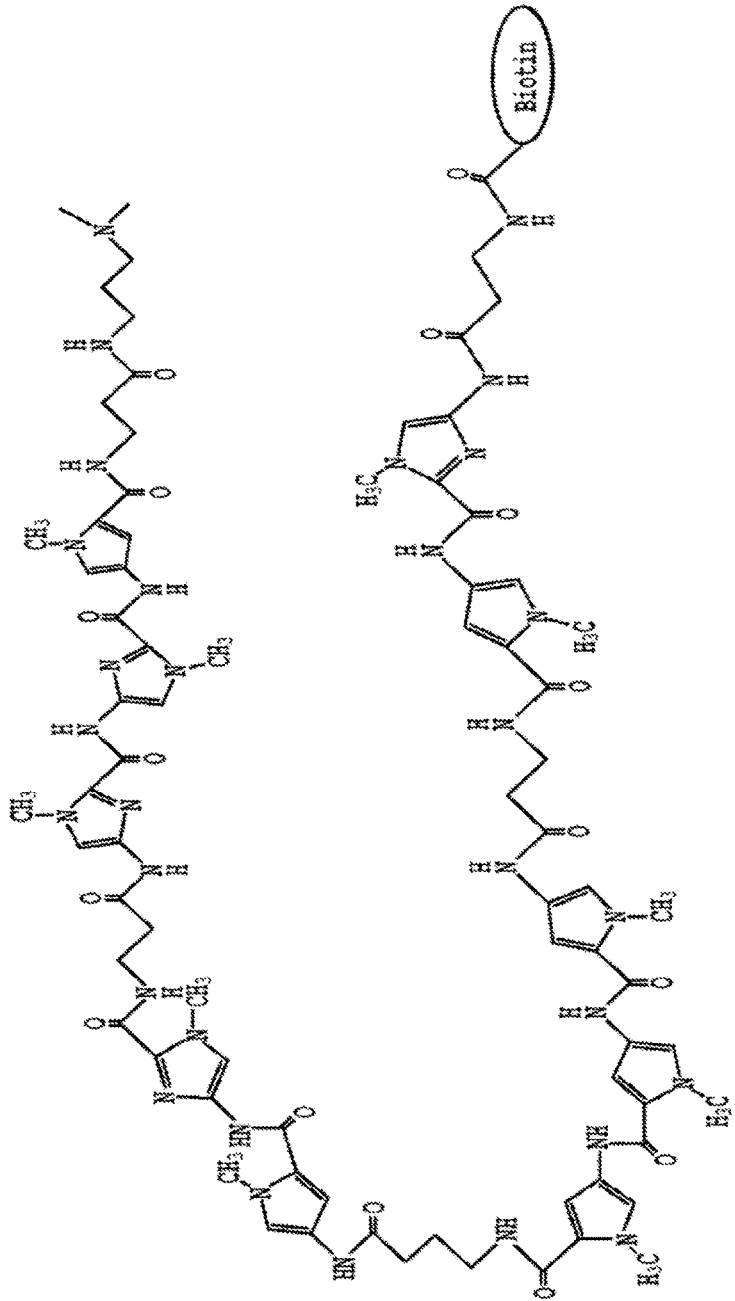
FIG. 20 is a schematic view showing a sequence of a pyrrole-imidazole-containing polyamide bound with a target double-stranded nucleic acid molecule and its structural formula according to an embodiment of the invention.

Next, 100 μg of streptavidin labeled magnetic beads was added to the first PI polyamide equivalent to $1 \times 10^7$ molecules shown in FIG. 20 and incubated for 60 minutes while mixing with a tube rotator. After the incubation, a magnetic stand was used to separate the streptavidin labeled magnetic beads and a liquid component from each other. All of the streptavidin labeled magnetic beads bound with the thus separated PI polyamide were added to the treated sample, followed by incubation for 60 minutes while mixing with a tube rotator. After the incubation, a magnetic stand was used to separate the streptavidin labeled magnetic beads and a liquid component. The above procedure corresponded to the step 1 to 5 of the third embodiment of invention in the inventive concentration method of target double-stranded nucleic acid molecules.

Assuming that the target double-stranded nucleic acid molecules were bound to the thus separated streptavidin labeled magnetic beads, 20 μl of a TE buffer dispersion was added thereby providing an analysis sample. The analysis sample was subjected to measurement of a content (%) of the target double-stranded nucleic acid molecules in the analysis sample by use of a commercially available reagent kit for droplet digital PCR (Prime PCR for ddPCR, manufactured by BIO-RAD, Inc.) and a droplet digital PCR system (QX 100™ droplet digital PCR, manufactured by BIO-RAD, Inc.). From this, the concentration effect (fold) (the content (%) of the target double-stranded nucleic acid molecules after concentration/the content (%) of the target double-stranded nucleic acid molecules in the respective samples) was calculated. For reference data, using the first PI polyamide alone shown in FIG. 20, the combination steps of the fifth embodiment of invention and the third embodiment of invention in the inventive concentration method of target double-stranded nucleic acid molecules were performed for the concentration of the target double-stranded nucleic acid molecules to obtain the results of measurement of the content (%) of the target double-stranded nucleic acid molecules and calculate the concentration effect (fold) only for comparison.

TABLE 6

| Sample | Type of data | Content (%) | Concentration efficiency (fold) |
|---|---|---|---|
| F | Measured data | 100 | 100 |
|   | Reference data | 24.1 | 24 |
| G | Measured data | 100 | 1000 |
|   | Reference data | 33.4 | 334 |
| H | Measured data | 50 | 5000 |
|   | Reference data | 9.1 | 910 |

The results of the measurement in Table 6 reveal that the sample F (wherein the concentration of the target double-stranded nucleic acid molecules in the sample was 1%) was concentrated to 100.0% and 100-fold concentration was achieved when compared with prior to the concentration. Next, the sample G (wherein the content of the target double-stranded nucleic acid molecules in the sample was 0.1%) was concentrated to 100.0% and 1000-fold concentration was achieved when compared with prior to the concentration. The sample H (wherein the content of the target double-stranded nucleic acid molecules in the sample was 0.01%) was concentrated to 50.0% and 5000-fold concentration was achieved when compared with prior to the concentration. In view of the above, it has been revealed that according to the concentration method of target double-stranded nucleic acid molecules using the first PI polyamide and the second PI polyamide in combination and also using a combination of the steps 1 to 5 of the fifth embodiment of invention and the steps 1 to 5 of the third embodiment of invention, a one-base difference can be discriminated and thus, the non-target double-stranded nucleic acid molecules can be removed from the samples and the target double-stranded nucleic acid molecules can be captured thereby enabling 5000-fold concentration in maximum.

The comparison between the reference data and the measured data of the results of the measurement in Table 6 reveals that when compared with the concentration method of target double-stranded nucleic acid molecules using the first PI polyamide alone, the use of the concentration method of target double-stranded nucleic acid molecules wherein the first PI polyamide and the second PI polyamide are used in combination and the steps 1 to 5 of the fifth embodiment of invention and the steps 1 to 5 of the third embodiment of invention are combined enables the content (%) and concentration effect (fold) of the target double-stranded nucleic acid molecules to be improved approximately 4.2-fold for the sample F, about 3-fold for the sample G and approximately 5.5-fold for the sample H.

It has been demonstrated that when compared with the inventive concentration method of target double-stranded nucleic acid molecules in the foregoing Example 3 using the first P1 polyamide and the second P1 polyamide and a combination of the steps 1 to 3 of the fifth embodiment of invention and the steps 1 to 5 of the fifth embodiment of invention (i.e. the comparison between the measured data of the sample E of Example 3 and the measured data of the sample G of Example 4) and also with the concentration method of target double-stranded nucleic acid molecules using the first PI polyamide alone, the use of the concentration method of target double-stranded nucleic acid molecules using the first PI polyamide and the second PI polyamide and a combination of the steps 1 to 5 of the fifth embodiment of invention and the steps 1 to 5 of the fifth embodiment of invention enables the content (%) and condensation effect (fold) of the target double-stranded nucleic acid molecules to be improved approximately 2.0-fold.

Example 5: Concentration of Target Double-Stranded Nucleic Acid Molecules in Blood Serum/Plasma Using a First PI Polyamide Using a sample I obtained by adding, to a normal person serum, target double-stranded nucleic acid molecules and non-target double-stranded nucleic acid molecules with a base sequence difference shown in Table 1 and also with an amount ratio of 500 molecules:5×10$^5$ molecules (wherein the content of the target double-stranded nucleic acid molecules in the sample was 0.1%) and a sample J obtained by adding, to a normal person blood plasma, both types of molecules with an amount ratio of 500 molecules:5×10$^5$ molecules (wherein the content of the target double-stranded nucleic acid molecules in the sample was 0.1%), inventive first PI polyamide having a sequence capable of binding to the target double-stranded nucleic acid molecules shown in FIG. 17, and an inventive carrier made of streptavidin labeled magnetic beads (Magnosphere™ MS300/Streptavidin, manufactured by JSR Life Sciences, Inc.), the concentration of the target double-stranded nucleic acid molecules was performed according to the method of the second embodiment of invention in the inventive concentration method of target double-stranded nucleic acid molecules. The double-stranded nucleic acid molecules used were those of restriction enzyme-treated plasmid DNA. Initially, a first PI polyamide equivalent to 1×10$^7$ molecules was added to the respective samples and well mixed, followed by incubation for 60 minutes, Thereafter, 100 μg of streptavidin labeled magnetic beads was added to the mixture and incubated for 60 minutes while mixing with a tube rotator. After the incubation, a magnetic stand was used to separate the streptavidin labeled magnetic beads and a liquid component from each other.

Assuming that the target double-stranded nucleic acid molecules were bound to the thus separated streptavidin labeled magnetic beads, 20 μl of a TE buffer dispersion was added thereto so as to provide an analysis sample. Using a commercially available reagent kit for droplet digital PCR (Prime PCR for ddPCR, manufactured by BIO-RAD, Inc.) and a droplet digital PCR system (QX 100™ droplet digital PCR, manufactured by BIO-RAD, Inc.), the content (%) of the target double-stranded nucleic acid molecules in the respective samples was measured, from which the concentration effect (fold) (the content (%) of the target double-stranded nucleic acid molecules after concentration/the content (%) of the target double-stranded nucleic acid molecules in the respective samples) was calculated.

TABLE 7

| Sample | Content (%) | Concentration efficiency (fold) |
|---|---|---|
| I | 6.6 | 66 |
| J | 9.8 | 98 |

The results of the measurement in Table 7 reveal that when using the inventive concentration method of the target double-stranded nucleic acid molecules, the sample I (wherein the content of the target double-stranded nucleic acid molecules in the sample was 0.1%) was concentrated to 6.6% and thus, 66-fold concentration was achieved when compared with prior to the concentration. The sample J (wherein the content of the target double-stranded nucleic acid molecules in the sample was 0.1%), was concentrated to 9.8% and thus, 98-fold concentration was achieved when compared with prior to the concentration. From this, it will be seen that according to the inventive concentration method of target double-stranded nucleic acid molecules using a first PI polyamide, a one-base difference is discriminated and the target double-stranded nucleic acid molecules are recovered from the blood serum or plasma sample thereby enabling 66 or 98-fold concentration. Moreover, the above results reveal that according to the inventive concentration method of target double-stranded nucleic acid molecules, target double-stranded nucleic acid molecules can be recovered and concentrated directly from a liquid biopsy (blood serum, blood plasma or urine) without resorting to a nucleic acid purifying step.

Example 6: Effect of Repeated Concentration (in the Case of Forming Complex A) Using a First PI Polyamide There were used a sample K wherein target double-stranded nucleic acid molecules and non-target double-stranded nucleic acid molecules, which had base sequences different from each other as shown in Table 8), had a ratio of 50 molecules:$5 \times 10^5$ molecules (wherein the content of the target double-stranded nucleic acid molecules in the sample was 0.01%), an inventive first polyamide shown in FIG. 17, and streptavidin labeled magnetic beads (Magnosphere™ MS300/Streptavidin, manufactured by JSR Life Sciences, Inc.) as a carrier. The double-stranded nucleic acid molecules used were those of restriction enzyme-treated plasmid DNA. It will be noted that the target double-stranded nucleic acid molecule corresponds to a base sequence of K-RAS codon 12G12V mutation type, and the non-target double-stranded nucleic acid molecule corresponds to a base sequence of K-RAS codon 12 wild-type.

Example 6-1

<Formation of Complex a Through the Formation of Complex a1>
1. Formation of Complex a1
A first PI polyamide equivalent to $1 \times 10^7$ molecules was added to a microtube in
which sample K had been placed, and incubated for 10 minutes at room temperature while mixing with a tube rotator, thereby forming a complex (complex a1) of the PI polyamide and the streptavidin labeled magnetic beads.
2. Repeated Formation of Complex A
100 µg of streptavidin labeled magnetic beads was added to the microtube in which the complex a1 had been placed, and incubated for 60 minutes at room temperature while mixing with a tube rotator to form a complex A by binding between the complex a1 and the streptavidin labeled magnetic beads. After the incubation, a magnetic stand was used for separation into a liquid component and a complex A-1. 100 µg of streptavidin labeled magnetic beads were freshly added to the separated liquid component, followed by performing the same operations as described above and separation into the complex A and a liquid component. The above operations were repeated three times to obtain three sets of the complexes A (complex A-1, complex A-2 and complex A-3 obtained in this order).
3. Quantitative Analysis
All the separated complexes A were transferred to one tube, to which 20 µl of a TE buffer dispersion was added so as to provide an analysis sample. The analysis sample was subjected to measurement of a content (%) of the target double-stranded nucleic acid molecules in the analysis sample by use of a commercially available reagent kit for droplet digital PCR (Prime PCR for ddPCR, manufactured by BIO-RD Inc.) and a droplet digital PCR system (QX 100™ droplet digital PCR, manufactured by BIO-RAD Inc.), from which a concentration effect (fold) (the content (%) of the target double-stranded nucleic acid molecules after concentration/content (%) of the target double-stranded nucleic acid molecules in the sample) was calculated. It will be noted that the results of the case that the complex A-1 alone was provided as an analysis sample were used only for comparison.

The results of the measurement are shown in Table 9. In the inventive concentration method of target double-stranded nucleic acid molecules using the first PI polyamide, the repetition of the formation and separation steps of the complex A by using the complex a1 and the streptavidin labeled magnetic beads lead to 7.2% and thus, 720-fold concentration was achieved when compared with prior to the concentration (the content of the target double-stranded nucleic acid molecules in the sample was 1%). When compared with the case that the formation step of the complex A was performed only one time (with a content of 3.3% and a concentration effect (fold) of 330-fold), the concentration effect was increased to about 2-fold.

TABLE 8

| | Base sequence | Sequence No |
|---|---|---|
| Target double-stranded nucleic acid molecule (sense side) | 5'-GTTGGC-3' | 1 |
| Non-target double-stranded nucleic acid molecule (sense side) | 5'-GTGGGC-3' | 2 |

TABLE 9

| Sample | Type of data | Content (%) | Concentration effect (fold) |
|---|---|---|---|
| K | Repeated three times | 7.2 | 720 |
| | Repeated once | 3.3 | 330 |

Example 6-2

<Formation of Complex a Through the Formation of Complex a2>
1. Formation of Complex a2
A first PI polyamide equivalent to $1 \times 10^7$ molecules and 100 µg of streptavidin
magnetic beads were mixed in a microtube and incubated for 30 minutes at room temperature while mixing with a tube rotator to form a complex (complex a2) of the first PI polyamide and the streptavidin labeled magnetic beads. After the incubation, a magnetic stand was used for separation into a liquid component and the complex a2. A first PI polyamide equivalent to $1 \times 10^7$ equivalent molecules and 100 µg of streptavidin labeled magnetic beads were freshly added to the thus separated liquid component, followed by repeating the same operations as described above to separate a complex a2. The above operations were repeated three times to provide three sets of the complexes a2 (complex a2-1, complex a2-2 and complex a2-3 obtained in this order).
2. Repeated Formation of Complex A
(2-1) The complex a2-1 was added to a microtube, in which the sample K had been placed, and incubated for 60 minutes while mixing with a tube rotator to form a complex A-1. After the incubation, a magnetic stand was used for separation into a liquid component and the complex A-1.

(2-2) The complex a2-2 and the complex a2-3 prepared in the liquid components as described out above were, respectively, used for repeating the same procedure as in (2-1) to form and separate complexes A-2 and A-3.

3. Quantitative Analyses

20 μl of a TE buffer dispersion was added to all the separated complexes A to provide an analysis sample in the form of a dispersion. The analysis sample was subjected to measurement of a content (%) of the target double-stranded nucleic acid molecules therein by use of a commercially available reagent kit for droplet digital PCR (Prime PCR for ddPCR, manufactured by BIO-RD Inc.) and a droplet digital PCR system (QX 100™ droplet digital PCR, manufactured by BIO-RAD Inc.), from which a concentration effect (fold) (the content (%) of the target double-stranded nucleic acid molecules after concentration/the content (%) of the target double-stranded nucleic acid molecules in the sample) was calculated. It will be noted that the results of the case that the complex A-1 alone was used as an analysis sample are shown only for comparison.

The results of the measurement are shown in Table 10. In the inventive concentration method of target double-stranded nucleic acid molecule using the first PI polyamide, when the steps of forming and separating the complex A by mixing of the complex a2 and the sample are repeated, the content increases to 15.6%, thus concentrated to 1560-fold when compared to prior to the concentration (the content of the target double-stranded nucleic acid molecules in the sample is 1%). The concentration effect is increased to about 3-fold when compared with the case where the formation step of the complex A is performed once (with a content of 5.4% and a concentration effect (fold) of 540-fold).

TABLE 10

| Sample | Type of data | Content (%) | Concentration effect (fold) |
|---|---|---|---|
| K | Repeated three times | 15.6 | 1560 |
|   | Repeated once | 5.4 | 340 |

These results reveal that when the step of forming the complex A by mixing the complex a2 and the sample in the concentration method of target double-stranded nucleic acid molecules using the first PI polyamide, or the step of forming the complex A by mixing the complex a1 and the carrier a (streptavidin labeled magnetic beads) is repeated, the target double-stranded nucleic acid molecules can be more concentrated.

Example 7: Effect of Repeated Concentration (in the Case of Forming a Complex B) Using a Second PI Polyamide A sample L, shown in Table 8, containing target double-stranded nucleic acid molecules and non-target double-stranded nucleic acid molecules, which had base sequences different from each other and had a ratio of 100 molecules: $1 \times 10^4$ molecules (with a content of the target double-stranded nucleic molecules in the sample being 1%), an inventive second PI polyamide shown in FIG. 18, and an inventive carrier made of streptavidin labeled magnetic beads (Magnosphere™ MS300/Streptavidin, manufactured by JSR Life Sciences, Inc.) were used to carry out the concentration. Restriction enzyme-treated plasmid DNA was used as the double-stranded nucleic acid molecule.

Example 7-1

<Formation of Complex B Through the Formation of Complex b1>

(1) Formation of Complex b1

A second PI polyamide equivalent to $1 \times 10^7$ molecules was added to a microtube wherein the sample L had been placed and subsequently incubated at room temperature for 60 minutes while mixing with a tube rotator to form a complex (complex b1) between the second PI polyamide and the streptavidin labeled magnetic beads.

2. Repeated formation of complex B

100 μs of streptavidin labeled magnetic beads was added to a microtube wherein the complex b1 had been placed, and incubated at room temperature for 60 minutes while mixing with a tube rotator to form a complex B by binding between the complex b1 and the streptavidin labeled magnetic beads. After the incubation, a magnetic stand was used for separation into a liquid component and a complex B-1. 100 μg of fresh streptavidin labeled magnetic beads was added to the thus separated liquid component, followed by repeating the operations in a manner as described above and separating a complex B. Likewise, the above operations were repeated three times and thus, 3 sets of complexes B (complex B-1, complex B-2 and complex B-3 obtained in this order) were prepared.

3. Quantitative Analyses

The liquid components separated above were provided as an analysis sample. The analysis sample was subjected to measurement of a content (%) of the target double-stranded nucleic acid molecules in the analysis sample by use of a commercially available reagent kit for droplet digital PCR (Prime PCR for ddPCR, manufactured by BIO-RD Inc.) and a droplet digital PCR system (QX 100™ droplet digital PCR, manufactured by BIO-RAD Inc.), from which a concentration effect (fold) (the content (%) of the target double-stranded nucleic acid molecules after concentration/the content (%) of the target double-stranded nucleic acid molecules in the sample) was calculated. It will be noted that the results of the case that the liquid component after the separation of the complex B-1 was provided as an analysis sample are shown only for comparison.

The results of the measurement are shown in Table 11. In the inventive concentration method of target double-stranded nucleic acid molecule using the first PI polyamide, when the steps of forming and separating the complex B by mixing of the complex b1 and the streptavidin labeled magnetic beads are repeated, the content increases to 11.3%, thus concentrated to 11.3-fold when compared to prior to the concentration (the content of the target double-stranded nucleic acid molecules in the sample is 1%). The concentration effect is increased to about 2-fold when compared with the case where the formation step of the complex B is performed once (with a content of 5.2% and a concentration effect (fold) of 5.2-fold).

TABLE 11

| Sample | Type of data | Content (%) | Concentration effect (fold) |
|---|---|---|---|
| L | Repeated three times | 11.3 | 11.3 |
|   | Repeated once | 5.2 | 5.2 |

Example 7-2

<Formation of Complex B Through the Formation of Complex b2>

1. Formation of Complex b2

A second PI polyamide equivalent to $1 \times 10^7$ molecules and 100 µg of streptavidin labeled magnetic beads were mixed in a microtube and incubated at room temperature for 60 minutes while mixing with a tube rotator to form a complex (complex b2) of the second PI polyamide and the streptavidin labeled magnetic beads. After the incubation, a magnetic stand was used for separation into a liquid component and a complex b2.

A second PI polyamide equivalent to $1 \times 10^7$ molecules and 100 µg of streptavidin labeled magnetic beads were both freshly added to the thus separated liquid component, followed by repeating the operations in a manner as described above and separating a complex b2. Likewise, the above operations were repeated three times and thus, 3 sets of complexes b2 (complex b2-1, complex b2-2 and complex b2-3 obtained in this order) were prepared.

2. Repeated Formation of Complex B (2-1) The complex b2-1 was added to a microtube in which the sample L had been placed, and incubated for 60 minutes while mixing with a tuber rotator to form a complex B-1. After the incubation, a magnetic stand was used for separation into a liquid component and the complex B-1.

(2-2) Using the complex b2-2 and the complex b2-3 prepared above in the respective liquid components, such a procedure as in (2-1) was repeated twice to form and separate a complex B-2 and a complex B-3.

3. Quantitative Analysis

The thus separated liquid components were provided as an analysis sample. The analysis sample was subjected to measurement of a content (%) of the target double-stranded nucleic acid molecules in the analysis sample by use of a commercially available reagent kit for droplet digital PCR (Prime PCR for ddPCR, manufactured by BIO-RD Inc.) and a droplet digital PCR system (QX 100™ droplet digital PCR, manufactured by BIO-RAD Inc.), from which a concentration effect (fold) (the content (%) of the target double-stranded nucleic acid molecules after concentration/the content (%) of the target double-stranded nucleic acid molecules in the respective samples) was calculated. It will be noted that the results of the case that the liquid component after the separation of the complex b2-1 was provided as an analysis sample were shown only for comparison.

The results of the measurement are shown in Table 12. In the inventive concentration method of target double-stranded nucleic acid molecule using the second PI polyamide, when the steps of forming and separating the complex B by mixing of the complex b2 and the sample are repeated, the content increases to 24.3%, thus concentrated to 24.3-fold when compared to prior to the concentration (the content of the target double-stranded nucleic acid molecules in the sample is 1%). The concentration effect is increased to about 1.5-fold when compared with the case where the formation step of the complex B is performed once (with a content of 15.0% and a concentration effect (fold) of 15-fold).

TABLE 12

| Sample | Type of data | Content (%) | Concentration effect (fold) |
|---|---|---|---|
| L | Repeated three times | 24.3 | 24.3 |
|  | Repeated once | 15.0 | 15.0 |

These results reveal that in the concentration method of target double-stranded nucleic acid molecules using a second PI polyamide, when the step of forming the complex B by mixing the complex b2 and the sample, or the step of forming the complex B by mixing the complex b1 and the carrier b (streptavidin labeled magnetic beads) is repeated, the target double-stranded nucleic acid molecules can be concentrated.

Example 8: Effect of a Salt and a Surfactant

There were used a sample M wherein target double-stranded nucleic acid molecules and non-target double-stranded nucleic acid molecules, which had base sequences different from each other as shown in Table 13 and had an amount ratio of 500 molecules:$5 \times 10^5$ molecules (i.e. the content of the target double-stranded nucleic acid molecules in the sample was 0.1%), an inventive first PI polyamide shown in FIG. 18 and an inventive carrier made of streptavidin labeled magnetic beads (Magnosphere™ MS300/Streptavidin, JSR Sciences, Inc.). The double-stranded nucleic acid molecules used were made of restriction enzyme-treated plasmid DNA. It will be noted that the target double-stranded nucleic acid molecules corresponded to a base sequence of K-RAS codon 12G12C mutation type and the non-target double-stranded nucleic acid molecules corresponded to a base sequence of K-RAS codon 12 wild-type. The formation of the complex a1 and the complex A was made under the three conditions indicated in Table 14 to confirm the effects of a salt and a surfactant.

1. Formation of Complex a1

The first PI polyamide equivalent to $1 \times 10^7$ molecules was added to a microtube in which the sample M had been placed, and incubated at room temperature for 60 minutes while mixing with a tube rotator to form a complex (complex a1) between the first P1 polyamide and streptavidin labeled magnetic beads.

2. Formation of Complex A

100 µg of streptavidin labeled magnetic beads was added to a microtube in which the complex a1 had been placed, and incubated at room temperature for 60 minutes while mixing with a tub rotator to form a complex A wherein the complex a1 and the streptavidin labeled magnetic beads were bound together. After the incubation, a magnetic stand was used for separation into a liquid component and the complex A.

3. Quantitative Analyses

20 µl of a TE buffer dispersion was added to the thus separated complex A for provision as an analysis sample. This analysis sample was subjected to measurement of a content (%) of the target double-stranded nucleic acid molecules therein by use of a commercially available reagent kit for droplet digital PCR (Prime PCR for ddPCR, manufactured by BIO-RD Inc.) and a droplet digital PCR system (QX 100™ droplet digital PCR, manufactured by BIO-RAD Inc.), from which a concentration effect (fold) (the content (%) of the target double-stranded nucleic acid molecules after concentration/the content (%) of the target double-stranded nucleic acid molecules in the sample) was calculated.

The results of the measurement are shown in Table 15. Where the complex a1 and the complex S are formed under the conditions 1 in the concentration method of the target double-stranded nucleic acid using the first PI polyamide (wherein the content of the target double-stranded nucleic acid molecules in the sample is 0.1%), the content increases to 4.2%, thus concentrated to 42-fold when compared to prior to the concentration. With conditions 2, the content increases to 49.0% and with conditions 3, the content increases to 52.1%, thus concentrated to 490-fold and 521-fold, respectively, when compared with prior to the concentration. Thus, the concentration effect increases to about 10-fold when compared with the conditions 1.

TABLE 13

| | Base sequence | Sequence No. |
|---|---|---|
| Target double-stranded nucleic acid molecule (sense side) | 5'-TGTGGC-3' | 4 |
| Non-target double-stranded nucleic acid molecule (sense side) | 5'-GGTGGC-3' | 5 |

TABLE 14

| Conditions 1 | Conditions 2 | Conditions 3 |
|---|---|---|
| Tween 20 0.5 v/v % NaCl 2 mols/liter | Tween 20 0.05 v/v % NaCl 1 mol/liter | Tween 2 0.0 v/v % NaCl 0 mol/liter |

TABLE 15

| Sample | Conditions | Content (%) | Concentration effect |
|---|---|---|---|
| M | 1 | 4.2 | 42 |
| | 2 | 49.0 | 490 |
| | 3 | 52.1 | 521 |

These results reveal that in the concentration method of target double-stranded nucleic acid molecules using the first PI polyamide, when the surfactant and the salt used for the formation of the complexes a1 and A are made under the conditions of 0.05 v/v % or below for the surfactant (Tween 20) and 1 mol/liter or below for the salt (NaCl), the target double-stranded nucleic acid molecules can be efficiently concentrated.

According to embodiments of the present invention, there can be simply achieved the concentration of target double-stranded nucleic acid molecules without provision of a high-accuracy temperature controlling apparatus and in facilities where there is no person having molecular biological expert knowledge and skills such as PCR.

The pyrrole-imidazole-containing polyamide can be used, aside from the diagnosis techniques, for example, in the high-sensitivity detection of a mutant gene by a versatile direct sequence technique on the clinical inspection spot or as a method of recovering and concentrating a mutant gene alone, contained in a small amount, from a biological sample for diagnostic pre-treatment. If the detection method of a mutant gene using a pyrrole-imidazole-containing polyamide is used, as it is, as an operational process on the clinical spot, not only the diagnostic sensitivity can be remarkably enhanced, but also the analysis efficiency can be increased with the reduction of inspection costs.

The present invention has an aspect to provide a method for concentrating target double-stranded nucleic acid molecules wherein a pyrrole-imidazole-containing polyamide is used, so that a one or more-base difference between non-target double-stranded nucleic acid molecules and the target double-stranded nucleic acid molecules is discriminated by a simple procedure without need of a high accuracy-temperature control device and the strict control of a reaction system to specifically capture the target double-stranded nucleic acid molecules or remove the non-target double-stranded nucleic acid molecules, and also a kit for concentrating such target double-stranded nucleic acid molecules.

The method and kit for concentrating target double-stranded nucleic acid molecules using a pyrrole-imidazole-containing polyamide according to embodiments of the invention are recited in the following [1] to [13].

[1] A method for concentrating target double-stranded nucleic acid molecules from a sample containing the target double-stranded nucleic acid molecules and non-target double-stranded nucleic acid molecules while separating from the non-target double-stranded nucleic acid molecules is characterized by comprising the steps of:

(1) mixing the sample,
a pyrrole-imidazole-containing polyamide (first PI polyamide) modified with a first linker molecule and capable of specifically binding to a specific sequence of the target double-stranded nucleic acid molecule, and
a carrier a modified with a first ligand capable of specifically binding and/or adsorbing to the first linker molecule thereby providing a mixed solution;

(2) forming a complex A by further binding the carrier a to the first PI polyamide of a complex a1, in which the target double-stranded nucleic acid molecule and the first PI polyamide are bound tougher in the mixed solution; and (3) recovering the complex A by separation from the mixed solution.

[2] A method for concentrating target double-stranded nucleic acid molecules from a sample containing the target double-stranded nucleic acid molecules and non-target double-stranded nucleic acid molecules while separating from the non-target double-stranded nucleic acid molecules is characterized by comprising the steps of:

(1) mixing the sample, and
a pyrrole-imidazole-containing polyamide (first PI polyamide) modified with a first linker molecule and capable of specifically binding to a specific sequence of the target double-stranded nucleic acid molecule thereby providing a mixed solution 1;

(2) forming a complex a1 in the mixed solution 1 wherein the target double-stranded nucleic acid molecule and the first PI polyamide are bound together;

(3) mixing, with the mixed solution 1, a carrier a modified with a first ligand molecule capable of specifically binding and/or adsorbing to the first linker molecule thereby providing a mixed solution 2:

(4) forming a complex A in the mixed solution 2 wherein the first PI polyamide of the complex a1 and the carrier a are bound together; and (5) recovering the complex A by separation from the mixed solution 2.

[3] A method for concentrating target double-stranded nucleic acid molecules from a sample containing the target double-stranded nucleic acid molecules and non-target double-stranded nucleic acid molecules while separating from the non-target double-stranded nucleic acid molecules is characterized by comprising the steps of:

(1) mixing a pyrrole-imidazole-containing polyamide (first PI polyamide) modified with a first linker molecule and capable of specifically binding to a specific sequence of the target double-stranded nucleic acid molecule,
a carrier a modified with a first ligand molecule capable of specifically binding and/adsorbing to the first linker molecule, and a solution or solvent thereby providing a mixed solution 1;

(2) forming a complex a2 in the mixed solution 1 wherein the first PI polyamide and the carrier a are bound together;

(3) mixing the sample with the mixed solution 1 to provide a mixed solution 2;

(4) forming a complex A in the mixed solution 2 wherein the first PI polyamide of the complex a2 and the target double-stranded nucleic acid molecule are bound together; and (5) recovering the complex A by separation from the mixed solution 2.

[4] A method for separating and removing non-target double-stranded nucleic acid molecules from a sample containing target double-stranded nucleic acid molecules and the non-target double-stranded nucleic acid molecules is characterized by comprising the steps of:

(1) mixing the sample, a pyrrole-imidazole-containing polyamide (second PI polyamide) modified with a second linker molecule and capable of specifically binding to a specific sequence of the non-target double-stranded nucleic acid molecule, and a carrier b modified with a second ligand molecule capable of specifically binding and/or adsorbing to the second linker molecule thereby providing a mixed solution;

(2) forming a complex B by further binding the carrier b to the second PI polyamide of the complex b1 wherein the non-target double-stranded nucleic acid molecule and the second PI polyamide are bound together in the mixed solution; and (3) removing the complex B by separation from the mixed solution.

[5] A method for removing non-target double-stranded nucleic acid molecules by separation from a sample containing target double-stranded nucleic acid molecules and the non-target double-stranded nucleic acid molecules is characterized by comprising the steps of:

(1) mixing the sample, and a pyrrole-imidazole-containing polyamide (second PI polyamide) modified with a second linker molecule and capable of specifically binding to a specific sequence of the non-target double-stranded nucleic acid molecule thereby providing a mixed solution 1;

(2) forming a complex b1 wherein the non-target double-stranded nucleic acid molecule and the second PI polyamide are bound together in the mixed solution 1;

(3) mixing, with the mixed solution 1, a carrier b modified with a second ligand molecule capable of specifically binding and/or adsorbing to the second linker molecule thereby providing a mixed solution 2;

(4) forming a complex B in the mixed solution 2 wherein the second PI polyamide of the complex b1 and the carrier b are bound together; and (5) removing the complex B by separation from the mixed solution 2.

[6] A method for removing non-target double-stranded nucleic acid molecules by separation from a sample containing target double-stranded nucleic acid molecules and the non-target double-stranded nucleic acid is characterized by comprising the steps of:

(1) mixing a pyrrole-imidazole-containing polyamide (second PI polyamide) modified with a second linker molecule and capable of specifically binding to a specific sequence of the non-target double-stranded nucleic acid molecules, a carrier b modified with a second ligand molecule capable of specifically binding and/or adsorbing to the second linker molecule, and a solution or solvent thereby providing a mixed solution 1;

(2) forming a complex b2 in the mixed solution 1 wherein the second PI polyamide and the carrier b are bound together;

(3) mixing the sample with the mixed solution 1 to provide a mixed solution 2;

(4) forming a complex B bound with the non-target double-stranded nucleic acid molecule of the complex b2 in the mixed solution 2; and (5) removing the complex B by separation from the mixed solution 2.

[7] A method for concentrating target double-stranded nucleic acid molecules from a sample containing the target double-stranded nucleic acid molecules and non-target double-stranded nucleic acid while separating from the non-target double-stranded nucleic acid molecules is characterized by comprising the steps of:

(1) mixing the sample, a pyrrole-imidazole-containing polyamide (first PI polyamide) modified with a first linker molecule and capable of specifically binding to a specific sequence of the target double-stranded nucleic acid molecules, and a pyrrole-imidazole-containing polyamide (second PI polyamide) modified with a second linker molecule and capable of specifically binding to a specific sequence of the non-target double-stranded nucleic acid molecule thereby providing a mixed solution 1;

(2) forming a complex a1 wherein the target double-stranded nucleic acid molecule and the first PI polyamide are bound together in the mixed solution and also a complex b1 wherein the non-target double-stranded nucleic acid molecule and the second PI polyamide are bound together in the mixed solution;

(3) mixing, with the mixed solution 1, a carrier a, which is modified with a first ligand molecule capable of specifically binding and/or adsorbing to the first linker molecule to provide a mixed solution 2;

(4) forming a complex A in the mixed solution 2 wherein the first PI polyamide of the complex a1 and carrier a are bound together; and (5) recovering the complex A by separation from the mixed solution 2.

[8] A method for separating non-target double-stranded nucleic acid molecules from a sample containing target double-stranded nucleic acid molecules and the non-target double-stranded nucleic acid molecules is characterized by comprising the steps of:

(1) mixing the sample, a pyrrole-imidazole-containing polyamide (first PI polyamide) modified with a first linker molecule and capable of specifically binding to a specific sequence of the target double-stranded nucleic acid molecules, and a pyrrole-imidazole-containing polyamide (second PI polyamide) modified with a second linker molecule and capable of specifically binding to a specific sequence of the non-target double-stranded nucleic acid molecules thereby providing a mixed solution 1;

(2) forming a complex a1 wherein the target double-stranded nucleic acid molecule and the first PI polyamide are bound together in the mixed solution 1 and also forming a complex b1 wherein the non-target double-stranded nucleic acid molecule and the second PI polyamide are bound together in the mixed solution 1;

(3) mixing, with the mixed solution 1, a carrier b modified with a second ligand molecule capable of binding and/or adsorbing to the second linker molecule to provide a mixed solution 2;

(4) forming a complex B in the mixed solution 2 wherein the second PI polyamide of the complex b1 and the carrier b are bound together;

(5) removing the complex B by separation from the mixed solution 2;

(6) mixing a carrier a, which is modified with a first ligand molecule capable of specifically binding and/or adsorbing to the first linker molecule being modified to the first PI polyamide, with the mixed solution 2 from which the complex B has been separated;

(7) forming a complex A by binging the complex a1 and the carrier a together; and (8) recovering the complex A by separation from the mixed solution 3.

[9] A method for concentrating target double-stranded nucleic acid molecules from a sample containing the target double-stranded nucleic acid molecules and non-target double-stranded nucleic acid molecules while separating from the non-target double-stranded nucleic acid molecules is characterized by comprising the steps of:

(1) mixing the sample, a pyrrole-imidazole-containing polyamide (first PI polyamide) modified with a first linker molecule and capable of specifically binding to a specific sequence of the target double-stranded nucleic acid molecules, a carrier a modified with a first ligand molecule capable of specifically binding and/or adsorbing to the first linker molecule, a pyrrole-imidazole-containing polyamide (second PI polyamide) modified with a second linker molecule and capable of specifically binding to a specific sequence of the non-target double-stranded nucleic acid molecules, and a carrier b modified with a second ligand molecule capable of specifically binding and/or adsorbing to the second linker molecule;

(2) forming a complex A by further binding the carrier a to the first PI polyamide of the complex a1 wherein the target double-stranded nucleic acid molecules and the first PI polyamide have been bound together in the mixed solution 1 and also forming a complex B by further binding the carrier b to the second PI polyamide of the complex b1 wherein the non-target double-stranded nucleic acid molecule and the second PI polyamide have been bound together in the mixed solution;

(3) removing the complex B by separation from the mixed solution 1; and (4) recovering the complex A by separation from the mixed solution 1.

[10] A method for concentrating target double-stranded nucleic acid molecules from a sample containing the target double-stranded nucleic acid molecules and non-target double-stranded nucleic acid molecules while separating from the non-target double-stranded nucleic acid molecules is characterized by comprising either a procedure of forming a complex A including forming the complex A by the steps of:

(1) mixing the sample, and a pyrrole-imidazole-containing polyamide (first PI polyamide) modified with a first linker molecule and capable of specifically binding to a specific sequence of the target double-stranded nucleic acid molecule thereby providing a mixed solution 1;

forming a complex a1 in the mixed solution 1 wherein the target double-stranded nucleic acid molecule and the first PI polyamide have been bound together;

(3) mixing, with the mixed solution 1, a carrier a modified with a first ligand molecule capable of specifically binding and/or adsorbing to the first linker molecule thereby providing a mixed solution 2; and (4) forming a complex A in the mixed solution 2 wherein the first P1 polyamide of the complex a1 and the carrier a are bound together; or a procedure of a complex A including forming the complex A by the steps including:

(1') mixing a pyrrole-imidazole-containing polyamide (first PI polyamide) modified with a first linker molecule and capable of specifically binding to a specific sequence of the target double-stranded nucleic acid molecule, a carrier a modified with a first ligand molecule capable of specifically binding and/or adsorbing to the first linker molecule, and a solution or solvent thereby providing a mixed solution 1';

(2') forming a complex a2 in the mixed solution 1' wherein the first PI polyamide and the carrier a are bound together;

(3') mixing the sample with the mixed solution to provide a mixed solution 2'; and (4') forming a complex A in the mixed solution 2' wherein the first PI polyamide of the complex a2 and the target double-stranded nucleic acid molecule are bound together; and further comprising selected from either a procedure of separating and removing the non-target nucleic acid, characterized by comprising the steps of:

(5) mixing, with the mixed solution 2 after the step (4) or the mixed solution 2' after the step (4'), the pyrrole-imidazole-containing polyamide (second PI polyamide) modified with a second linker molecule and capable of specifically binding to a specific sequence of the non-target double-stranded nucleic acid molecule to provide a mixed solution 3;

(6) forming a complex b1 in the mixed solution 3 wherein the non-target double-stranded nucleic acid molecule and the second PI polyamide are bound together;

(7) mixing, with the mixed solution 3, a carrier b modified with a second ligand molecule capable of specifically binding and/or adsorbing to the second linker molecule in the mixed solution 3 to provide a mixed solution 4;

(8) forming a complex B in the mixed solution 4 wherein the second PI polyamide of the complex b1 and the carrier b have been bound together; and (9) removing the complex B by separation from the mixed solution 4, or a procedure of separating and removing the non-target nucleic acid, characterized by comprising the steps of:

(5') mixing, with the mixed solution 2 after the step (4) or the mixed solution 2' after the step (4'), a pyrrole-imidazole-containing polyamide (second PI polyamide) modified with a second linker molecule and capable of specifically binding to a specific sequence of the non-target double-stranded nucleic acid molecule, a carrier b modified with a ligand molecule capable of specifically binding and/or adsorbing to the second linker molecule to provide a mixed solution 1, and further mixing with a solution or solvent to provide a mixed solution 3';

(6') forming a complex b2 in the mixed solution 3' wherein the second PI polyamide and the carrier b are bound together;

(7') mixing the sample with the mixed solution 3' to provide a mixed solution 4';

(8') forming a complex B bound with the non-target double-stranded nucleic acid molecule of the complex b2 in the mixed solution 4'; and (9') removing the complex B by separation from the mixed solution 4'; and

(10) recovering the complex A by separation from the mixed solution 4 or 4'.

[11] A method, characterized by comprising concentrating nucleic acid molecules each having a target base sequence by repeating one or more methods selected from [1] to [10] plural times.

[12] The method as recited in any one of [1] to [10], wherein the non-target double-stranded nucleic acid molecule is in a region of a specific base sequence of a gene selected from the genetic groups consisting of K-RAS, N-RAS, H-RAS, RHO, RAB, ARF, RAN, CYP, GSTT, NAT, TS, UGT, ERCC, MDR, CRHR, BRCA, MSH, CDA, DPD, OPRT, 5-HTT, Factor V, VKORC1, APEX1, DCK, DPYD, TYMP, MLH1, UPMS, PCNA, POLA, RRM1, SLC29A1, TK1, UNG, ACTB, AKT1, ALK, APC, BRAF, CHD1, CTNNB1, EGFR, ERBB2, FBXW7, FGFR2, FOXL2, GNAQ, GNAS, KIT, MAP2K1, MET, NRAS, PDGFRA, PIK3CA, PTEN, SMAD4, SRC, STK11, TP53, MLH1, MSH2, MSH6, APC, MEN1, RET, TP53, EGFR, BRAF, c-kit, PDGFRα, PDGFR, and TP53, wherein the target double-stranded nucleic acid molecule has one or more base mutations in the region of the specific base sequence of the gene selected from the above wild-type genetic groups.

[13] The method as recited in any one of [1] to [12] is characterized in that the pyrrole-imidazole-containing polyamide has a structure represented by the following formula 1

T-A1-H-A2-L        (Formula 1)

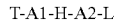

wherein T represents a terminal region, A1 and A2, respectively, represent a hybridizing region, H represents a connected region, and L represents a first linker molecule or second linker molecule, the hybridizing region, the connected region and the first linker molecule or second linker molecule are connected through an amide bond, respectively the terminal region is made of N,N-dimethylaminopropylamine, and the hybridizing region is one selectively connected from pyrrole (Py) imidazole (Im), and β-alanine (β-Ala).

[14] The method as recited in [1] to [13] is characterized in that the pyrrole-imidazole-containing polyamide has a cyclic structure represented by the following formula 2

Chemical Formula 1

(Formula 2)

wherein A1 and A2, respectively, represent a hybridizing region, H represents a connected region, and L represents a first linker molecule or second linker molecule, wherein the hybridizing region, the connected region and the first linker molecule or second linker molecule are connected through an amide bond, respectively and the hybridizing regions are, respectively, one selectively connected from pyrrole (Py), imidazole (Im) and β-alanine (β-Ala).

[15] The method as recited in any one of [1] to [14] is such that the sample is made of at least one selected from the group consisting of biopsies including blood serum, blood plasma, urine, pleural effusion, peritoneal effusion, peripheral blood and lymph fluid that contain nucleic acid molecules, and target double-stranded nucleic acid molecules contained in the sample are enabled to be concentrated.

[16] The method as recited in any one of the methods [1] to [15] is characterized in that the sample is one which contains nucleic acid molecules obtained through an extraction or purification procedure from the biopsy.

[17] A kit for use in the concentration method of double-stranded nucleic acid molecules having a target base sequence as recited in any one of [1] to [16] is characterized by comprising:

a PI polyamide modified with a linker molecule and including a hybridizing region which is capable of discriminating a one-base difference between the sequences of a target double-stranded nucleic acid molecule and a non-target double-stranded nucleic acid molecule and is able to discriminate a bindable sequence;

a carrier modified with a ligand molecule capable of specifically binding to the linker molecule; and a reagent selected from at least one or more of groups consisting of a pH buffer agent, a surfactant, a salt containing a divalent cation, a salt containing a monovalent cation, and a combination thereof, wherein the surfactant is at not larger than 0.05 v/v % relative to a mixed solution, the salt containing the divalent cation and/or the salt containing the monovalent cation is not larger than 1 mol/liter, the hybridizing region is such that a molecular design is enabled correspondingly to the base sequence of the target double-strand nucleic acid molecule or non-target double-stranded nucleic acid molecule, and the PI polyamide further has at least one of the following features (1) to (4):

(1) To bind to a base pair (T-A or A-T) within a target base sequence or in the vicinity thereof and contain at least one spacer molecule capable of forming a hair-pin shaped structure in the pyrrole-imidazole-containing polyamide;

(2) To bind a base pair (T-A or A-T) within a target base sequence or in the vicinity thereof and contain two or more spacer molecules capable of forming a hair-pin shaped structure in the pyrrole-imidazole-containing polyamide thereby enabling the formation of a cyclic structure;

(3) To contain at least one β-alanine residue in every 2 or 3 residues within the sequence; and (4) To be a sequence containing Py, Im and β-Ala each having a length sufficient to satisfactorily enable the recognition of the base sequence of a target double-stranded nucleic acid molecule and the base sequence of a non-target double-stranded nucleic acid molecule.

According to the concentration method of target double-stranded nucleic acid molecules related to an embodiment of the present invention, which makes use of a functional pyrrole-imidazole-containing polyamide having a sequence capable of binding to nucleic acid molecules having an arbitrary base sequence, the target double-stranded nucleic acid molecules can be concentrated by discriminating a one or more-base difference by a simple procedure without needing a high accuracy temperature control device and the strict control of a reaction system.

INDUSTRIAL APPLICABILITY

By the provision of the method of concentrating target double-stranded nucleic acid molecules according to an embodiment of the present invention, target double-stranded nucleic acid molecules can be concentrated by discriminating a one-base difference by a simple procedure without use of a high-accuracy temperature controlling apparatus and without need of exact control of a reaction system. Hence, the target double-stranded nucleic acid molecules can be detected and analyzed by an analysis method that would be insufficient in sensitivity under normal conditions, thus enabling genetic analysis or diagnosis, or clinical development by combination with a variety of analysis methods.

REFERENCE SIGNALS LIST

1 Target double-stranded DNA
2 First PT polyamide
3 First linker molecule (e.g., biotin)
4 Ligand molecule capable of specifically binding to the first linker molecule
8 Second linker molecule (e.g., biotin)
9 Ligand molecule capable of specifically binding to the second linker molecule (e.g., streptavidin)
5 Carrier a
6 Non-target double-stranded DNA
7 Second PI polyamide
10 Carrier b
11 Terminal region
12 Hybridizing region 1
13 Hybridizing region 2
14 Connected region
15 Linker molecule
100 Complex A
200 Complex B Obviously, numerous modifications and variations of the present invention are possible in light of the above teachings. It is therefore to be understood that within the scope of the appended claims, the invention may be practiced otherwise than as specifically described herein.

What is claimed is:

1. A method of separating a target double-stranded nucleic acid molecule from a sample, comprising:
mixing a sample, a first PI polyamide, and a carrier such that a mixed solution comprising the sample, the first PI polyamide, and the carrier is produced;
forming a complex A by binding the carrier to the first PI polyamide with which a target double-stranded nucleic acid molecule in the sample is bound in the mixed solution; and
separating the complex A from the mixed solution,
wherein the sample includes the target double-stranded nucleic acid molecule and a non-target double-stranded nucleic acid molecule, the first PI polyamide is a pyrrole-imidazole-containing polyamide which is modified with a first linker molecule and specifically binds to a sequence of the target double-stranded nucleic acid molecule in the sample, the carrier is modified with a first ligand which specifically binds or adsorbs to the first linker molecule, and a content of the target double-stranded nucleic acid molecule for separating the target double-stranded nucleic acid molecule from the sample is less than 1% in the sample.

2. The method of claim 1, wherein the mixing includes mixing the sample and the first PI polyamide to form a complex a1 by binding the first PI polyamide with the target double-stranded nucleic acid molecule in the mixed solution, and the forming of the complex A includes binding the carrier to the first PI polyamide in the complex a1.

3. The method of claim 2, wherein the mixing further includes mixing a second PI polyamide with the sample to form a complex b1 by binding the second PI polyamide with the non-target double-stranded nucleic acid molecule in the mixed solution.

4. The method of claim 1, wherein the mixing includes mixing the first PI polyamide and the carrier to form a complex a2 by binding the first PI polyamide with the carrier in the mixed solution, and the forming of the complex A includes binding the target double-stranded nucleic acid molecule to the first PI polyamide of the complex a2.

5. A method of removing a non-target double-stranded nucleic acid molecule from a sample including a target double-stranded nucleic acid molecule and the non-target double-stranded nucleic acid molecule, comprising:
(1) mixing the sample,
a pyrrole-imidazole-containing polyamide (second PI polyamide) modified with a second linker molecule and capable of specifically binding to a sequence of the non-target double-stranded nucleic acid molecule, and
a carrier b modified with a second ligand molecule capable of specifically binding and/or adsorbing to the second linker molecule such that a mixed solution is produced;
(2) forming a complex B by binding the carrier b to the second PI polyamide with which the non-target double-stranded nucleic acid molecule is bound in the mixed solution; and
(3) removing the complex B from the mixed solution wherein a content of the target double-stranded nucleic acid molecule is less than 1% in the sample.

6. The method of claim 5, wherein the mixing includes mixing the sample and the second PI polyamide to form a complex b1 by binding the second PI polyamide with the non-target double-stranded nucleic acid molecule in the mixed solution, and further the carrier b to form the complex B by binding the carrier b to the second PI polyamide of the complex b1.

7. The method of claim 5, wherein the mixing includes mixing the second PI polyamide and the carrier b to form a complex b2 by binding the second PI polyamide with the carrier b in the mixed solution, and further the sample to form the complex B by binding the non-target double-stranded nucleic acid molecule to the second PI polyamide of the complex b2.

8. The method of claim 6, wherein the mixing further includes mixing a first PI polyamide together with the sample and the second PI polyamide to form a complex a1, by binding the first PI polyamide with the target double-stranded nucleic acid molecule in the mixed solution, and the complex b 1,
and further:
(4) mixing a carrier a modified with a first ligand capable of specifically binding and/or adsorbing to the first linker molecule;
(5) forming a complex A by binding the carrier a to the first PI polyamide of a complex a1 in which the target double-stranded nucleic acid molecule is bound with the first PI polyamide in the mixed solution; and
(6) separating the complex A from the mixed solution.

9. A method of separating a target double-stranded nucleic acid molecule from a sample, comprising:
mixing a sample, a first PI polyamide, a first carrier, a second PI polyamide, and a second carrier such that a mixed solution comprising the sample, the first PI polyamide, the first carrier, the second PI polyamide, and the second carrier is obtained;

forming a complex A by binding the first carrier to the first PI polyamide with which a target double-stranded nucleic acid molecule in the sample is bound in the mixed solution and a complex B by binding the second carrier to the second PI polyamide with which a non-target double-stranded nucleic acid molecule in the sample is bound in the mixed solution;

removing the complex B from the mixed solution; and separating the complex A from the mixed solution, wherein the first PI polyamide is a pyrrole-imidazole-containing polyamide which is modified with a first linker molecule and specifically binds to a sequence of the target double-stranded nucleic acid molecule, the first carrier is modified with a first ligand molecule which specifically binds or adsorbs to the first linker molecule, the second PI polyamide is a pyrrole-imidazole-containing polyamide which is modified with a second linker molecule and specifically binds to a sequence of the non-target double-stranded nucleic acid molecule, the second carrier is modified with a second ligand molecule which specifically binds or adsorbs to the second linker molecule, and a content of the target double-stranded nucleic acid molecule for separating the target double-stranded nucleic acid molecule from the sample is less than 1% in the sample.

10. The method of claim 9, wherein the mixing includes mixing the sample and the first PI polyamide to form a complex a1 by binding the first PI polyamide with the target double-stranded nucleic acid molecule in the mixed solution, and the forming of the complex A includes binding the first carrier to the first PI polyamide in the complex a1 the mixing includes; or mixing the sample and the second PI polyamide to form a complex hi by binding the second PI polyamide with the non-target double-stranded nucleic acid molecule in the mixed solution, and the forming of the complex B includes binding the second carrier to the second PI polyamide the complex b1.

11. The method of claim 9, wherein the mixing includes mixing the sample and the first PI polyamide to form a complex a1 by binding the first PI polyamide with the target double-stranded nucleic acid molecule in the mixed solution, and the forming of complex A includes binding the first carrier to the first PI polyamide of the complex a1; or the mixing includes mixing the second PI polyamide and the second carrier to form a complex b2 by binding the second PI polyamide with the second carrier in the mixed solution, and the forming of complex B includes binding the non-target double-stranded nucleic acid molecule to the second PI polyamide of the complex b2.

12. The method of claim 9, wherein the mixing includes mixing the first PI polyamide and the first carrier to form a complex a2 by binding the first PI polyamide with the first carrier in the mixed solution, and the forming of complex A includes binding the target double-stranded nucleic acid molecule to the first PI polyamide of the complex a2; or the mixing includes mixing the sample and the second PI polyamide to forma complex b1 by binding the second PI polyamide with the non-target double-stranded nucleic acid molecule in the mixed solution, and the forming of complex B includes binding the second carrier to the second PI polyamide of the complex b1.

13. The method of claim 9, wherein the mixing includes mixing the first PI polyamide and the first carrier to form a complex a2 by binding the first PI polyamide with the first carrier a in the mixed solution, and the forming of complex A includes binding the target double-stranded nucleic acid molecule to the first PI polyamide of the complex a2; or the mixing includes mixing the second PI polyamide and the second carrier to form a complex b2 by binding the second PI polyamide with the second carrier in the mixed solution, and the forming of complex B includes binding the non-target double-stranded nucleic acid molecule to the second PI polyamide of the complex b2.

14. A method of concentrating a nucleic acid molecule having a target base sequence, comprising:

separating the nucleic acid molecule by the method of claim 1; and repeating the separating of the nucleic acid molecule at least once.

15. The method of claim 1, wherein the non-target double-stranded nucleic acid molecule is in a region of a base sequence on a gene in a wild-type genetic group selected from the group consisting of K-RAS, N-RAS, H-RAS, RHO, RAB, ARF, RAN, CYP, GSTT, NAT, TS, UGT, ERCC, MDR, CRHR, BRCA, MSH, CDA, DPD, OPRT, 5-HTT, Factor V, VKORC1, APEX1, DCK, DPYD, TYMP, MLH1, UPMS, PCNA, POLA, RRM1, SLC29A1, TK1 UNG, ACTB, AKT1, ALK, APC, BRAF, CHD1, CTNNB1, EGFR, ERBB2, FBXW7, FGFR2, FOXL2, GNAQ, GNAS, KIT, MAP2K1, MET, NRAS, PDGFRA, PIK3CA, PTEN, SMAD4, SRC, STK11, TP53, MLH1, MSH2, MSH6, APC, MEN1, RET, TP53, EGFR, BRAF, c-kit, PDGFRα, PDGFR, and TP53, and the target double-stranded nucleic acid molecule has at least one base mutation in the region of the base sequence on the gene in the wild-type genetic group.

16. The method of claim 1, wherein the pyrrole-imidazole-containing polyamide has a structure of formula 1, T-A1-H-A2-L, where T is a terminal region, A1 and A2 each are a hybridizing region, H is a connected region, and L is a first linker molecule or a second linker molecule; the hybridizing region, the connected region and the first linker molecule or second linker molecule are connected to each other through an amide bond; the terminal region comprises N,N-dimethylaminopropylamine, the hybridizing region is one selectively connected among pyrrole (Py), imidazole (Im), and β-alanine (β-Ala); and the connected region is one having 3 or more carbon atoms with a carbon-carbon single bond.

17. The method of claim 1, wherein the pyrrole-imidazole-containing polyamide has a cyclic structure of formula 2

(Formula 2)

wherein A1 and A2 each is a hybridizing region, H is a connected region, and L is a first linker molecule; the hybridizing region, the connected region and the first linker molecule are connected each other through an amide bond, A1 and A2 are, independently, hybridizing region selectively connected among pyrrole (Py), imidazole (Im) and β-alanine (β-Ala), and the connected region is one having 3 or more carbon atoms with a carbon-carbon single bond.

18. The method of claim 1, wherein the sample comprises at least one biopsy selected from the group consisting of blood serum, blood plasma, urine, pleural effusion, peritoneal effusion, peripheral blood and lymph fluid, which contains the target double-stranded nucleic acid molecule, and the target double-stranded nucleic acid molecule in the sample is capable of being concentrated.

19. The method of claim 1, wherein the sample comprises the target double-stranded nucleic acid molecule obtained through an extraction or purification procedure from a biopsy.

20. The method of claim 1, wherein the mixing comprises mixing the sample, the first PI polyamide, and the carrier at temperature in a range of 25° C. to 40° C.

* * * * *